US008648081B2

(12) United States Patent
An et al.

(10) Patent No.: US 8,648,081 B2
(45) Date of Patent: Feb. 11, 2014

(54) PARASITICIDAL DIHYDROISOXAZOLE COMPOUNDS

(75) Inventors: Zengyun An, Shanghai (CN); Liang Chen, Shanghai (CN); Shuhui Chen, Calabasas, CA (US); Jean Marie Defauw, New Palestine, IN (US); Scott Dale Holmstrom, Fishers, IN (US); Ping Hu, Shanghai (CN); Chongzhi Tang, Shanghai (CN); William Hunter White, Greenfield, IN (US); Wentao Wu, Shanghai (CN); Yang Zhang, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/883,025

(22) PCT Filed: May 8, 2012

(86) PCT No.: PCT/US2012/036883
§ 371 (c)(1),
(2), (4) Date: May 2, 2013

(87) PCT Pub. No.: WO2012/158396
PCT Pub. Date: Nov. 22, 2012

(65) Prior Publication Data
US 2013/0217699 A1   Aug. 22, 2013

(30) Foreign Application Priority Data

May 19, 2011 (WO) ................ PCT/CN2011/074294
Mar. 23, 2012 (WO) ................ PCT/CN2012/072878

(51) Int. Cl.
A61K 31/496 (2006.01)
A61K 31/422 (2006.01)
A61K 31/4439 (2006.01)
C07D 413/04 (2006.01)
C07D 413/14 (2006.01)
C07D 495/04 (2006.01)

(52) U.S. Cl.
USPC ...... 514/254.04; 514/301; 514/340; 514/367; 514/378; 544/367; 546/114; 546/272.1; 548/152; 548/240

(58) Field of Classification Search
None
See application file for complete search history.

(56) References Cited

FOREIGN PATENT DOCUMENTS

| WO | WO2007/072091 | 6/2007 |
|----|---------------|--------|
| WO | WO2007/079162 | 7/2007 |
| WO | WO2008/019760 | 2/2008 |
| WO | WO2008/122375 | 10/2008 |
| WO | WO2008/154528 | 12/2008 |
| WO | WO2009/002809 | 12/2008 |
| WO | WO2009/024541 | 2/2009 |
| WO | WO2010/070068 | 6/2010 |
| WO | WO2010/079077 | 7/2010 |
| WO | WO2012/017359 | 2/2012 |
| WO | WO2012/038851 | 3/2012 |

*Primary Examiner* — Kamal Saeed
(74) *Attorney, Agent, or Firm* — McAndrews, Held & Malloy Ltd.

(57) ABSTRACT

Provided are dihydroisoxazole compounds I useful for controlling parasites both in animals and agriculture. Further provided are methods for controlling parasite infestations of an animal by administering an effective amount of a compound as described above, or a pharmaceutically acceptable salt thereof, to an animal, as well as formulations for controlling parasite infestations using the compounds described above or an acceptable salt thereof, and an acceptable carrier. Also provided are compounds and processes useful for making the dihydroisoxazole compounds.

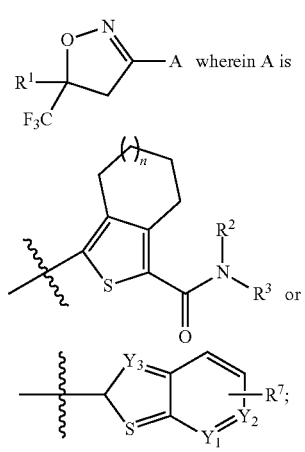

38 Claims, No Drawings

PARASITICIDAL DIHYDROISOXAZOLE COMPOUNDS

Ectoparasites such as fleas, lice, flies, mosquitoes, ticks and mites, as well as endoparasites such as gastrointestinal tract nematodes, flukes, and filarids, are problematic for man and animal alike. Such parasites seriously impact productivity in the domesticated animal industry by reducing weight gain, causing poor quality hide, wool, and meat, and in some cases resulting in death. Ecto- and endoparasites are also responsible, in part, for the spread of disease and discomfort in food and companion animals. Ectoparasites in particular are known to harbor and transmit a variety of microbial pathogens, including bacteria, viruses and protozoan parasites, many of which are pathogenic to humans, other warm-blooded mammals and birds. Diseases in which ectoparasites have been implicated include, but are not limited to, malaria, lymphatic- and blood-born filariasis, trachoma, trypanosomiasis, Leishmaniasis, Rocky Mountain Spotted Fever, Lyme Disease, babesiosis, and food-borne illnesses due to *Salmonella*, *E. coli* and *Campylobacter*, for example.

The medical importance of parasiticide infestations has prompted the development of reagents capable of controlling such. Commonly encountered methods to control parasiticide infestation, for example, have generally focused on use of insecticides, which are often unsuccessful or unsatisfactory for one or more of the following reasons: (1) failure of owner or applicator compliance (frequent administration is required); (2) behavioral or physiological intolerance of the animal to the pesticide product or means of administration; (3) the emergence of ectoparasites resistant to the reagent; and (4) negative impact on the environment and/or toxicity.

Specifically, ticks parasitize wild as well as domesticated animals and humans, and are known or suspected to be responsible for the transmission of pathogens including bacteria, viruses and protozoan parasites. Currently, ticks are considered to be second in the world to mosquitoes as vectors of human diseases, but they are considered to be the most important vector of pathogens in North America. Effective elimination of tick infestations is difficult and often impractical, due to the need for concomitant treatment of the immediate host as well as the environmental reservoir. Presently, tick control is effected by integrated pest management in which different control methods are adapted to one area or against one tick species with due consideration to their environmental effects.

While the use of insecticides and pesticides have been beneficial, alternative or improved compounds, formulations, and methods are needed. Desirable compounds, formulations, and methods would not only provide alternative therapies, but would also overcome one or more of the limitations of current approaches. Such limitations include toxicity and safety of both the animal and the user/owner, limited efficacy (e.g., potency and duration), and resistance issues. Also impacting the beneficial use of insecticides and pesticides are administration obstacles, which include mode and recurrence of administration. For example, reducing the frequency of administration while maintaining efficacy is desirable, as excessive and repeated treatment of animals is often inconvenient and/or difficult.

The present invention encompasses parasiticidal compounds, methods, and formulations for use in and on animals and plants, and which provide alternative options for combating parasiticidal infestations, particularly ectoparasiticidal infestations. Further, certain aspects of the invention overcome at least some limitations in the use of current insecticides and pesticides, particularly in providing effective long term, safe control of parasites.

Provided are compounds, and salts thereof, of formula I:

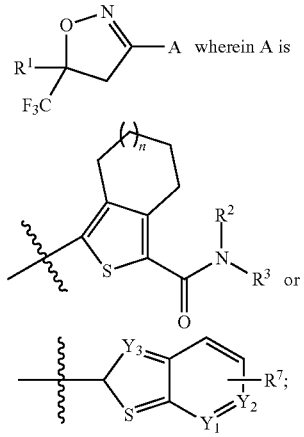

wherein A is n is 0 or 1;

$R^1$ is thienyl or phenyl, said thienyl or phenyl substituted with 2 or 3 of the same or different halo atoms;

$R^2$ is at each occurrence independently hydrogen, $C_1$-$C_5$ alkyl, $C_3$-$C_6$ cycloalkyl, or $C_1$-$C_5$ haloalkyl;

$R^3$ is

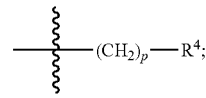

p is at each occurrence independently 0 or 1;

$R^4$ is $C_1$-$C_5$ alkyl, $C_1$-$C_5$ haloalkyl, $C_1$-$C_5$ cyanoalkyl, $C_1$-$C_5$ alkylthio, $C_3$-$C_6$ cycloalkyl optionally substituted with hydroxy, halo, or $C_1$-$C_5$ alkyl: $C_3$-$C_5$ cycloheteroalkyl optionally substituted with $C_1$-$C_5$ alkyl, $C_3$-$C_6$ cycloalkyl, or $C_1$-$C_5$ haloalkyl: phenyl, thienyl, pyridinyl, or

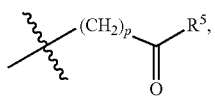

wherein one of the carbons in said cycloalkyls, independently, or cycloheteroalkyl may form a carbonyl group, and wherein said phenyl, thienyl, or pyridinyl is optionally substituted with halo or a carbamoyl group;

$R^5$ is hydroxy, —O—($C_1$-$C_5$ alkyl), or

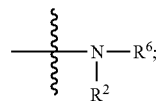

$R^6$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl;

or $R^2$ and $R^3$ combine to form, with the nitrogen to which they are attached,

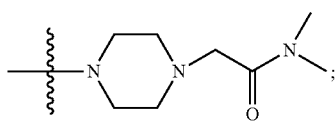 [SMILES: *N1CCN(CC(=O)N(C)C)CC1]

$Y_1$, $Y_2$, and $Y_3$ are carbon or nitrogen with at most only one of $Y_1$, $Y_2$, and $Y_3$ being nitrogen, and when $Y_1$, $Y_2$, or $Y_3$ is a carbon, each may be substituted by $C_1$-$C_5$ alkyl;

$R^7$ is hydrogen, halo, $C_1$-$C_5$ alkyl, or

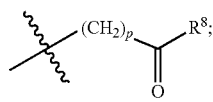

$R^8$ is hydroxy, —O—($C_1$-$C_5$ alkyl), or

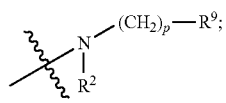

$R^9$ is $C_1$-$C_5$ alkyl,

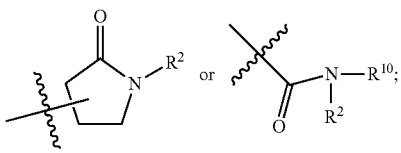

and $R^{10}$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl.

The invention provides a formulation, including a pharmaceutical formulation, comprising a compound or salt of formula I and one or more acceptable carriers. The formulation may further comprise at least one additional active ingredient. A pharmaceutical formulation of the invention may be a human pharmaceutical formulation or a veterinary pharmaceutical formulation.

The invention provides a method of controlling ecto- and endoparasite infestations of an animal in need thereof comprising administering an effective amount of a compound or salt of formula I to said animal. The method may further provide administering at least one other active ingredient to said animal. The animal may be a mammal, and may be a human or a companion animal, for example, a dog or cat.

The present invention provides a method for preventing and treating diseases transmitted through parasites comprising administering at least one compound of the invention to an animal in need thereof.

The invention provides a method for controlling parasites, characterized in that a compound of formula I is allowed to act on the pests and/or their habitat. The invention provides the use of compounds or salts thereof of formula I for controlling pests.

The invention provides a compound or salt of formula I for use in therapy. The invention further provides a compound or salt of formula I for use in controlling ecto- and endoparasite infestations. The invention also provides use of a compound or salt of formula I for the manufacture of a formulation or medicament for controlling ecto- and endoparasite infestations.

The invention provides compounds of Formula II, or a salt thereof, of the formula

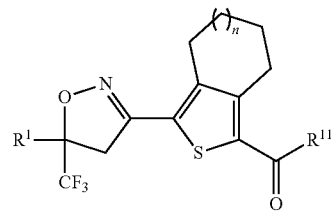

wherein n is 0 or 1;

$R^1$ is thienyl or phenyl, said thienyl or phenyl substituted with 2 or 3 of the same or different halo atoms; and $R^{11}$ is hydroxy, —O—($C_1$-$C_4$ alkyl), or a halo atom.

These compounds have utility as intermediates in the processes for preparing certain compounds of Formula I. These Formula II compounds may be chemically modified to result in certain Formula I compounds.

The host animal may be a mammal or non-mammal, such as a bird (turkeys, chickens) or fish. Where the host animal is a mammal, it may be a human or non-human mammal. Non-human mammals include domestic animals, such as livestock animals and companion animals. Livestock animals include cattle, camellids, pigs, sheep, goats, and horses. Companion animals include dogs, rabbits, cats, and other pets owned and maintained in close association with humans as part of the human-animal bond.

Parasites, sometimes also referred to as pests, include both ectoparasites and endoparasites. Ectoparasites include insect and acarine pests which commonly infest or infect animals, and include the egg, larval, pupal, nymphal, and adult stages thereof. Such pests include fleas, lice, mosquitoes, mites, ticks, beetles, and blood-sucking, biting, or nuisance fly species. Endoparasites include nematode pests which commonly infect animals, and include the egg, larval, and adult stages thereof. Such pests include helminths (hookworms, tapeworms, heartworms), and are commercially important because they cause serious diseases in animals, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematodes are *Haemonchus, Trichostrcngyius, Qstertagia, Nematotiirus, Cooperia, Ascaris, Bunostonum, Gesophagostonum, Charbertia, Trichuris, Strongyius, Trichonema, Dictyocaulus, Capsliarsa, Heterakis, Toxocara, Ascaridia, Oxyuris, Ancyiostoma, Uncinaria, Toxascaris* and *Parascaris*. The trematodes include, in particular, the family of Fasciolideae, especially *Fasciola hepatica*.

Controlling refers to either ameliorating or eliminating a current infestation, or preventing an infestation, in or on an animal host or a plant.

Effective amount refers to the amount of a compound of formula I, or a salt thereof, sufficient to control an ecto- or endoparasite infestation, and includes causing a measurable reduction in the ecto- or endoparasite infestation population, and as such will depend upon several factors. For use on or in animals, ranges for a compound of formula I, or a salt thereof, in the methods include from 0.01 to 1000 mg/kg and more desirably, 0.1 to 100 mg/kg of the animal's body weight. The frequency of the administration will also be dependent upon several factors, and can be a single dose administered once a day, once a week, or once a month, for a duration determined by the attending doctor or veterinarian. Additional active ingredients may be administered with a compound of formula I.

Pharmaceutically acceptable as used in this application, for example with reference to salts and formulation components such as carriers, includes "veterinarily acceptable", and thus includes both human and animal applications independently.

Salts of the compounds of the invention, including pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

The compounds of the invention and their salts may be formulated as pharmaceutical compositions for administration. Such pharmaceutical compositions and processes for making the same are known in the art for both humans and non-human mammals. See, e.g., REMINGTON: THE SCIENCE AND PRACTICE OF PHARMACY, (A. Gennaro, et al., eds., 19$^{th}$ ed., Mack Publishing Co., 1995). Formulations can be administered through various means, including oral administration, parenteral administration such as injection (intramuscular, subcutaneous, intravenous, intraperitoneal) or the like; topical application with or without transdermal penetration such as dipping, spray, bathing, washing, pouring-on and spotting-on, and dusting, or the like. Additional active ingredients may be included in the formulation containing a compound of the invention or a salt thereof.

Carrier is used herein to describe any ingredient other than the active component(s) in a formulation. The choice of carrier will to a large extent depend on factors such as the particular mode of administration or application, the effect of the carrier on solubility and stability, and the nature of the dosage form.

$C_1$-$C_5$ alkyl refers to straight chain and branched alkyls having one to five carbon atoms, and includes methyl, ethyl, propyl, n-butyl, iso-butyl, pentyl, isopentyl, and neopentyl.

$C_2$-$C_5$ alkynyl refers to straight chain and branched alkynyls having two to five carbon atoms, and includes ethynyl, 1-propynyl, 2-propynyl, 1-butynyl, 3-methyl-1-butynyl, pentynyl, isopentynyl, and neopentynyl.

Halogen or halo refers to fluorine, bromine, chlorine, and iodine.

Haloalkyl as used herein refers to an alkyl (as noted above) substituted with one or more halo atoms. Such groups include trifluoromethyl, difluoromethyl, fluoromethyl, methylchloride, dichloromethyl, pentylchloride, butyl chloride, and isopropyl chloride.

Cyanoalkyl as used herein refers to an alkyl (as noted above) substituted with a cyano group.

Alkylthio as used herein refers to an alkyl (as noted above) having a sulfur in the group.

$C_3$-$C_6$ cycloalkyl refers to cyclopropyl, cyclobutyl, cyclopentyl, and cyclohexyl.

$C_3$-$C_5$ cycloheteroalkyl refers to a saturated ring which has 3 to 5 carbons and a hetero atom. The hetero atom may be sulfur, oxygen, nitrogen, or a sulfonyl group.

Diseases transmitted through parasites, particularly ectoparasites, are, for example bacterial, viral, rickettsial and protozoal vector-borne diseases. Examples of viral diseases transmitted through arboviruses, i.e. arthropod borne viruses, are Crimean-Congo Hemorrhagic Fever (CCHF), Febrile illness, Papataci fever, Encephalitis, Meningitis, which are caused by Bunyaviridae such as Bunyavirus, Nairovirus or Phlebovirus; Bluetongue, meningoencephalits, Febrile illness, hemorhagic fever, which are caused by Reoviridae, such as Orbivirus, Colitivirus; Febrile illness, rash, encephalitis, polyarthritis, lymphadenitis, which are caused by Togaviridae, such as Sindbisvirus, Chikungunya Virus; tick-borne meningoencephalitis, Dengue hemorhagic fever, encephalitis, Febrile illness, Yellow fever, which are caused by Flaviviridae, such as Flavivirus (including diverse sub-groups). Examples of bacterial diseases transmitted through parasites are Rickettsiosis, such as Rocky Mountain spotted fever, tick typhus caused by infection through *Rickettsia* ssp; Tularemia caused by infection through *Francisella tularensis; Borreliosis* or *Spirochaetosis*, such as Lyme disease, or relapsing fever, caused, by infection through *Borrelia* ssp.; Ehrllichiosis caused by infection through *Ehrlichia* ssp.; Plague, caused by infection through *Yersinia* ssp. Examples of protozoal or rickettsial borne diseases are Babesiosis, such as Texas fever, red water disease, Q-fever caused by infection through *Babesia* ssp.; Theileriosis, such as east coast fever, Mediterranean coast fever, caused by infection through *Theileria* ssp.; Nagana disease, Sleeping sickness caused by infection through *Trypanosoma* ssp., Anaplasmosis caused by infection through *Anaplasma* ssp.; Malaria caused by infection through *Plasmodium* ssp.; Leishmaniasis caused by infection through *Leishmania* ssp.

Given their activity, certain of the compounds of the invention are suitable as soil insecticides against pests in the soil, as well as insecticides for plants, such as cereals, cotton, rice, maize, soya, potatoes, vegetables, fruit, tobacco, hops, citrus, and avocados. Certain compounds according to the invention are suitable for protecting plants and plant organs, for increasing the harvest yields, and for improving the quality of the harvested material which are encountered in agriculture, in horticulture, in forests, in gardens, and leisure facilities, and in the protection of stored products and of materials. They may be employed as plant protection agents.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out by conventional and known means, including directly acting on, or by allowing the compounds to act on, the surroundings, habitat or storage space by the customary treatment methods, for example by immersion, spraying, evaporation, fogging, scattering, painting on, injection and, in the case of propagation material, in particular in the case of seeds, also by applying one or more coats.

The compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are extenders, solvents, and carriers.

Following are Schemes A-J and examples for preparing the compounds of the invention. The Schemes, examples, and information contained therein are illustrative, and can be modified in ways known in the art to obtain the desired results.

Scheme A

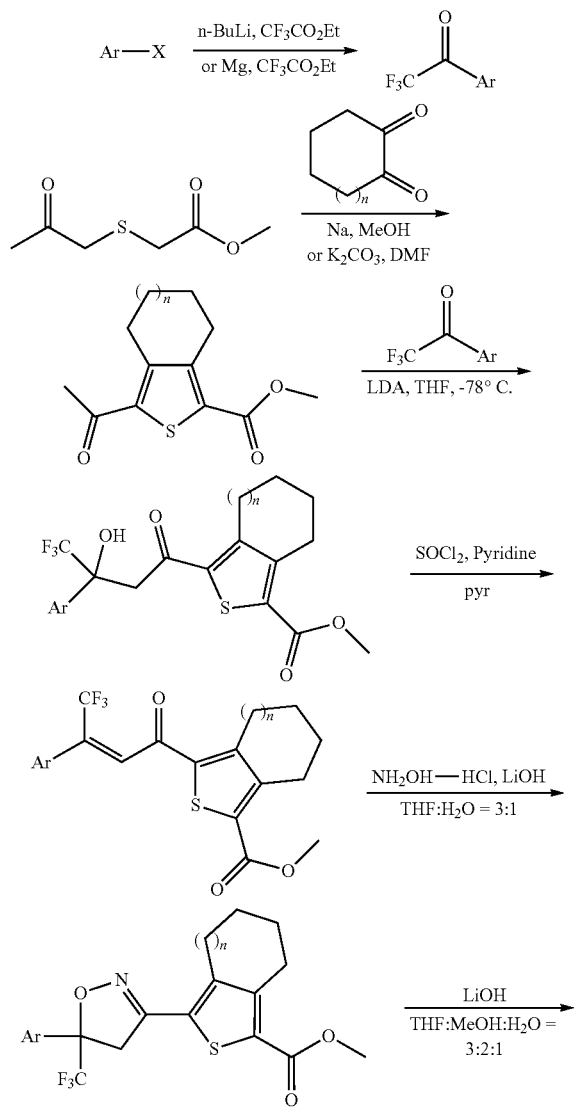

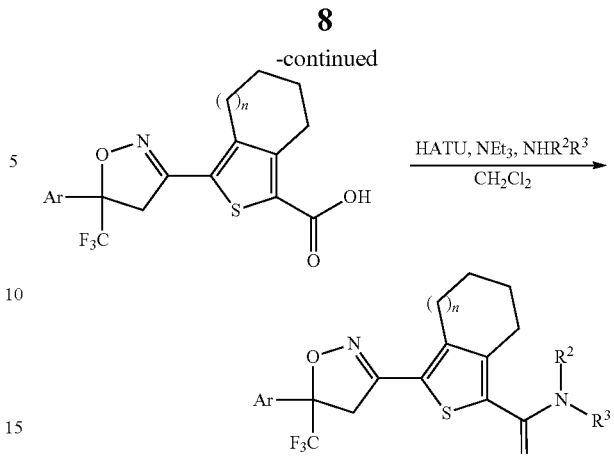

Preparation 1

Methyl 2,2,2-trifluoro-1-(3,4,5-trichlorothiophen-2-yl)ethanone

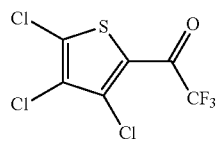 [SMILES: O=C(c1sc(Cl)c(Cl)c1Cl)C(F)(F)F]

Add a solution of n-BuLi (21.6 mL, 2.5 M in hexane, 54.0 mmol) to a solution of 2,3,4,5-tetrachloro-thiophene (10 g, 45.0 mmol) in dry THF (160 mL) at −78° C. and stir the mixture for 2 hours. Add a solution of trifluoro-acetic acid ethyl ester (9.59 g, 67.6 mmol) in THF (15 mL) and stir at −78° C. for additional 2.5 hours. Quench the reaction with saturated NH$_4$Cl solution (100 mL). Extract the aqueous mixture with EtOAc (100 mL×3). The combined organic layers are washed with brine, dried over anhydrous Na$_2$SO$_4$, and evaporate under vacuum. Purify the residue by a flash column on silica gel eluting with PE:EtOAc (10:1 to 5:1) to afford 2,2,2-trifluoro-1-(3,4,5-trichloro-thiophen-2-yl)-ethanone as a brown oil (10.4 g, 81.9%). $^{13}$F NMR (400 MHz, CDCl$_3$) δ −73.38 (s, 3F).

Preparation 2

Methyl 3-acetyl-4,5,6,7-tetrahydrobenzo[c]thiophene-1-carboxylate

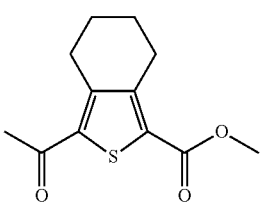 [SMILES: COC(=O)c1sc(C(C)=O)c2c1CCCC2]

Add methyl 2-(2-oxopropylthio)acetate (35.4 g, 183.2 mmol) to a freshly prepared solution of solid sodium (8.78 g, 381.5 mmol) in dry MeOH (300 mL) at 0° C., followed by addition of a solution of cyclohexane-1,2-dione (20 g, 152.6 mmol) in MeOH (30 mL). Stir the mixture at 0° C. for 30 min and then at 50-60° C. for additional 1.5 hour. Remove the solvent under vacuum and dilute the residue with water (100 mL). Extract the aqueous mixture with ethyl acetate (100 mL×3). The combined organic layers are washed with brine, dried over anhydrous $Na_2SO_4$, and evaporated under vacuum. Purify the residue by a flash column on silica gel eluting with PE:EtOAc (50:1 to 30:1) to afford methyl 3-acetyl-4,5,6,7-tetrahydrobenzo[c]thiophene-1-carboxylate as a white solid (10 g, 27.6%). MS (m/z): 239 (M+1).

Preparation 3

Methyl 3-acetyl-4,5,6,7-tetrahydrobenzo[c]thiophene-1-carboxylate

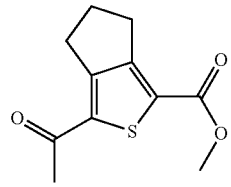

Stir a mixture of Cyclopentane-1,2-dione (2.00 g, 20.4 mmol), methyl 2-(2-oxopropylthio)acetate (3.31 g, 20.4 mmol) and potassium carbonate (5.63 g, 40.8 mmol) in DMF (40 mL) at 80° C. for 4 hours. Filter off the mixture and remove the solvent under vacuum. Purify the residue by a flash column on silica gel eluting with PE:EtOAc (8:1 to 6:1) to afford 3-Acetyl-5,6-dihydro-4H-cyclopenta[c]thiophene-1-carboxylic acid methyl ester as a pale yellow solid (206 mg, 4.5%). MS (m/z): 225 (M+1).

Preparation 4

Methyl 3-(3-(3,5-dichlorophenyl)-4,4,4-trifluoro-3-hydroxybutanoyl)-4,5,6,7-tetrahydrobenzo[c]thiophene-1-carboxylate

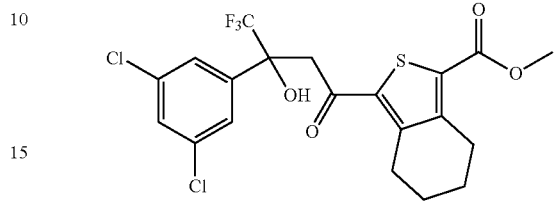

Add a solution of LDA (2M in THF, 19.5 mL, 3.89 mmol) to a suspension of 3-acetyl-4,5,6,7-tetrahydrobenzo[c]thiophene-1-carboxylate (7.4 g, 3.11 mmol) in dry THF (80 mL) at −78° C. under $N_2$. After stirring for 1.5 h, add 1-(3,5-Dichloro-phenyl)-2,2,2-trifluoro-ethanone (9.9 g, 3.73 mmol) to the reaction mixture and stir the resultant mixture at the same temperature for additional 2 hours. Quench the reaction with saturated $NH_4Cl$ aqueous solution. Extract the aqueous mixture with EtOAc (100 mL×3). The combined organic layers are washed with brine, dried over anhydrous $Na_2SO_4$ and concentrated under vacuum. Purify the residue by silica gel chromatograph (PE:EtOAc 50:1) to afford methyl 3-(3-(3,5-dichlorophenyl)-4,4,4-trifluoro-3-hydroxybutanoyl)-4,5,6,7-tetrahydrobenzo[c]thiophene-1-carboxylate as an orange solid (9.1 g, 60.4%). MS (m/z): 481 (M+1).

The following compounds are prepared essentially by the method of Preparation 4.

| Prep. No. | Chemical name | Structure | Physical data |
|---|---|---|---|
| 5 | 3-[3-(3,5-Dichloro-phenyl)-4,4,4-trifluoro-3-hydroxy-butyryl]-5,6-dihydro-4H-cyclopenta[c]thiophene-1-carboxylic acid methyl ester | 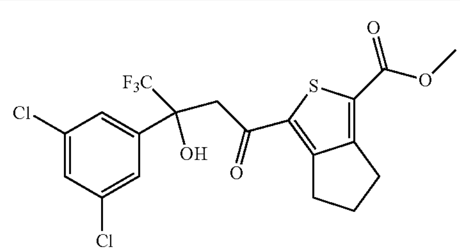 [SMILES: COC(=O)c1sc(C(=O)CC(O)(c2cc(Cl)cc(Cl)c2)C(F)(F)F)c2c1CCC2] | MS (m/z): 465 (M − 1). |
| 6 | 3-[4,4,4-Trifluoro-3-hydroxy-3-(3,4,5-trichloro-thiophen-2-yl)-butyryl]-4,5,6,7-tetrahydro-benzo[c]thiophene-1-carboxylic acid methyl ester | 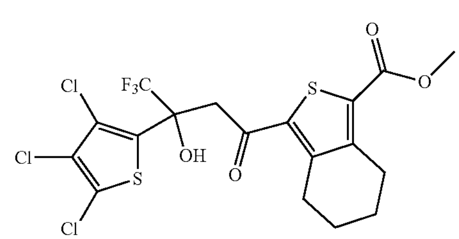 [SMILES: COC(=O)c1sc(C(=O)CC(O)(c2sc(Cl)c(Cl)c2Cl)C(F)(F)F)c2c1CCCC2] | MS (m/z): 519 (M − 1). |

| Prep. No. | Chemical name | Structure | Physical data |
|---|---|---|---|
| 7 | 3-[4,4,4-Trifluoro-3-hydroxy-3-(3,4,5-trichloro-phenyl)-butyryl]-4,5,6,7-tetrahydro-benzo[c]thiophene-1-carboxylic acid methyl ester | 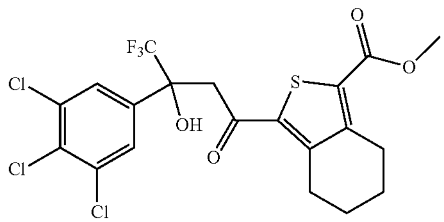 [SMILES: COC(=O)c1sc(C(=O)CC(O)(c2cc(Cl)c(Cl)c(Cl)c2)C(F)(F)F)c2c1CCCC2] | MS (m/z): 515 (M + 1) |
| 8 | 3-[3-(3,5-Dichloro-4-fluoro-phenyl)-4,4,4-trifluoro-3-hydroxy-butyryl]-4,5,6,7-tetrahydro-benzo[c]thiophene-1-carboxylic acid methyl ester | 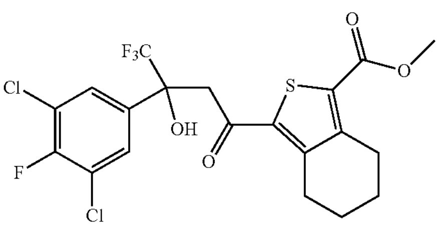 [SMILES: COC(=O)c1sc(C(=O)CC(O)(c2cc(Cl)c(F)c(Cl)c2)C(F)(F)F)c2c1CCCC2] | MS (m/z): 499 (M + 1) |
| 9 | 3-[4,4,4-Trifluoro-3-hydroxy-3-(3,4,5-trichloro-phenyl)-butyryl]-5,6-dihydro-4H-cyclopenta[c]thiophene-1-carboxylic acid methyl ester | 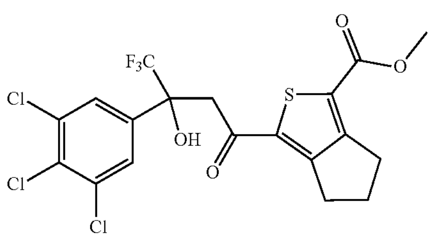 [SMILES: COC(=O)c1sc(C(=O)CC(O)(c2cc(Cl)c(Cl)c(Cl)c2)C(F)(F)F)c2c1CCC2] | MS (m/z): 501 (M + 1) |
| 10 | 3-[3-(3,5-Dichloro-4-fluoro-phenyl)-4,4,4-trifluoro-3-hydroxy-butyryl]-5,6-dihydro-4H-cyclopenta[c]thiophene-1-carboxylic acid methyl ester | 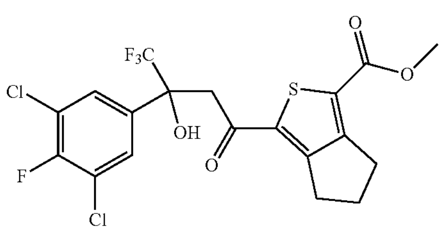 [SMILES: COC(=O)c1sc(C(=O)CC(O)(c2cc(Cl)c(F)c(Cl)c2)C(F)(F)F)c2c1CCC2] | MS (m/z): 485 (M + 1) |

Preparation 11

3-[3-(3,5-Dichloro-phenyl)-4,4,4-trifluoro-but-2-enoyl]-4,5,6,7-tetrahydro-benzo[c]thiophene-1-carboxylic acid methyl ester

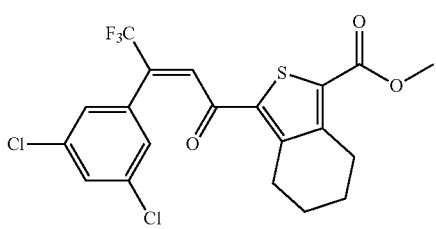 [SMILES: COC(=O)c1sc(C(=O)/C=C(\c2cc(Cl)cc(Cl)c2)C(F)(F)F)c2c1CCCC2]

Stir a mixture of methyl 3-(3-(3,5-dichlorophenyl)-4,4,4-trifluoro-3-hydroxyl butanoyl)-4,5,6,7-tetrahydrobenzo[c]thiophene-1-carboxylate (9.1 g, 18.9 mmol), $SOCl_2$ (9.0 g, 5.5 mL, 75.6 mmol) and pyridine (2.99 g, 3.1 mL, 37.8 mmol) in anhydrous DCM (100 mL) at ambient temperature overnight. Dilute the resultant mixture with saturated $NH_4Cl$ aqueous solution. Extract the aqueous mixture with DCM (100 mL×3). The combined organic layers are washed with brine, dried over anhydrous $Na_2SO_4$ and concentrated under vacuum. Purify the residue by silica gel chromatograph (PE: EtOAc 50:1) to afford 3-[3-(3,5-Dichloro-phenyl)-4,4,4-trifluoro-but-2-enoyl]-4,5,6,7-tetrahydro-benzo[c]thiophene-1-carboxylic acid methyl ester as an orange solid (8.75 g, 100%). (m/z): 463 (M+1).

The following compounds are prepared essentially by the method of Preparation 11.

| Prep. No. | Chemical name | Structure | Physical data |
|---|---|---|---|
| 12 | 3-[3-(3,5-Dichloro-phenyl)-4,4,4-trifluoro-but-2-enoyl]-5,6-dihydro-4H-cyclopenta[c]thiophene-1-carboxylic acid methyl ester | 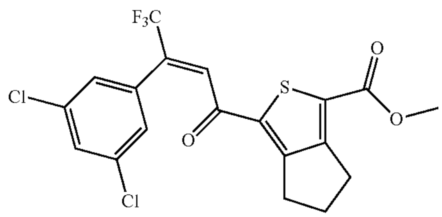 [SMILES: COC(=O)c1sc(C(=O)/C=C(\c2cc(Cl)cc(Cl)c2)C(F)(F)F)c2c1CCC2] | MS (m/z): 447 (M − 1). |
| 13 | 3-[4,4,4-Trifluoro-3-(3,4,5-trichloro-thiophen-2-yl)-but-2-enoyl]-4,5,6,7-tetrahydro-benzo[c]thiophene-1-carboxylic acid methyl ester]thiophene-1-carboxylic acid methyl ester | 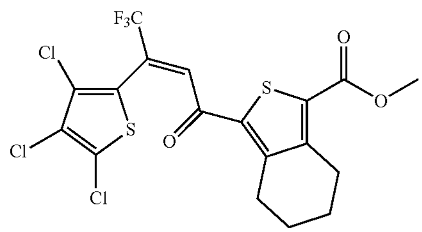 [SMILES: COC(=O)c1sc(C(=O)/C=C(\c2sc(Cl)c(Cl)c2Cl)C(F)(F)F)c2c1CCCC2] | MS (m/z): 501 (M − 1). |
| 14 | 3-[4,4,4-Trifluoro-3-(3,4,5-trichloro-phenyl)-but-2-enoyl]-4,5,6,7-tetrahydro-benzo[c]thiophene-1-carboxylic acid methyl ester | 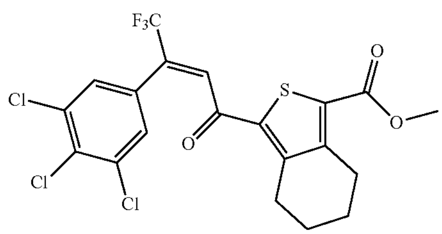 [SMILES: COC(=O)c1sc(C(=O)/C=C(\c2cc(Cl)c(Cl)c(Cl)c2)C(F)(F)F)c2c1CCCC2] | MS (m/z): 497 (M + 1). |
| 15 | 3-[3-(3,5-Dichloro-4-fluoro-phenyl)-4,4,4-trifluoro-but-2-enoyl]-4,5,6,7-tetrahydro-benzo[c]thiophene-1-carboxylic acid methyl ester | 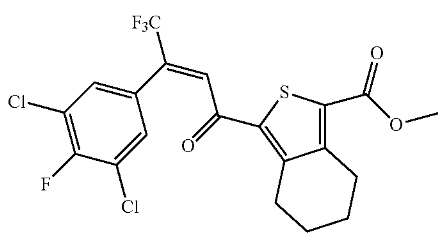 [SMILES: COC(=O)c1sc(C(=O)/C=C(\c2cc(Cl)c(F)c(Cl)c2)C(F)(F)F)c2c1CCCC2] | MS (m/z): 481 (M + 1). |
| 16 | 3-[4,4,4-Trifluoro-3-(3,4,5-trichloro-phenyl)-but-2-enoyl]-5,6-dihydro-4H-cyclopenta[c]thiophene-1-carboxylic acid methyl ester | 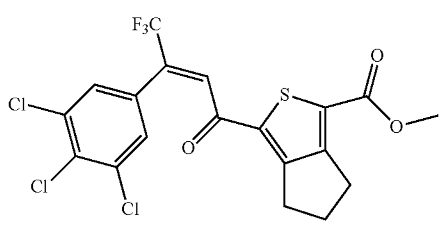 [SMILES: COC(=O)c1sc(C(=O)/C=C(\c2cc(Cl)c(Cl)c(Cl)c2)C(F)(F)F)c2c1CCC2] | MS (m/z): 483 (M + 1). |
| 17 | 3-[3-(3,5-Dichloro-4-fluoro-phenyl)-4,4,4-trifluoro-but-2-enoyl]-5,6-dihydro-4H-cyclopenta[c]thiophene-1-carboxylic acid methyl ester | 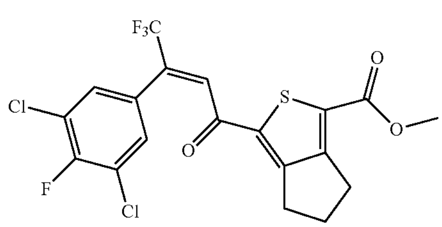 [SMILES: COC(=O)c1sc(C(=O)/C=C(\c2cc(Cl)c(F)c(Cl)c2)C(F)(F)F)c2c1CCC2] | MS (m/z): 467 (M + 1). |

Preparation 18

3-[5-(3,5-Dichloro-phenyl)-5-trifluoromethyl-4,5-dihydro-isoxazol-3-yl]-4,5,6,7-tetrahydro-benzo[c]thiophene-1-carboxylic acid methyl ester

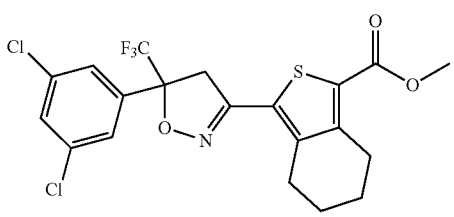 [SMILES: COC(=O)c1sc(C2=NOC(c3cc(Cl)cc(Cl)c3)(C(F)(F)F)C2)c2c1CCCC2]

Stir a mixture of 3-[3-(3,5-Dichloro-phenyl)-4,4,4-trifluoro-but-2-enoyl]-4,5,6,7-tetrahydro-benzo[c]thiophene-1-carboxylic acid methyl ester (8.75 g, 18.9 mmol), NaOH (2.65 g, 66.1 mmol) and $NH_2OH$—HCl (2.6 g, 37.8 mmol) in MeOH (60 mL) and water (15 mL) at room temperature for 2.5 hour. After removal of solvent under vacuum, dilute the residue with ice water (50 mL). Acidify the aqueous mixture with conc. HCl to pH=1 and extract the resultant mixture with EtOAc (50 mL×3). The combined organic layers are washed with brine, dried over anhydrous $Na_2SO_4$ and concentrated under vacuum. Purify the residue by silica gel chromatograph (PE:EtOAc 50:1) to afford 3-[5-(3,5-Dichloro-phenyl)-5-trifluoromethyl-4,5-dihydro-isoxazol-3-yl]-4,5,6,7-tetrahydro-benzo[c]thiophene-1-carboxylic acid methyl ester as an orange solid (8.1 g, 93.1%). MS (m/z): 478 (M+1).

The following compounds are prepared essentially by the method of Preparation 18.

| Prep. No. | Chemical name | Structure | Physical data |
|---|---|---|---|
| 19 | 3-[5-(3,5-Dichloro-phenyl)-5-trifluoromethyl-4,5-dihydro-isoxazol-3-yl]-5,6-dihydro-4H-cyclopenta[c]thiophene-1-carboxylic acid methyl ester | 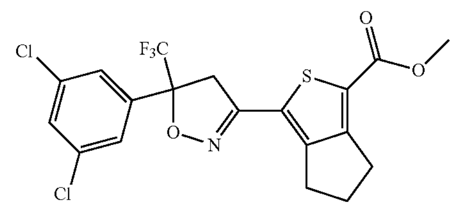 [SMILES: COC(=O)c1sc(C2=NOC(c3cc(Cl)cc(Cl)c3)(C(F)(F)F)C2)c2c1CCC2] | MS (m/z): 464 (M + 1). |
| 20 | 3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid methyl ester | 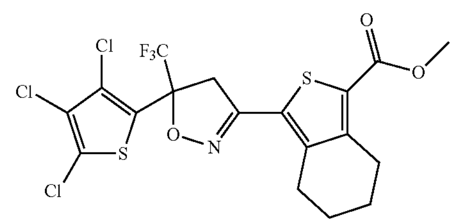 [SMILES: COC(=O)c1sc(C2=NOC(c3sc(Cl)c(Cl)c3Cl)(C(F)(F)F)C2)c2c1CCCC2] | MS (m/z): 516 (M − 1). |
| 21 | 3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid methyl ester | 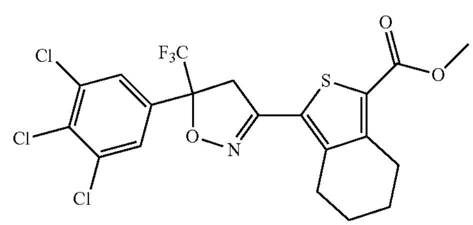 [SMILES: COC(=O)c1sc(C2=NOC(c3cc(Cl)c(Cl)c(Cl)c3)(C(F)(F)F)C2)c2c1CCCC2] | MS (m/z): 512 (M + 1). |
| 22 | 3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid methyl ester | 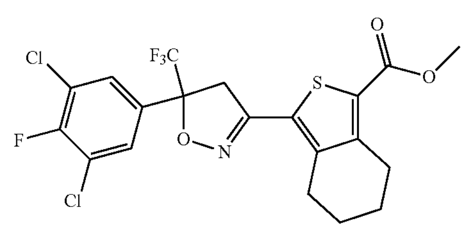 [SMILES: COC(=O)c1sc(C2=NOC(c3cc(Cl)c(F)c(Cl)c3)(C(F)(F)F)C2)c2c1CCCC2] | MS (m/z): 496 (M + 1). |
| 23 | 3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid methyl ester | 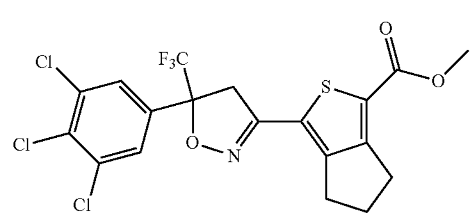 [SMILES: COC(=O)c1sc(C2=NOC(c3cc(Cl)c(Cl)c(Cl)c3)(C(F)(F)F)C2)c2c1CCC2] | MS (m/z): 498 (M + 1). |

| Prep. No. | Chemical name | Structure | Physical data |
|---|---|---|---|
| 24 | 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid methyl ester | 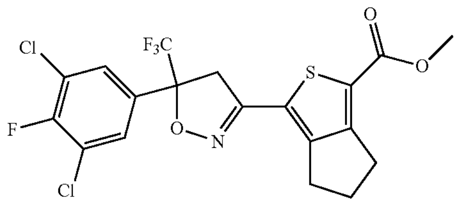 [SMILES: COC(=O)c1sc(C2=NOC(c3cc(Cl)c(F)c(Cl)c3)(C(F)(F)F)C2)c2c1CCC2] | MS (m/z): 482 (M + 1). |

Preparation 25

3-[5-(3,5-Dichloro-phenyl)-5-trifluoromethyl-4,5-dihydro-isoxazol-3-yl]-4,5,6,7-tetrahydro-benzo[c]thiophene-1-carboxylic acid

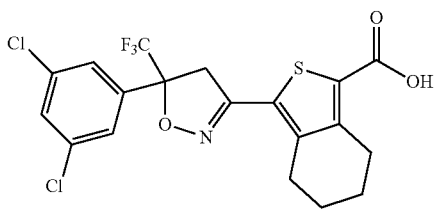 [SMILES: O=C(O)c1sc(C2=NOC(c3cc(Cl)cc(Cl)c3)(C(F)(F)F)C2)c2c1CCCC2]

Stir a mixture of 3-[5-(3,5-Dichloro-phenyl)-5-trifluoromethyl-4,5-dihydro-isoxazol-3-yl]-4,5,6,7-tetrahydro-benzo[c]thiophene-1-carboxylic acid methyl ester (8.1 g, 17.0 mmol) and LiOH—$H_2O$ (3.57 g, 84.9 mmol) in MeOH (64 mL) and water (16 mL) at room temperature overnight. After removal of organic solvent under vacuum, dilute the residue with ice water (80 mL). Acidify the aqueous mixture with conc. HCl to pH=1, and extract the resultant mixture with EtOAc (100 mL×3). The combined organic layers are washed brine, dried over anhydrous $Na_2SO_4$ and concentrated under vacuum. Purify the residue by silica gel chromatograph (PE: EtOAc 1:1) to afford 3-[5-(3,5-Dichloro-phenyl)-5-trifluoromethyl-4,5-dihydro-isoxazol-3-yl]-4,5,6,7-tetrahydro-benzo[c]thiophene-1-carboxylic acid as pale yellow solid (6.8 g, 86.4%). MS (m/z): 464 (M+1).

The following compounds may be prepared essentially by the method of Preparation 25.

| Prep. No. | Chemical name | Structure | Physical data |
|---|---|---|---|
| 26 | 3-[5-(3,5-Dichloro-phenyl)-5-trifluoromethyl-4,5-dihydro-isoxazol-3-yl]-5,6-dihydro-4H-cyclopenta[c]thiophene-1-carboxylic acid | 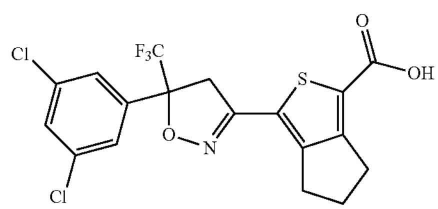 [SMILES: O=C(O)c1sc(C2=NOC(c3cc(Cl)cc(Cl)c3)(C(F)(F)F)C2)c2c1CCC2] | MS (m/z): 448 (M − 1). |
| 27 | 3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid | 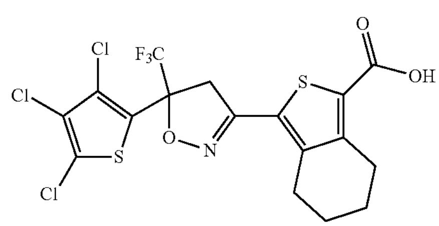 [SMILES: O=C(O)c1sc(C2=NOC(c3sc(Cl)c(Cl)c3Cl)(C(F)(F)F)C2)c2c1CCCC2] | MS (m/z): 502 (M − 1). |
| 28 | 3-[5-(3,4,5-Trichloro-phenyl)-5-trifluoromethyl-4,5-dihydro-isoxazol-3-yl]-4,5,6,7-tetrahydro-benzo[c]thiophene-1-carboxylic acid | 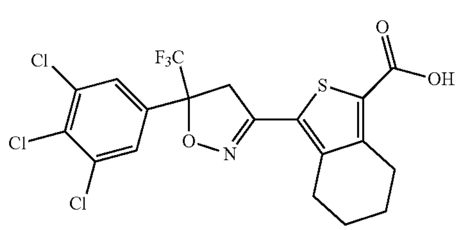 [SMILES: O=C(O)c1sc(C2=NOC(c3cc(Cl)c(Cl)c(Cl)c3)(C(F)(F)F)C2)c2c1CCCC2] | MS (m/z): 496 (M − 1). |

| Prep. No. | Chemical name | Structure | Physical data |
|---|---|---|---|
| 29 | 3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid | 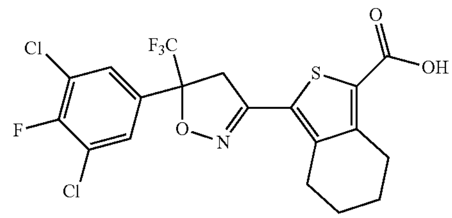 [SMILES: O=C(O)c1sc(C2=NOC(c3cc(Cl)c(F)c(Cl)c3)(C(F)(F)F)C2)c2c1CCCC2] | MS (m/z): 480 (M − 1). |
| 30 | 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid | 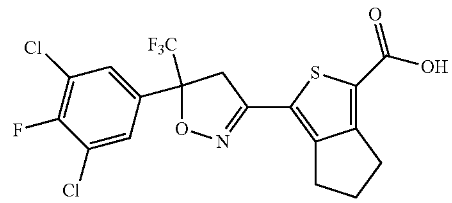 [SMILES: O=C(O)c1sc(C2=NOC(c3cc(Cl)c(F)c(Cl)c3)(C(F)(F)F)C2)c2c1CCC2] | MS (m/z): 466 (M − 1). |
| 31 | 3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid | 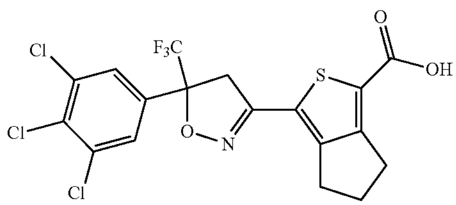 [SMILES: O=C(O)c1sc(C2=NOC(c3cc(Cl)c(Cl)c(Cl)c3)(C(F)(F)F)C2)c2c1CCC2] | MS (m/z): 482 (M − 1). |

Example 32

3-(5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide

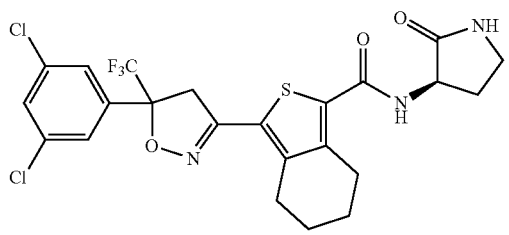 [SMILES: O=C(N[C@@H]1CCNC1=O)c1sc(C2=NOC(c3cc(Cl)cc(Cl)c3)(C(F)(F)F)C2)c2c1CCCC2]

Stir a mixture of 3-[5-(3,5-Dichloro-phenyl)-5-trifluoromethyl-4,5-dihydro-isoxazol-3-yl]-4,5,6,7-tetrahydro-benzo[c]thiophene-1-carboxylic acid (850 mg, 1.84 mmol), HATU (837 mg, 2.20 mmol) and DIEA (539 mg, 0.8 mL, 4.6 mmol) in DCM (8 mL) at room temperature for 15 min, followed by addition of (R)-3-aminopyrrolidin-2-one hydrochloride (315 mg, 2.76 mmol). Stir the reaction mixture at room temperature for additional 1.5 hour. Dilute the reaction mixture with water (20 mL) and extract with DCM (20 mL×3). The combined organic layers are washed brine, dried over anhydrous $Na_2SO_4$ and concentrated under vacuum. Purify the residue by preparative HPLC to afford 3-(5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide as a white solid (730 mg, 73.0%). MS (m/z): 546 (M+1); $^1$H NMR (400 MHz, CDCl$_3$) δ 7.52-7.46 (m, 3H), 6.49 (s, 1H), 5.83 (s, 1H), 4.51-4.48 (m, 1H), 4.22 (d, J=17.2, 1H), 3.85 (d, J=17.2, 1H), 3.52-3.47 (m, 2H), 3.09-2.87 (m, 5H), 2.12-2.03 (m, 1H), 1.89-1.73 (m, 4H).

The following compounds may be prepared essentially by the method of Example 32.

| Ex. No. | Chemical name | Structure | Physical data |
|---|---|---|---|
| 33 | N,N-Dimethyl-2-(4-{3-[5-(3,4,5-trichloro-thiophen-2-yl)-5-trifluoro-methyl-4,5-dihydro-isoxazol-3-yl]-4,5,6,7-tetrahydro-benzo[c]thiophene-1-carbonyl}-piperazin-1-yl)-acetamide | 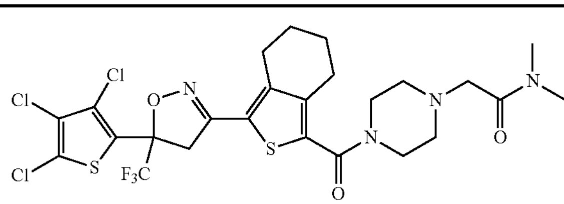 | MS (m/z): 659 (M + 1); $^1$H NMR (400 MHz, CDCl$_3$) δ 4.07-4.02 (m, 2H), 3.68-3.80 (m, 4H), 3.49-3.41 (m, 2H), 3.09-3.01 (s, 3H), 3.01-2.95 (s, 3H), 2.91-2.85 (m, 2H), 2.84-2.78 (m, 4H), 2.69-2.63 (m, 2H), 1.87-1.72 (m, 4H). |

| Ex. No. | Chemical name | Structure | Physical data |
|---|---|---|---|
| Prep No. 34 | ({3-[5-(3,5-Dichloro-phenyl)-5-trifluoro-methyl-4,5-dihydro-isoxazol-3-yl]-4,5,6,7-tetrahydro-benzo[c]thiophene-1-carbonyl}-amino)-acetic acid methyl ester | 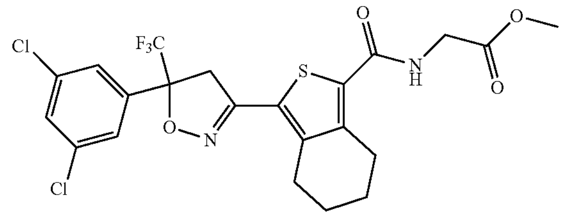 [SMILES: COC(=O)CNC(=O)c1sc(C2=NOC(c3cc(Cl)cc(Cl)c3)(C(F)(F)F)C2)c2c1CCCC2] | MS (m/z): 535 (M + 1). |
| Prep No. 35 | ({3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl}-amino)-acetic acid methyl ester | 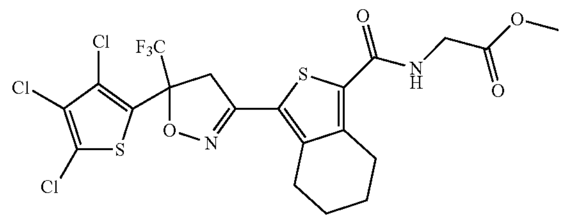 [SMILES: COC(=O)CNC(=O)c1sc(C2=NOC(c3sc(Cl)c(Cl)c3Cl)(C(F)(F)F)C2)c2c1CCCC2] | MS (m/z): 575 (M + 1). |
| 36 | 3-(5-(3,5-dichloro-phenyl)-5-(trifluoro-methyl)-4,5-dihydro-isoxazol-3-yl)-N-(2-oxo-2-(2,2,2-trifluoroethylamino)ethyl)-5,6-dihydro-4H-cyclopenta[c]thiophene-1-carboxamide | 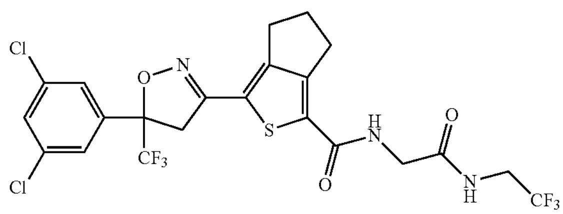 [SMILES: O=C(CNC(=O)c1sc(C2=NOC(c3cc(Cl)cc(Cl)c3)(C(F)(F)F)C2)c2c1CCC2)NCC(F)(F)F] | MS (m/z): 588 (M + 1); $^1$H NMR (400 MHz, CDCl$_3$) δ7.52-7.48 (m, 2H), 7.48-7.44 (m, 1H), 7.01-6.95 (s, 1H), 6.79-6.71 (s, 1H), 4.21-4.18 (m, 2H), 4.06-3.91 (m, 3H), 3.65-3.59 (d, J = 17.2, 1H), 2.98-2.87 (m, 4H), 2.59-2.49 (m, 2H). |
| 37 | 3-[5-(3,5-Dichloro-phenyl)-5-trifluoro-methyl-4,5-dihydro-isoxazol-3-yl]-4,5,6,7-tetrahydro-benzo[c]thiophene-1-carboxylic acid (1,1-dioxo-thietan-3-yl)-amide | 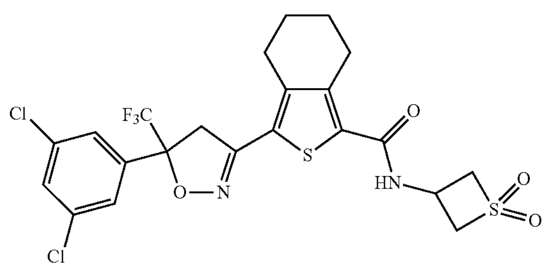 [SMILES: O=C(NC1CS(=O)(=O)C1)c1sc(C2=NOC(c3cc(Cl)cc(Cl)c3)(C(F)(F)F)C2)c2c1CCCC2] | MS (m/z): 567 (M + 1); $^1$H NMR (400 MHz, CDCl$_3$) δ 7.48 (s, 2H), 7.44 (s, 1H), 6.59-6.58 (s, 1H), 4.91-4.89 (m, 1H), 4.64-4.59 (m, 2H), 4.07-4.03 (m, 3H), 3.70-3.65 (m, 1H), 2.97-2.91 (m, 4H), 1.80-1.86 (m, 4H). |
| 38 | 3-(5-(3,5-dichloro-phenyl)-5-(trifluoro-methyl)-4,5-dihydro-isoxazol-3-yl)-N-(3-oxocyclohexyl)-4,5,6,7-tetrahydrobenzo[c]thiophene-1-carboxamide | 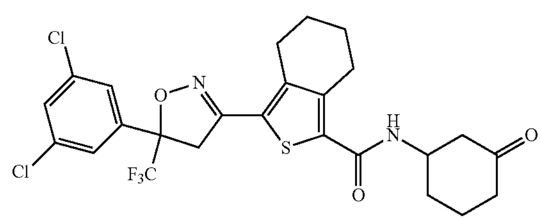 [SMILES: O=C1CCCC(NC(=O)c2sc(C3=NOC(c4cc(Cl)cc(Cl)c4)(C(F)(F)F)C3)c3c2CCCC3)C1] | MS (m/z): 559 (M + 1); $^1$H NMR (400 MHz, CDCl$_3$) δ7.48 (s, 2H), 7.43 (s, 1H), 5.73 (d, J = 1.6 Hz, 1H), 4.46- 4.42 (m, 1H), 4.06-4.02 (d, J = 16 Hz, 1H), 3.68-3.64 (d, J = 16 Hz, 1H), 2.93-2.89 (m, 4H), 2.82-2.77 (m, 1H), 2.47- 2.30 (m, 3H), 2.17-2.15 (m, 1H), 2.02-1.95 (m, 1H), 1.88-1.78 (m, 6H). |
| 39 | 3-[5-(3,5-Dichloro-phenyl)-5-trifluoro-methyl-4,5-dihydro-isoxazol-3-yl]-4,5,6,7-tetrahydro-benzo[c]thiophene-1-carboxylic acid (1,1-dioxo-hexahydro-1l6-thiopyran-4-yl)-amide | 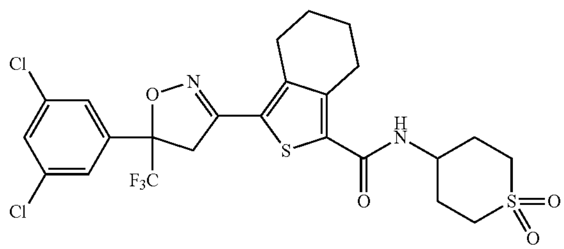 [SMILES: O=C(NC1CCS(=O)(=O)CC1)c1sc(C2=NOC(c3cc(Cl)cc(Cl)c3)(C(F)(F)F)C2)c2c1CCCC2] | MS (m/z): 559 (M + 1); $^1$H NMR (400 MHz, CDCl$_3$) δ 7.49-7.44 (m, 3H), 5.77 (d, J = 7.6 Hz, 1H), 4.27-4.10 (m, 1H), 4.04 (d, J = 17.2 Hz, 1H), 3.66 (d, J = 17.2 Hz, 1H), 3.20-3.05 (m, 4H), 2.94-2.86 (m, 4H), 2.42-2.40 (m, 2H), 2.26-2.16 (m, 2H), 1.79-1.74 (m, 4H). |

-continued

| Ex. No. | Chemical name | Structure | Physical data |
|---|---|---|---|
| 40 | 3-[5-(3,5-Dichloro-phenyl)-5-trifluoro-methyl-4,5-dihydro-isoxazol-3-yl]-4,5,6,7-tetrahydro-benzo[c]thiophene-1-carboxylic acid [2-oxo-1-(2,2,2-trifluoro-ethyl)-pyrrolidin-3-yl]-amide | 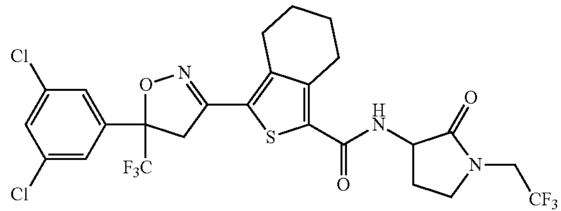 [SMILES: O=C(NC1CCN(CC(F)(F)F)C1=O)c1sc(C2=NOC(c3cc(Cl)cc(Cl)c3)(C(F)(F)F)C2)c2c1CCCC2] | MS (m/z): 628 (M + 1); $^1$H NMR (400 MHz, CDCl$_3$) δ 7.52-7.43 (m, 3H), 6.65-6.56 (m, 1H), 4.61-4.51 (m, 1H), 4.18-4.01 (m, 2H), 3.99-3.51 (m, 4H), 3.09-2.81 (m, 5H), 2.11-1.99 (m, 1H), 1.81-1.72 (m, 4H). |
| 41 | 3-(5-(3,5-dichloro-phenyl)-5-(trifluoro-methyl)-4,5-dihydro-isoxazol-3-yl)-N-((R)-2-oxopyrrolidin-3-yl)-5,6-dihydro-4H-cyclopenta[c]thiophene-1-carboxamide | 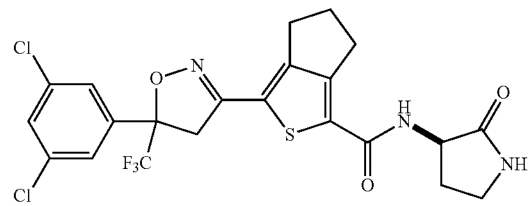 | MS (m/z): 532 (M + 1); $^1$H NMR (400 MHz, CDCl$_3$) δ 7.52-7.48 (m, 2H), 7.48-7.44 (m, 1H), 6.59-6.50 (s, 1H), 6.14-6.08 (s, 1H), 4.48-4.41 (m, 1H), 4.06-3.94 (d, J = 17.2, 1H), 3.65-3.59 (d, J = 17.2, 1H), 3.51-3.42 (m, 2H), 3.07-2.84 (m, 5H), 2.58-2.48 (m, 2H), 2.11-2.01 (m, 1H). |
| 42 | N-(2-(cyanomethyl-amino)-2-oxoethyl)-3-(5-(3,5-dichlorophenyl)-5-(trifluoromethyl)-4,5-dihydroisoxazol-3-yl)-5,6-dihydro-4H-cyclopenta[c]thiophene-1-carboxamide | 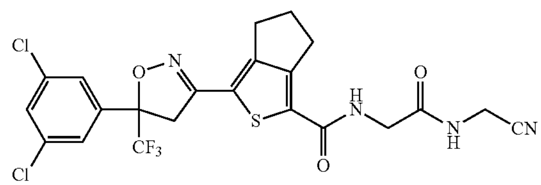 [SMILES: N#CCNC(=O)CNC(=O)c1sc(C2=NOC(c3cc(Cl)cc(Cl)c3)(C(F)(F)F)C2)c2c1CCC2] | MS (m/z): 545 (M + 1); $^1$H NMR (400 MHz, CDCl$_3$) δ 7.58-7.52 (s, 1H), 7.52-7.48 (m, 2H), 7.48-7.44 (m, 1H), 6.86-6.78 (s, 1H), 4.26-4.19 (m, 4H), 4.04-3.97 (d, J = 17.2, 1H), 3.65-3.59 (d, J = 17.2, 1H), 3.09-2.84 (m, 4H), 2.58-2.48 (m, 2H). |
| 43 | 3-(5-(3,5-dichloro-phenyl)-5-(trifluoro-methyl)-4,5-dihydro-isoxazol-3-yl)-N-(2-oxo-2-(prop-2-ynylamino)ethyl)-5,6-dihydro-4H-cyclopenta[c]thiophene-1-carboxamide | 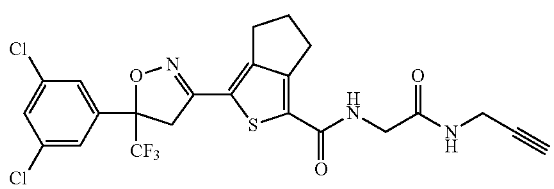 [SMILES: C#CCNC(=O)CNC(=O)c1sc(C2=NOC(c3cc(Cl)cc(Cl)c3)(C(F)(F)F)C2)c2c1CCC2] | MS (m/z): 544 (M + 1); $^1$H NMR (400 MHz, CDCl$_3$) δ 7.52-7.48 (m, 2H), 7.48-7.44 (m, 1H), 6.86-6.68 (m, 2H), 4.19-4.05 (m, 4H), 4.04-3.97 (d, J = 17.2, 1H), 3.65-3.59 (d, J = 17.2, 1H), 3.03-2.87 (m, 4H), 2.58-2.48 (m, 2H), 2.29-2.26 (s, 1H). |
| 44 | N-(2-oxo-2-(2,2,2-trifluoroethylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide | 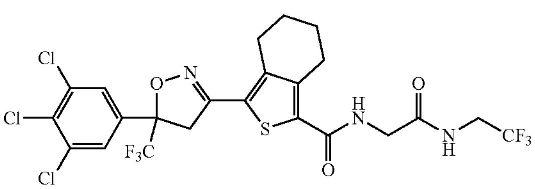 [SMILES: O=C(CNC(=O)c1sc(C2=NOC(c3cc(Cl)c(Cl)c(Cl)c3)(C(F)(F)F)C2)c2c1CCCC2)NCC(F)(F)F] | MS (m/z): 636 (M + 1); $^1$H NMR (400 MHz, CDCl$_3$) δ 7.62 (s, 2H), 7.32 (br, 1H), 6.95 (br, 1H), 4.26-4.25 (m, 2H), 4.06-3.83 (m, 3H), 3.66 (d, J = 16.8 Hz, 1H), 2.98-2.89 (m, 4H), 1.79 (br, 4H). |
| 45 | N-((R)-2-oxopyrrolidin-3-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide | 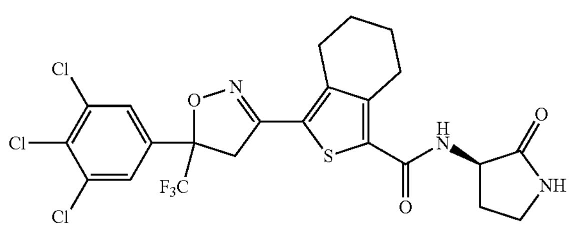 [SMILES: O=C(N[C@@H]1CCNC1=O)c1sc(C2=NOC(c3cc(Cl)c(Cl)c(Cl)c3)(C(F)(F)F)C2)c2c1CCCC2] | MS (m/z): 580 (M + 1); $^1$H NMR (400 MHz, CDCl$_3$) δ 7.62 (s, 2H), 6.62 (br, 1H), 6.17 (br, 1H), 4.47-4.46 (m, 1H), 4.07-4.02 (m, 1H), 3.75-3.64 (m, 1H), 3.49-3.43 (m, 2H), 3.02-2.88 (m, 2H), 2.09-2.01 (m, 1H), 1.77 (br, 4H). |
| 46 | N-(2-(cyanomethyl-amino)-2-oxoethyl)-3-(5-(3,4,5-trichloro-phenyl)-5-(trifluoro-methyl)-4,5-dihydro-isoxazol-3-yl)-4,5,6,7-tetrahydrobenzo[c]thiophene-1-carboxamide | 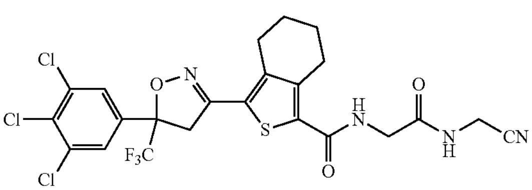 [SMILES: N#CCNC(=O)CNC(=O)c1sc(C2=NOC(c3cc(Cl)c(Cl)c(Cl)c3)(C(F)(F)F)C2)c2c1CCCC2] | MS (m/z): 593 (M + 1); $^1$H NMR (CDCl$_3$, 400 MHz) δ 7.63 (s, 2 H), 7.47 (m, 1 H), 6.81 (m, 1 H), 4.22 (m, 4 H), 4.06 (d, J = 17.2, 1 H), 3.70 (d, J = 17.2, 1 H), 2.90 (m, 4 H), 1.79 (m, 4 H). |

| Ex. No. | Chemical name | Physical data |
|---|---|---|
| 47 | N-(2-oxo-2-(prop-2-ynylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide | MS (m/z): 592 (M + 1). $^1$H NMR (CDCl3, 400 MHz) δ 7.63 (s, 2 H), 6.78 (m, 1 H), 6.50 (m, 1 H), 4.15 (m, 2 H), 4.10 (m, 2 H), 4.05 (d, J = 16.8, 1 H), 3.67 (d, J = 16.8, 1 H), 2.95 (m, 2 H), 2.90 (m, 2 H), 2.26 (m, 1 H), 1.79 (m, 4H). |
| 48 | 3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-4,5,6,7-tetrahydrobenzo[c]thiophene-1-carboxamide | MS (m/z): 620 (M + 1); $^1$H NMR (CDOD$_3$, 400 MHz) δ 7.76 (d, J = 6.4, 2H), 4.25 (d, J = 17.6, 1H), 4.07 (s, 2H), 4.04-3.92 (m, 3H), 3.01-2.98 (m, 2H), 2.90-2.89 (m, 2H), 1.79 (m, 4H). |
| 49 | 3-(5-(3,5-dichloro-4-fluorophenyl)-5-(trifluoromethyl)-4,5-dihydroisoxazol-3-yl)-N-((R)-2-oxopyrrolidin-3-yl)-4,5,6,7-tetrahydrobenzo[c]thiophene-1-carboxamide | MS (m/z): 564 (M + 1); $^1$H NMR (CDOD$_3$, 400 MHz) δ 7.76 (d, J = 6.4, 2H), 4.63 (t, J = 9.6, 1H), 4.24 (d, J = 17.6, 1H), 4.02 (d, J = 17.6, 1H), 3.44-3.40 (m, 2H), 2.99-2.98 (m, 2H), 2.89 (m, 2H), 2.59-2.52 (m, 1H), 2.23-2.18 (m, 1H), 1.79-1.77 (m, 4H). |
| 50 | N-(2-(cyanomethylamino)-2-oxoethyl)-3-(5-(3,5-dichloro-4-fluorophenyl)-5-(trifluoromethyl)-4,5-dihydroisoxazol-3-yl)-4,5,6,7-tetrahydrobenzo[c]thiophene-1-carboxamide | MS (m/z): 577 (M + 1); $^1$H NMR (CDOD$_3$, 400 MHz) δ 7.77 (d, J = 6.4, 2H), 4.28-4.21 (m, 3H), 4.05-4.00 (m, 3H), 3.00 (t, J = 6.0, 2H), 2.93-2.90 (m, 2H), 1.81-1.80 (m, 4H). |
| 51 | 3-(5-(3,5-dichloro-4-fluorophenyl)-5-(trifluoromethyl)-4,5-dihydroisoxazol-3-yl)-N-(2-oxo-2-(prop-2-ynylamino)ethyl)-4,5,6,7-tetrahydrobenzo[c]thiophene-1-carboxamide | MS (m/z): 576 (M + 1); $^1$H NMR (CDOD$_3$, 400 MHz) δ 7.76 (d, J = 6.4, 2H), 4.24 (d, J = 17.6, 1H), 4.03-3.99 (m, 5H), 2.98 (t, J = 6.0, 2H), 2.88-2.86 (m, 2H), 2.62 (t, J = 2.4, 1H), 1.79-1.77 (m, 4H). |
| 52 | N-(2-oxo-2-(2,2,2-trifluoroethylamino)ethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide | MS (m/z): 622 (M + 1); $^1$H NMR (CDCl3, 400 MHz) δ 7.64 (s, 2 H), 6.81 (brs, 1 H), 6.73 (brs, 1 H), 4.22 (d, J = 4.8, 2 H), 3.99 (m, 3 H), 3.64 (d, J = 17.2, 1 H), 2.99 (t, J = 7.6, 2 H), 2.91 (t, J = 7.6, 2 H), 2.55 (m, 2 H). |
| 53 | N-((R)-2-oxopyrrolidin-3-yl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide | MS (m/z): 566 (M + 1); $^1$H NMR (CDCl3, 400 MHz) δ 7.62 (s, 2 H), 6.46 (brs, 1 H), 6.16 (brs, 1 H), 4.47 (m, 1 H), 3.99 (d, J = 17.2, 1 H), 3.61 (d, J = 17.2, 1 H), 3.47 (m, 2 H), 2.93 (m, 5 H), 2.53 (m, 2 H), 2.09 (m, 1 H). |

| Ex. No. | Chemical name | Structure | Physical data |
|---|---|---|---|
| 54 | N-(2-(cyanomethyl-amino)-2-oxoethyl)-3-(5-(3,4,5-trichloro-phenyl)-5-(trifluoro-methyl)-4,5-dihydro-isoxazol-3-yl)-5,6-dihydro-4H-cyclo-penta[c]thiophene-1-carboxamide | 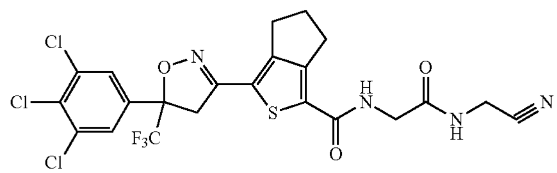 [SMILES: N#CCNC(=O)CNC(=O)c1sc(C2=NOC(c3cc(Cl)c(Cl)c(Cl)c3)(C(F)(F)F)C2)c2c1CCC2] | MS (m/z): 579 (M + 1); $^1$H NMR (CDCl3, 400 MHz) δ 7.62 (s, 2 H), 7.21 (brs, 1 H), 6.71 (brs, 1 H), 4.22 (d, J = 6.0, 2 H), 4.18 (d, J = 5.2, 2H), 4.02 (d, J = 17.2, 1 H), 3.63 (d, J = 17.2, 1 H), 2.96 (t, J = 7.2, 2 H), 2.89 (t, J = 7.2, 2 H), 2.56 (m, 2 H). |
| 55 | N-(2-oxo-2-(prop-2-yn ylamino)ethyl)-3-(5-(3,4,5-trichlorophenyl)-5-(trifluoromethyl)-4,5-dihydroisoxazol-3-yl)-5,6-dihydro-4H-cyclo-penta[c]thiophene-1-carboxamide | 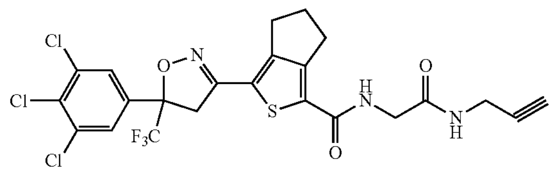 [SMILES: C#CCNC(=O)CNC(=O)c1sc(C2=NOC(c3cc(Cl)c(Cl)c(Cl)c3)(C(F)(F)F)C2)c2c1CCC2] | MS (m/z): 578 (M + 1); $^1$H NMR (CDCl3, 400 MHz) δ 7.62 (s, 2 H), 6.82 (brs, 1 H), 6.65 (brs, 1 H), 4.15 (d, J = 4.8, 2 H), 4.10 (d, $J_1$ = 2.4, $J_2$ = 4.2, 2 H), 4.02 (d, J = 16.8, 1 H), 3.62 (d, J = 16.8, 1 H), 2.98 (t, J = 7.2, 2 H), 2.88 (t, J = 7.2, 2 H), 2.55 (m, 2 H), 2.27 (t, J = 2.4, 2 H). |
| 56 | N-(2-oxo-1-(2,2,2-trifluoroethyl)pyrrolidin-3-yl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide | 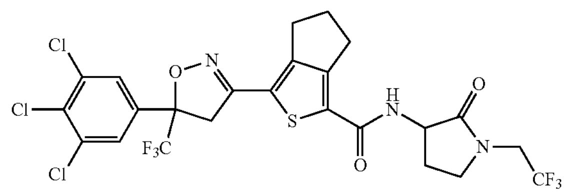 [SMILES: O=C(NC1CCN(CC(F)(F)F)C1=O)c1sc(C2=NOC(c3cc(Cl)c(Cl)c(Cl)c3)(C(F)(F)F)C2)c2c1CCC2] | MS (m/z): 648 (M + 1); $^1$H NMR (CDCl3, 400 MHz) δ 7.62 (s, 2 H), 6.5 (brs, 1 H), 4.50 (m, 1 H), 4.09 (m, 1 H), 4.00 (d, J = 17.2, 1 H), 3.84 (m, 1 H), 3.58 (m, 3 H), 2.93 (m, 5 H), 2.52 (m, 2 H), 2.04 (m, 1 H). |
| 57 | 3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide | 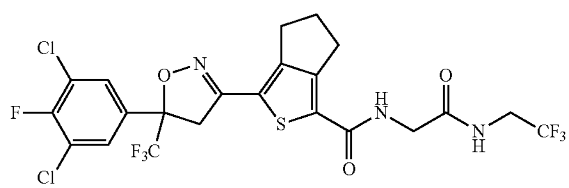 [SMILES: O=C(CNC(=O)c1sc(C2=NOC(c3cc(Cl)c(F)c(Cl)c3)(C(F)(F)F)C2)c2c1CCC2)NCC(F)(F)F] | MS (m/z): 606 (M + 1); $^1$H NMR (CDCl3, 400 MHz) δ 7.56 (d, J = 6.0, 2 H), 6.92 (t, J = 6.4, 1 H), 6.76 (t, J = 4.8, 1 H), 4.21 (d, J = 4.8, 1 H), 3.98 (m, 3 H), 3.61 (d, J = 16.8, 1 H), 2.97 (t, J = 7.6, 2 H), 2.89 (t, J = 7.6, 2 H), 2.55 (m, 2H) |
| 58 | 3-(5-(3,5-dichloro-4-fluorophenyl)-5-(trifluoromethyl)-4,5-dihydroisoxazol-3-yl)-N-((R)-2-oxopyrrolidin-3-yl)-5,6-dihydro-4H-cyclopenta[c]thiophene-1-carboxamide | 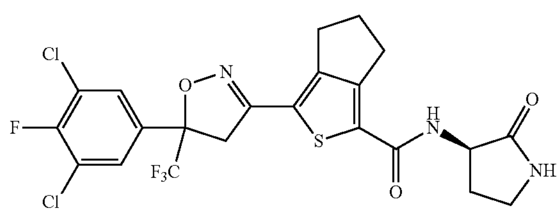 [SMILES: O=C(N[C@@H]1CCNC1=O)c1sc(C2=NOC(c3cc(Cl)c(F)c(Cl)c3)(C(F)(F)F)C2)c2c1CCC2] | MS (m/z): 550 (M + 1); $^1$H NMR (CDCl3, 400 MHz) δ 7.56 (d, J = 6.4, 2 H), 6.46 (brs, 1 H), 6.32 (brs, 1 H), 4.47 (m, 1 H), 3.99 (d, J = 17.2, 1 H), 3.61 (d, J = 17.2, 1 H), 3.48 (m, 2 H), 2.93 (m, 5 H), 2.53 (m, 2 H), 2.06 (m, 1 H). |
| 59 | N-(2-(cyanomethyl-amino)-2-oxoethyl)-3-(5-(3,5-dichloro-4-fluorophenyl)-5-(trifluoromethyl)-4,5-dihydroisoxazol-3-yl)-5,6-dihydro-4H-cyclopenta[c]thiophene-1-carboxamide | 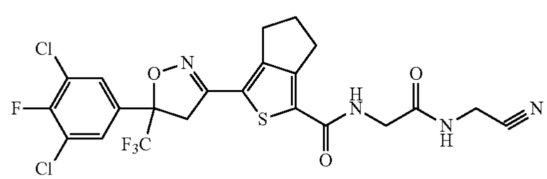 [SMILES: N#CCNC(=O)CNC(=O)c1sc(C2=NOC(c3cc(Cl)c(F)c(Cl)c3)(C(F)(F)F)C2)c2c1CCC2] | MS (m/z): 563 (M + 1); $^1$H NMR (CDCl3, 400 MHz) δ 7.56 (d, J = 6.0, 2 H), 7.41 (brs, 1 H), 6.84 (brs, 1 H), 4.20 (m, 4 H), 3.99 (d, J = 16.8, 1 H), 3.63 (d, J = 16.8, 1 H), 2.95 (t, J = 7.2, 2 H), 2.88 (t, J = 7.2, 2 H), 2.53 (m, 2 H). |
| 60 | 3-(5-(3,5-dichloro-4-fluorophenyl)-5-(trifluoromethyl)-4,5-dihydroisoxazol-3-yl)-N-(2-oxo-1-(2,2,2-trifluoroethyl)pyrrolidin-3-yl)-5,6-dihydro-4H-cyclopenta[c]thiophene-1-carboxamide | 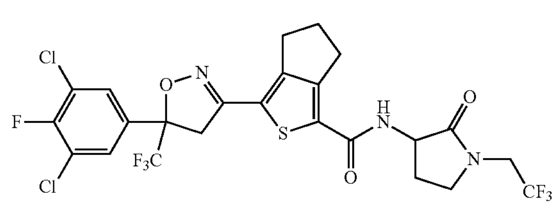 [SMILES: O=C(NC1CCN(CC(F)(F)F)C1=O)c1sc(C2=NOC(c3cc(Cl)c(F)c(Cl)c3)(C(F)(F)F)C2)c2c1CCC2] | MS (m/z): 632 (M + 1); $^1$H NMR (CDCl3, 400 MHz) δ 7.58 (d, J = 6.0, 2H), 6.60-6.57 (m, 1H), 4.56-4.50 (m, 1H), 4.14-4.00 (m, 2H), 3.87-3.83 (m, 1H), 3.67-3.55 (m, 3H), 3.01-2.86 (m, 5H), 2.57-2.50 (m, 2H), 2.10-2.05 (m, 1H). |

| Ex. No. | Chemical name | Structure | Physical data |
|---|---|---|---|
| 61 | 3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide | 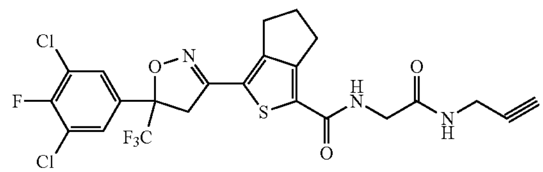 [SMILES: C#CCNC(=O)CNC(=O)c1sc(C2=NOC(c3cc(Cl)c(F)c(Cl)c3)(C(F)(F)F)C2)c2c1CCC2] | MS (m/z): 562 (M + 1); $^1$H NMR (CDCl3, 400 MHz) δ 7.58 (d, J = 6.0, 2H), 6.85 (brs, 1H), 6.70 (brs, 1H), 4.18 (d, J = 4.8, 2H), 4.14-4.12 (m, 2H), 4.04 (d, J = 17.2, 1H), 3.65 (d, J = 17.2, 1H), 3.00 (t, J = 7.2, 2H), 2.90 (t, J = 7.2, 2H), 2.60-2.55 (m, 2H), 2.29 (s, 1H). |
| 62 | 3-(5-(3,5-dichlorophenyl)-5-(trifluoromethyl)-4,5-dihydroisoxazol-3-yl)-N-(2-oxo-2-(2,2,2-trifluoroethylamino)ethyl)-4,5,6,7-tetrahydrobenzo[c]thiophene-1-carboxamide | 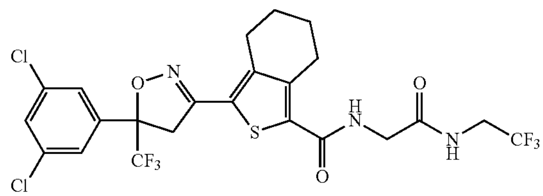 [SMILES: O=C(CNC(=O)c1sc(C2=NOC(c3cc(Cl)cc(Cl)c3)(C(F)(F)F)C2)c2c1CCCC2)NCC(F)(F)F] | MS (m/z): 602 (M + 1); 1H NMR (CDCl3, 400 MHz) δ 7.52-7.46 (m, 3H), 7.12-7.01 (m, 1H), 6.85-6.78 (m, 1H), 4.28-4.20 (m, 2H), 4.08-3.91 (m, 3H), 3.68 (d, J = 17.2, 1H), 3.07-2.87 (m, 4H), 1.89-1.73 (m, 4H). |
| 63 | 3-(5-(3,5-dichlorophenyl)-5-(trifluoromethyl)-4,5-dihydroisoxazol-3-yl)-N-(2-(ethylamino)-2-oxoethyl)-4,5,6,7-tetrahydrobenzo[c]thiophene-1-carboxamide | 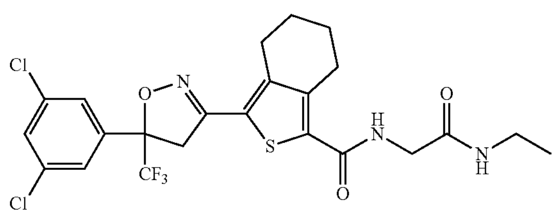 [SMILES: CCNC(=O)CNC(=O)c1sc(C2=NOC(c3cc(Cl)cc(Cl)c3)(C(F)(F)F)C2)c2c1CCCC2] | MS (m/z): 548 (M + 1); 1H NMR (CDCl3, 400 MHz) δ$^1$H NMR (CDCl$_3$, 400 MHz) δ 7.49 (s, 2H), 7.42 (m, 1H), 6.80 (s, 1H), 5.96 (s, 1H), 4.09-4.02 (m, 3H), 3.69-3.65 (d, J = 16 Hz, 1H), 3.40-3.33 (m, 2H), 3.00 (s, 2H), 2.92-2.90 (m, 2H), 1.79 (s, 4H), 1.26-1.17 (m, 3H). |
| 64 | 3-(5-(3,5-dichlorophenyl)-5-(trifluoromethyl)-4,5-dihydroisoxazol-3-yl)-N-((tetrahydrofuran-2-yl)methyl)-4,5,6,7-tetrahydrobenzo[c]thiophene-1-carboxamide | 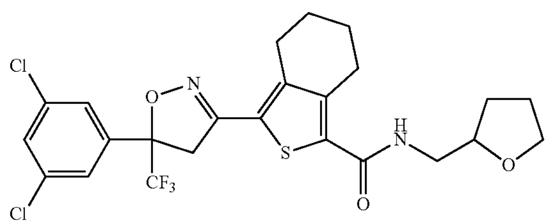 [SMILES: O=C(NCC1CCCO1)c1sc(C2=NOC(c3cc(Cl)cc(Cl)c3)(C(F)(F)F)C2)c2c1CCCC2] | MS (m/z): 547 (M + 1); 1H NMR (CDCl3, 400 MHz) δ7.48 (s, 2H), 7.42 (s, 1H), 6.23 (s, 1H), 4.08-4.02 (m, 2H), 3.91-3.86 (m, 1H), 3.81-3.76 (m, 2H), 3.69-3.65 (m, J = 16 Hz, 1H), 3.34-3.28 (m, 1H), 3.00-2.85 (m, 4H), 2.06-1.98 (m, 1H), 1.96-1.89 (m, 2H), 1.79-1.77 (m, 4H), 1.64-1.59 (m, 1H). |
| 65 | 3-(5-(3,5-dichlorophenyl)-5-(trifluoromethyl)-4,5-dihydroisoxazol-3-yl)-N-(2-(methylthio)ethyl)-4,5,6,7-tetrahydrobenzo[c]thiophene-1-carboxamide | 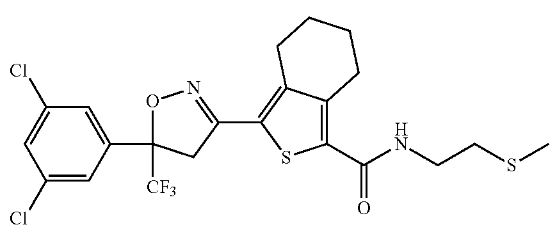 [SMILES: CSCCNC(=O)c1sc(C2=NOC(c3cc(Cl)cc(Cl)c3)(C(F)(F)F)C2)c2c1CCCC2] | MS (m/z): 537 (M + 1); 1H NMR (CDCl3, 400 MHz) δ 7.49 (s, 2H), 7.43 (s, 1H), 6.33 (s, 1H), 4.07-4.03 (d, J = 16 Hz, 1H), 3.69-3.62 (m, 3H), 2.98 (s, 2H), 2.92-2.90 (m, 2H), 2.76-2.74 (m, 2H), 2.14 (s, 3H), 1.80-1.79 (m, 4H). |
| 66 | 3-(5-(3,5-dichlorophenyl)-5-(trifluoromethyl)-4,5-dihydroisoxazol-3-yl)-N-(3,3,3-trifluoropropyl)-4,5,6,7-tetrahydrobenzo[c]thiophene-1-carboxamide | 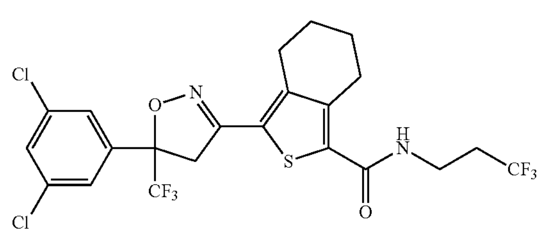 [SMILES: O=C(NCCC(F)(F)F)c1sc(C2=NOC(c3cc(Cl)cc(Cl)c3)(C(F)(F)F)C2)c2c1CCCC2] | MS (m/z): 559 (M + 1); 1H NMR (CDCl3, 400 MHz) δ 7.49 (s, 2H), 7.43 (s, 1H), 6.08-6.05 (m, 1H), 4.06-4.02 (d, J = 16 Hz, 1H), 3.72-3.64 (m, 3H), 2.94-2.85 (m, 4H), 2.51-2.40 (m, 2H), 1.80-1.78 (m, 4H). |

| Ex. No. | Chemical name | Structure | Physical data |
|---|---|---|---|
| 67 | 3-(5-(3,5-dichloro-phenyl)-5-(trifluoro-methyl)-4,5-dihydro-isoxazol-3-yl)-N-(3-hydroxycyclohexyl)-4,5,6,7-tetrahydrobenzo[c]thiophene-1-carboxamide | 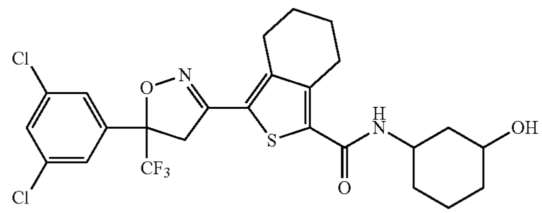 [SMILES: O=C(NC1CCCC(O)C1)c1sc(C2=NOC(c3cc(Cl)cc(Cl)c3)(C(F)(F)F)C2)c2c1CCCC2] | MS (m/z): 561 (M + 1); 1H NMR (CDCl3, 400 MHz) δ 7.49 (s, 2H), 7.43 (s, 1H), 6.85 (s, 1H), 4.21 (s, 1H), 4.09-4.02 (m, 2H), 3.69-3.64 (d, J = 20 Hz, 1H), 2.96-2.89 (m, 5H), 2.05-1.78 (m, 9H), 1.49-1.38 (m, 2H). |
| 68 | 3-(5-(3,5-dichloro-phenyl)-5-(trifluoro-methyl)-4,5-dihydro-isoxazol-3-yl)-N-(5-fluoropyridin-2-yl)-4,5,6,7-tetrahydro-benzo[c]thiophene-1-carboxamide | 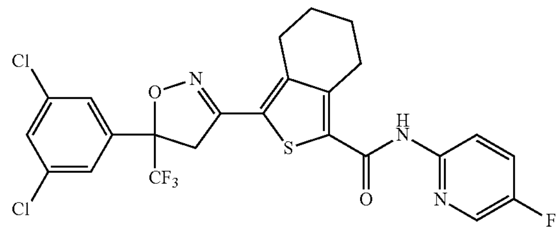 [SMILES: O=C(Nc1ccc(F)cn1)c1sc(C2=NOC(c3cc(Cl)cc(Cl)c3)(C(F)(F)F)C2)c2c1CCCC2] | MS (m/z): 558 (M + 1); 1H NMR (CDCl3, 400 MHz) δ 8.36 (s, 1H), 8.32-8.29 (m, 1H), 8.16 (d, J = 2.4 Hz, 1H), 7.51-7.44 (m, 3H), 7.43 (s, 1H), 4.09-4.05 (d, J = 16 Hz, 1H), 3.71-3.67 (d, J = 16 Hz, 1H), 3.09 (s, 2H), 2.94-2.93 (m, 2H), 1.83 (s, 4H) |
| 69 | 3-(5-(3,5-dichloro-phenyl)-5-(trifluoro-methyl)-4,5-dihydro-isoxazol-3-yl)-N-(tetrahydro-2H-pyran-3-yl)-4,5,6,7-tetrahydrobenzo[c]thiophene-1-carboxamide | 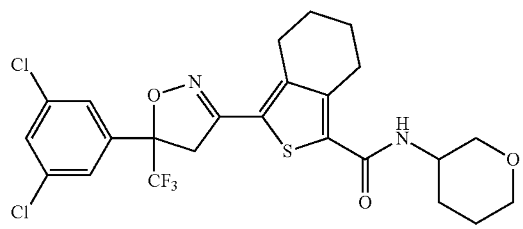 [SMILES: O=C(NC1CCCOC1)c1sc(C2=NOC(c3cc(Cl)cc(Cl)c3)(C(F)(F)F)C2)c2c1CCCC2] | MS (m/z): 547 (M + 1); 1H NMR (CDCl3, 400 MHz) δ 7.49 (s, 2H), 7.40 (s, 1H), 6.23 (d, J = 9.6 Hz, 1H), 4.18-4.16 (s, 1H), 4.07-4.03 (d, J = 16 Hz, 1H), 3.83-3.77 (m, 2H), 3.69-3.57 (m, 3H), 2.98-2.90 (m, 4H), 1.90-1.75 (m, 8H). |
| 70 | 3-(5-(3,5-dichloro-phenyl)-5-(trifluoro-methyl)-4,5-dihydro-isoxazol-3-yl)-N-(thietan-3-yl)-4,5,6,7-tetrahydrobenzo[c]thiophene-1-carboxamide | 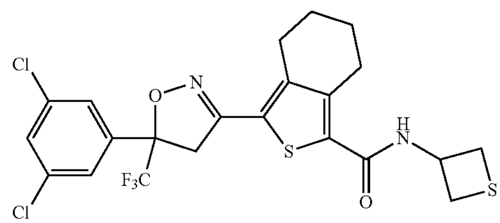 [SMILES: O=C(NC1CSC1)c1sc(C2=NOC(c3cc(Cl)cc(Cl)c3)(C(F)(F)F)C2)c2c1CCCC2] | MS (m/z): 535 (M + 1); 1H NMR (CDCl3, 400 MHz) δ 7.49 (s, 2H), 7.44 (s, 1H), 6.18 (d, J = 7.6 Hz, 1H), 5.40-5.34 (m, 1H), 4.06 (d, J = 17.2 Hz, 1H), 3.66 (d, J = 17.2 Hz, 1H), 3.46-3.36 (m, 4H), 2.97-2.90 (m, 4H), 1.81-1.78 (m, 4H). |
| 71 | 3-(5-(3,5-dichloro-phenyl)-5-(trifluoro-methyl)-4,5-dihydro-isoxazol-3-yl)-N-(tetrahydro-2H-pyran-4-yl)-4,5,6,7-tetrahydrobenzo[c]thiophene-1-carboxamide | 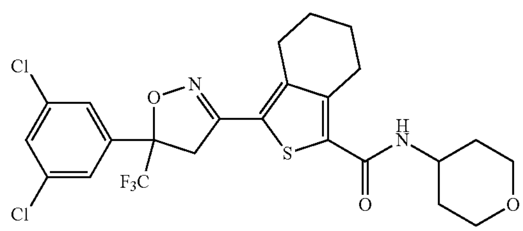 [SMILES: O=C(NC1CCOCC1)c1sc(C2=NOC(c3cc(Cl)cc(Cl)c3)(C(F)(F)F)C2)c2c1CCCC2] | MS (m/z): 547 (M + 1); 1H NMR (CDCl3, 400 MHz) δ 7.47 (s, 2H), 7.41 (s, 1H), 5.74-5.72 (d, J = 7.6 Hz, 1H), 4.19-4.11 (m, 1H), 4.10-4.06 (d, J = 16 Hz, 1H), 4.04-3.96 (m, 2H), 3.69-3.65 (d, J = 16 Hz, 1H), 3.53-3.43 (m, 2H), 2.94-2.88 (m, 4H), 2.00-1.97 (m, 2H), 1.77 (s, 4H), 1.60-1.50 (m, 2H). |
| 72 | N-(1-cyclopropyl-2-oxopyrrolidin-3-yl)-3-(5-(3,5-dichloro-phenyl)-5-(trifluoro-methyl)-4,5-dihydro-isoxazol-3-yl)-4,5,6,7-tetrahydrobenzo[c]thiophene-1-carboxamide | 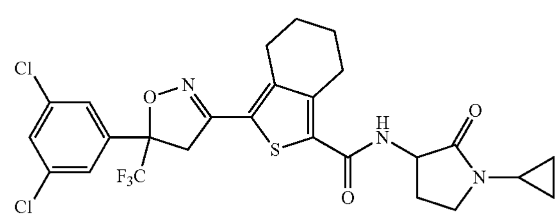 [SMILES: O=C(NC1CCN(C2CC2)C1=O)c1sc(C2=NOC(c3cc(Cl)cc(Cl)c3)(C(F)(F)F)C2)c2c1CCCC2] | MS (m/z): 586 (M + 1); 1H NMR (CDCl3, 400 MHz) δ 7.49 (s, 2H), 7.43 (s, 1H), 6.50 (brs, 1 H), 4.43-4.40 (m, 1 H), 4.04 (d, J = 16.8, 1 H), 3.65 (d, J = 16.8, 1 H), 3.42-3.30 (m, 2 H), 2.99-2.82 (m, 5 H), 1.91-1.80 (m, 5 H), 0.83-0.763 (m, 4 H) |
| 74 | N-(2-oxo-2-(prop-2-ynylamino)ethyl)-3-(5-(3,4,5-trichloro-thiophen-2-yl)-5-(trifluoromethyl)-4,5-dihydroisoxazol-3-yl)-4,5,6,7-tetrahydro-benzo[c]thiophene-1-carboxamide | 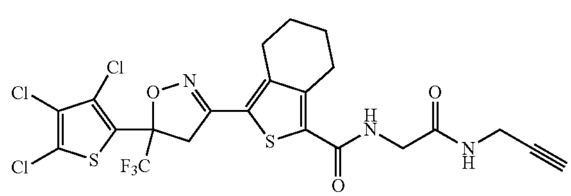 [SMILES: C#CCNC(=O)CNC(=O)c1sc(C2=NOC(c3sc(Cl)c(Cl)c3Cl)(C(F)(F)F)C2)c2c1CCCC2] | MS (m/z): 600 (M + 1); 1H NMR (CDCl3, 400 MHz) δ 6.92-6.77 (m, 2H), 4.21-4.09 (m, 4H), 4.08-4.04 (m, 2H), 3.09-2.88 (m, 4H), 1.87-1.71 (m, 4H). |

| Ex. No. | Chemical name | Structure | Physical data |
|---|---|---|---|
| 75 | 3-[5-(3,4,5-Trichloro-phenyl)-5-trifluoro-methyl-4,5-dihydro-isoxazol-3-yl]-4,5,6,7-tetrahydro-benzo[c]thiophene-1-carboxylic acid (1,1-dioxo-hexahydro-thiopyran-4-yl)-amide | 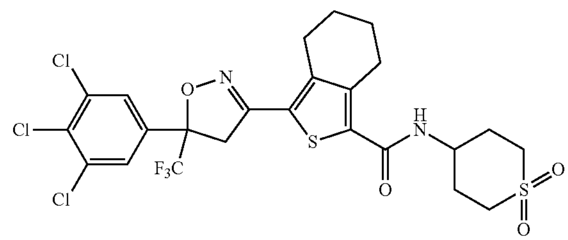 [SMILES: O=C(NC1CCS(=O)(=O)CC1)c1sc(C2=NOC(c3cc(Cl)c(Cl)c(Cl)c3)(C(F)(F)F)C2)c2c1CCCC2] | MS (m/z): 631 (M + 1); 1H NMR (CDCl3, 400 MHz) δ 7.62 (s, 2H), 5.89-5.87 (m, 1H), 4.28-4.20 (m, 1H), 4.07-4.03 (d, J = 16 Hz, 1H), 3.70-3.66 (d, J = 16 Hz, 1H), 3.20-3.12 (m, 4H), 2.94-2.89 (m, 4H), 2.42-2.39 (m, 2H), 2.27-2.17 (m, 2H), 1.79 (s, 4H). |
| 76 | N-(2-oxo-1-(2,2,2-trifluoroethyl)pyrrolidin-3-yl)-3-(5-(3,4,5-trichloro-phenyl)-5-(trifluoro-methyl)-4,5-dihydro-isoxazol-3-yl)-4,5,6,7-tetrahydro-benzo[c]thiophene-1-carboxamide | 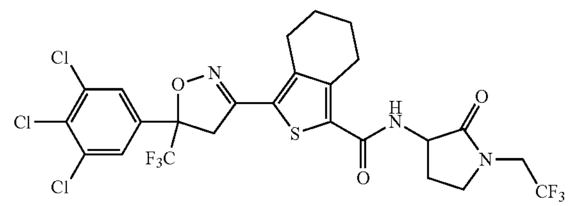 [SMILES: O=C(NC1CCN(CC(F)(F)F)C1=O)c1sc(C2=NOC(c3cc(Cl)c(Cl)c(Cl)c3)(C(F)(F)F)C2)c2c1CCCC2] | MS (m/z): 664 (M + 1); 1H NMR (CDCl3, 400 MHz) δ 7.63 (s, 2 H), 6.45 (brs, 1 H), 4.53 (brs, 1 H), 4.09 (m, 2 H), 3.85 (m, 1 H), 3.58 (m, 3 H), 2.95 (m, 4 H), 2.02 (m, 1 H), 1.79 (m, 4 H). |
| 77 | N-(tetrahydro-2H-pyran-4-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide | 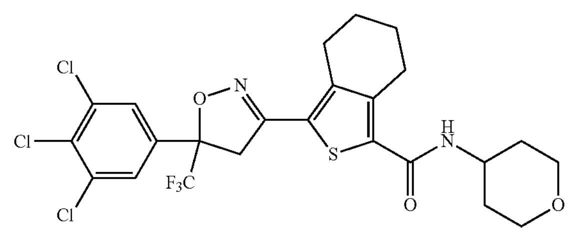 [SMILES: O=C(NC1CCOCC1)c1sc(C2=NOC(c3cc(Cl)c(Cl)c(Cl)c3)(C(F)(F)F)C2)c2c1CCCC2] | MS (m/z): 583 (M + 1); 1H NMR (CDCl3, 400 MHz) δ 7.61 (s, 2H), 5.70-5.68 (d, J = 8.0 Hz, 1H), 4.19-4.11 (m, 1H), 3.70-3.66 (d, J =16 Hz, 1H), 4.00-3.97 (m, 2H), 3.68-3.64 (d, J = 16 Hz, 1H), 3.54-3.48 (m, 2H), 2.94-2.88 (m, 4H), 2.00-1.98 (m, 2H), 1.79 (s, 4H), 1.64-1.50 (m, 2H). |
| 78 | N-(1-cyclopropyl-2-oxopyrrolidin-3-yl)-3-(5-(3,4,5-trichloro-phenyl)-5-(trifluoro-methyl)-4,5-dihydro-isoxazol-3-yl)-4,5,6,7-tetrahydrobenzo[c]thiophene-1-carboxamide | 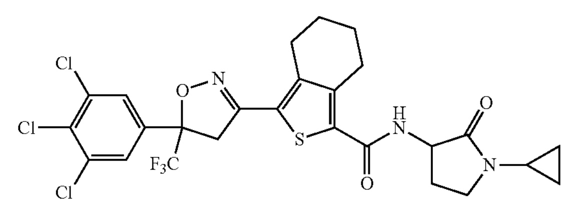 [SMILES: O=C(NC1CCN(C2CC2)C1=O)c1sc(C2=NOC(c3cc(Cl)c(Cl)c(Cl)c3)(C(F)(F)F)C2)c2c1CCCC2] | MS (m/z): 622 (M + 1); 1H NMR (CDCl3, 400 MHz) δ 8.00 (s, 2 H), 6.53 (brs, 1 H), 4.43 (m, 1 H), 4.04 (d, J = 17.2, 1 H), 3.65 (d, J = 17.2, 1 H), 3.36 (m, 2 H), 2.83 (m, 5 H), 2.73 (m, 1 H), 1.84 (m, 5 H), 0.79 (m, 4 H). |
| 79 | 3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid (1,1-dioxo-thietan-3-yl)-amide | 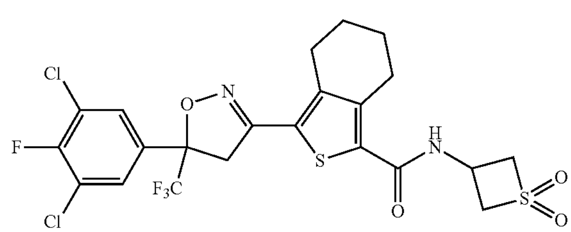 [SMILES: O=C(NC1CS(=O)(=O)C1)c1sc(C2=NOC(c3cc(Cl)c(F)c(Cl)c3)(C(F)(F)F)C2)c2c1CCCC2] | MS (m/z): 585 (M + 1); 1H NMR (CDCl3, 400 MHz) δ 7.76 (d, J = 6.0, 2H), 4.65-4.56 (m, 1H), 4.53 (t, J = 4.8, 2H), 4.28-4.23 (m, 3H), 4.02 (d, J = 17.6, 1H), 2.97 (t, J = 6.0, 2H), 2.90 (t, J = 6.0, 2H), 1.80-1.76 (m, 4H). |
| 80 | 3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-thiopyran-4-yl)-amide | 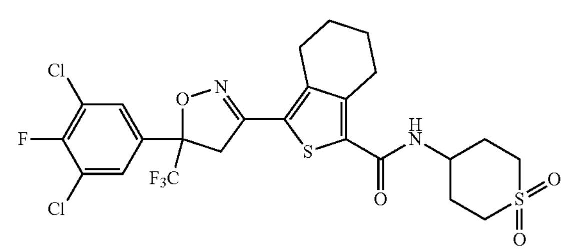 [SMILES: O=C(NC1CCS(=O)(=O)CC1)c1sc(C2=NOC(c3cc(Cl)c(F)c(Cl)c3)(C(F)(F)F)C2)c2c1CCCC2] | MS (m/z): 613 (M + 1); 1H NMR (CDCl3, 400 MHz) δ 7.56 (d, J = 6.0, 2 H), 5.75 (d, J = 7.2, 1 H), 4.06 (d, J = 16.8, 1 H), 3.65 (d, J = 16.8, 1 H), 3.13 (m, 4 H), 2.91 (m, 4 H), 2.41 (m, 2 H), 2.23 (m, 2 H), 1.84 (m, 4 H). |

| Ex. No. | Chemical name | Structure | Physical data |
|---|---|---|---|
| 81 | 3-(5-(3,5-dichloro-4-fluorophenyl)-5-(trifluoromethyl)-4,5-dihydroisoxazol-3-yl)-N-(4-oxocyclohexyl)-4,5,6,7-tetrahydrobenzo[c]thiophene-1-carboxamide | 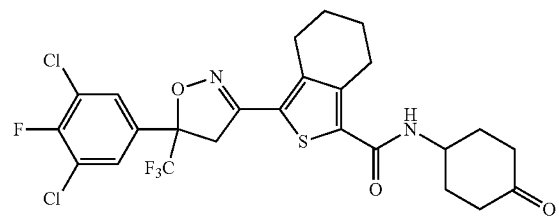 [SMILES: O=C1CCC(NC(=O)c2sc(C3=NOC(c4cc(Cl)c(F)c(Cl)c4)(C(F)(F)F)C3)c3c2CCCC3)CC1] | MS (m/z): 577 (M + 1); 1H NMR (CDCl3, 400 MHz) δ 7.48 (d, J = 6.0, 2H), 5.67 (d, J = 6.8, 1H), 4.33 (m, 1H), 3.98 (d, J = 16.8, 1H), 3.58 (d, J = 16.8, 1H), 2.82 (m, 4H), 2.40 (m, 6H), 1.65 (m, 6H) |
| 82 | 3-(5-(3,5-dichloro-4-fluorophenyl)-5-(trifluoromethyl)-4,5-dihydro-isoxazol-3-yl)-N-(2-oxo-1-(2,2,2-trifluoroethyl)pyrrolidin-3-yl)-4,5,6,7-tetra-hydrobenzo[c]thiophene-1-carboxamide | 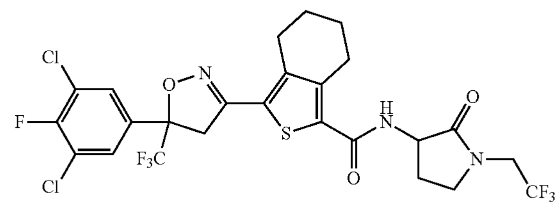 [SMILES: O=C(NC1CCN(CC(F)(F)F)C1=O)c1sc(C2=NOC(c3cc(Cl)c(F)c(Cl)c3)(C(F)(F)F)C2)c2c1CCCC2] | MS (m/z): 646 (M + 1); 1H NMR (CDCl3, 400 MHz) δ 7.50 (dd, J$_1$ = 2.4, J$_2$ = 6.0, 2H), 6.44 (dd, J$_1$ = 4.8, J$_2$ = 12.0, 1 H), 4.46 (m, 1 H), 3.98 (m, 2 H), 3.78 (m, 1 H), 3.55 (m, 3 H), 2.83 (m, 5 H), 1.963 (m, 1 H), 1.71 (m, 4H). |
| 83 | 3-(5-(3,5-dichloro-4-fluorophenyl)-5-(trifluoromethyl)-4,5-dihydro-isoxazol-3-yl)-N-(tetrahydro-2H-pyran-4-yl)-4,5,6,7-tetrahydro-benzo[c]thiophene-1-carboxamide | 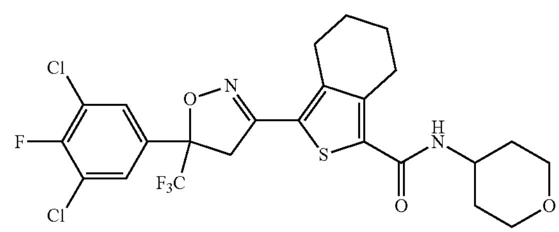 [SMILES: O=C(NC1CCOCC1)c1sc(C2=NOC(c3cc(Cl)c(F)c(Cl)c3)(C(F)(F)F)C2)c2c1CCCC2] | MS (m/z): 565 (M + 1); 1H NMR (CDCl3, 400 MHz) δ 7.49 (d, J = 5.6, 2 H), 5.59 (d, J = 7.6, 1 H), 4.10 (m, 1 H), 3.98 (d, J = 16.8, 1 H), 3.91 (m, 2 H), 3.58 (d, J = 16.8, 1 H), 3.45 (m, 2 H), 2.84 (m, 4 H), 1.95 (m, 2 H), 1.72 (m, 4 H), 1.49 (m, 3 H). |
| 84 | N-(1-cyclopropyl-2-oxopyrrolidin-3-yl)-3-(5-(3,5-dichloro-4-fluorophenyl)-5-(trifluoromethyl)-4,5-dihydroisoxazol-3-yl)-4,5,6,7-tetra-hydrobenzo[c]thiophene-1-carboxamide | 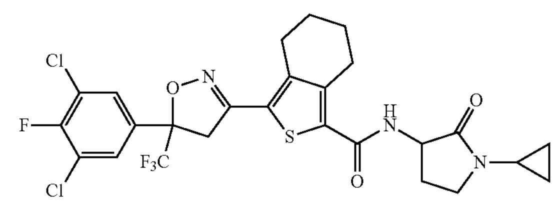 [SMILES: O=C(NC1CCN(C2CC2)C1=O)c1sc(C2=NOC(c3cc(Cl)c(F)c(Cl)c3)(C(F)(F)F)C2)c2c1CCCC2] | MS (m/z): 604 (M + 1); 1H NMR (CDCl3, 400 MHz) δ 7.77 (d, J = 6.0, 2H), 4.62 (t, J = 9.6, 1H), 4.24 (d, J = 17.6, 1H), 4.02 (d, J = 17.6, 1H), 3.43-3.39 (m, 2H), 2.99-2.96 (m, 2H), 2.90-2.88 (m, 2H), 2.75-2.69 (m, 1H), 2.50-2.42 (m, 1H), 2.10-1.99 (m, 1H), 1.81-1.78 (m, 4H), 0.85-0.82 (m, 4H). |
| 85 | 3-(5-(3,5-dichloro-phenyl)-5-(trifluoro-methyl)-4,5-dihydro-isoxazol-3-yl)-N-(4-oxocyclohexyl)-5,6-dihydro-4H-cyclopenta[c]thiophene-1-carboxamide | 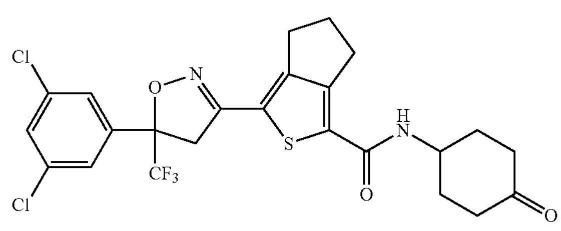 [SMILES: O=C1CCC(NC(=O)c2sc(C3=NOC(c4cc(Cl)cc(Cl)c4)(C(F)(F)F)C3)c3c2CCC3)CC1] | MS (m/z): 545 (M + 1); 1H NMR (CDCl3, 400 MHz) δ 7.52-7.44 (m, 3H), 5.72-5.68 (m, 1H), 4.48-4.37 (m, 1H), 4.04-3.97 (d, J = 17.2, 1H), 3.65-3.59 (d, J = 17.2, 1H), 2.92-2.84 (m, 4H), 2.58-2.48 (m, 6H), 2.47-2.31 (m, 2H), 1.84-1.71 (m, 2H). |
| 86 | 3-(5-(3,5-dichloro-phenyl)-5-(trifluoro-methyl)-4,5-dihydro-isoxazol-3-yl)-N-(2-oxo-1-(2,2,2-trifluoroethyl)pyrrolidin-3-yl)-5,6-dihydro-4H-cyclopenta[c]thiophene-1-carboxamide | 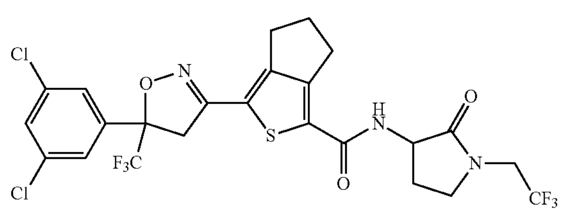 [SMILES: O=C(NC1CCN(CC(F)(F)F)C1=O)c1sc(C2=NOC(c3cc(Cl)cc(Cl)c3)(C(F)(F)F)C2)c2c1CCC2] | MS (m/z): 614 (M + 1); 1H NMR (CDCl3, 400 MHz) δ7.52-7.44 (m, 3H), 6.43-6.38 (s, 1H), 4.52-4.48 (m, 1H), 4.17-4.05 (m, 2H), 4.04-3.97 (d, J = 17.2, 1H), 3.89-3.77 (m, 1H), 3.68-3.51 (m, 3H), 2.93-2.82 (m, 5H), 2.58-2.46 (m, 2H), 2.08-1.97 (m, 1H). |

Example 87

(A)

3-((R)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide and (B)

3-((S)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide

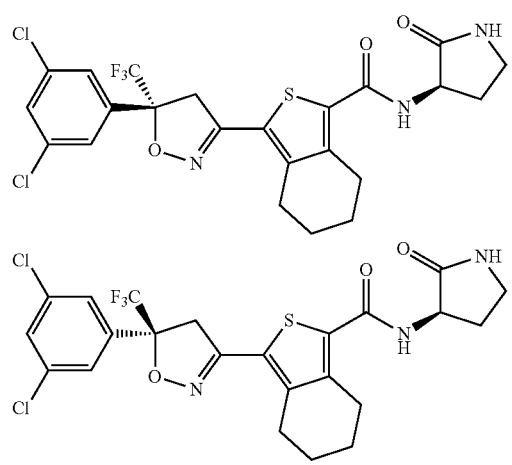

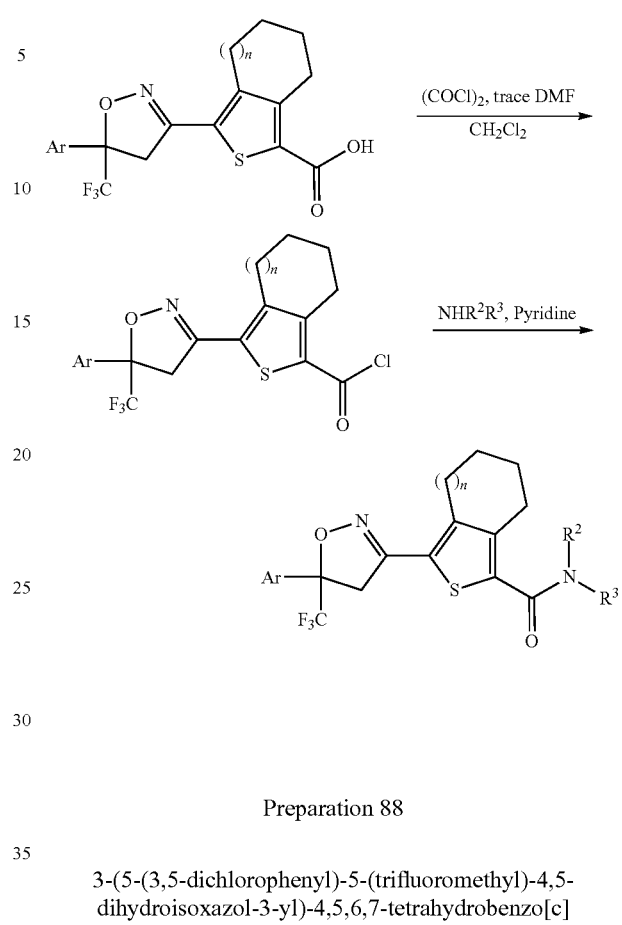

Scheme B

Separate 3-(5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide (6.2 g 11.29 mmol) by SFC (Column: Chiralcel OD 250×30 mm I.D., 5 um. Mobile phase: Supercritical CO₂/MeOH=60/40, Flow rate: 200 ml/min) to afford two diastereoisomers 3-((R)-5-(3,5-dichlorophenyl)-5-(trifluoromethyl)-4,5-dihydroisoxazol-3-yl)-N—((R)-2-ox pyrrolidin-3-yl)-4,5,6,7-tetrahydrobenzo[c]thiophene-1-carboxamide (2.7 g, 4.92 mmol) and 3-((S)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide (2.6 g, 4.74 mmol) as a white solid.

(A) MS (m/z): 619.1 (M+73). $^1$H NMR (CDCl₃, 400 MHz) δ 7.49 (s, 2H), 7.42 (s, 1H), 6.56 (d, J=4.4 Hz 1H), 6.03 (s, 1H), 4.50-4.44 (m, 1H), 4.06-4.02 (d, J=16 Hz, 1H), 3.69-3.65 (d, J=16 Hz, 1H), 3.48-3.43 (m, 2H), 3.03-2.98 (m, 5H), 2.11-2.00 (m, 1H), 1.78 (s, 4H).

(B) MS (m/z): 619.1 (M+73). $^1$H NMR (CDCl₃, 400 MHz) δ 7.49 (m, 2H), 7.41 (m, 1H), 6.77-6.73 (m, 1H), 6.38-6.31 (m, 1H), 4.51-4.45 (m, 1H), 4.05-4.01 (d, J=16 Hz, 1H), 3.71-3.67 (d, J=16 Hz, 1H), 3.49-3.39 (m, 2H), 3.00-2.85 (m, 5H), 2.04-2.03 (m, 1H), 1.74 (s, 4H).

Preparation 88

3-(5-(3,5-dichlorophenyl)-5-(trifluoromethyl)-4,5-dihydroisoxazol-3-yl)-4,5,6,7-tetrahydrobenzo[c]thiophene-1-carbonyl chloride

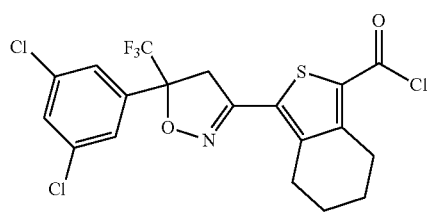 [SMILES: O=C(Cl)c1sc(C2=NOC(c3cc(Cl)cc(Cl)c3)(C(F)(F)F)C2)c2c1CCCC2]

Stir a mixture of 3-[5-(3,5-Dichloro-phenyl)-5-trifluoromethyl-4,5-dihydro-isoxazol-3-yl]-4,5,6,7-tetrahydro-benzo[c]thiophene-1-carboxylic acid (600 mg, 1.2 mmol), 2 drops DMF in oxalyl dichloride (5 mL) at ambient temperature for 3 hours. Remove the solvent under vacuum to afford 3-(5-(3,5-dichlorophenyl)-5-(trifluoromethyl)-4,5-dihydroisoxazol-3-yl)-4,5,6,7-tetrahydrobenzo[c]thiophene-1-carbonyl chloride as a yellow solid (615 mg, 98%).

The following compound is prepared essentially by the method of Preparation 88.

| Prep. No. | Chemical name | Structure | Physical data |
|---|---|---|---|
| 89 | 3-[5-(3,4,5-Trichloro-thiophen-2-yl)-5-tri-fluoromethyl-4,5-dihydro-isoxazol-3-yl]-4,5,6,7-tetrahydro-benzo[c]thiophene-1-carbonyl chloride | 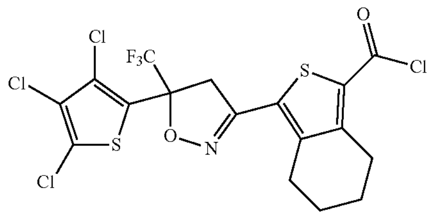 [SMILES: O=C(Cl)c1sc(C2=NOC(c3sc(Cl)c(Cl)c3Cl)(C(F)(F)F)C2)c2c1CCCC2] | |

Example 90

N-(4-carbamoylphenyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide

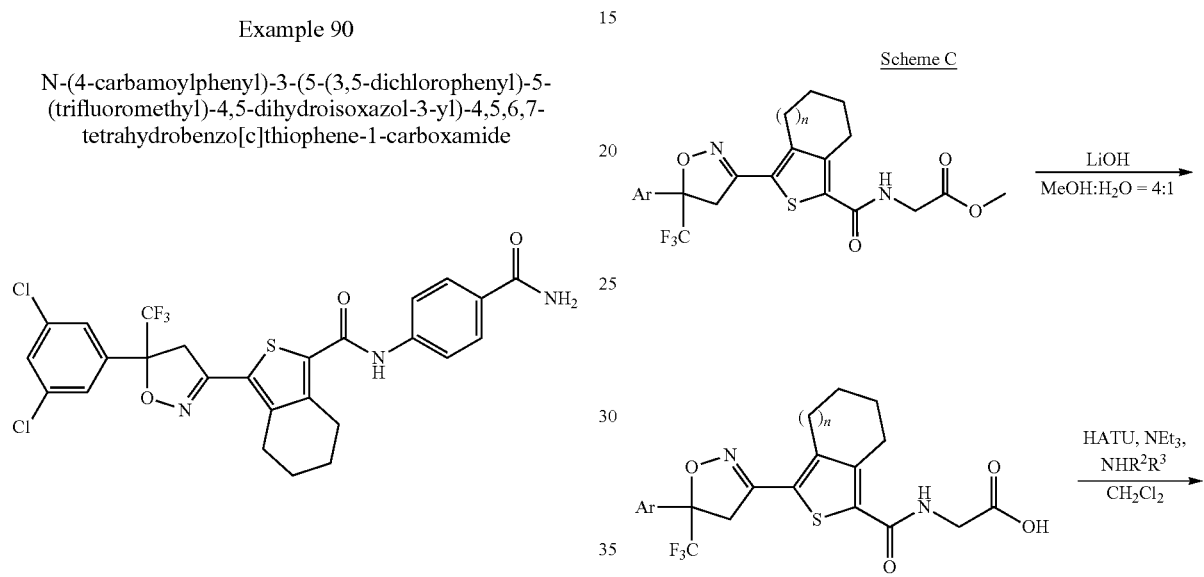

Scheme C

Stir a mixture of 3-(5-(3,5-dichlorophenyl)-5-(trifluoromethyl)-4,5-dihydroisoxazol-3-yl)-4,5,6,7-tetrahydrobenzo[c]thiophene-1-carbonyl chloride (48 mg, 0.1 mmol) and 4-aminobenzamide (27 mg, 0.2 mmo) in pyridine (3 mL) at ambient temperature overnight. After removal solvent under vacuum, purify the residue by preparative HPLC to afford N-(4-carbamoylphenyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide as a white solid (36 mg, 62.0%). MS (m/z): 582.1 (M+1). $^1$H NMR (CDCl$_3$, 400 MHz) δ 7.84 (d, J=8.4 Hz, 2H), 7.65-7.63 (m, 3H), 7.49 (s, 2H), 7.44 (s, 1H), 6.03 (s, 1H), 5.61 (s, 1H), 4.09-4.05 (d, J=16 Hz, 1H), 3.72-3.68 (d, J=16 Hz, 1H), 3.07 (s, 2H), 2.94 (s, 2H), 1.76 (s, 4H).

The following compound is prepared essentially by the method of Example 90.

| Ex. No. | Chemical name | Structure | Physical data |
|---|---|---|---|
| 91 | 3-[5-(3,4,5-Trichloro-thiophen-2-yl)-5-trifluoro-methyl-4,5-dihydro-isoxazol-3-yl]-4,5,6,7-tetrahydro-benzo[c]thiophene-1-carboxylic acid (3-carbamoyl-thiophen-2-yl)-amide | 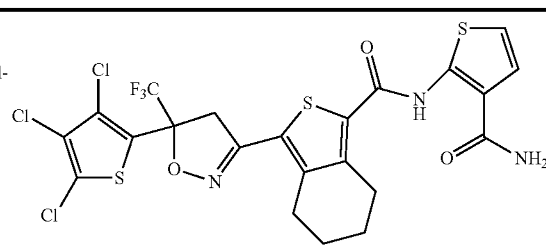 | MS (m/z): 628 (M + 1); $^1$H NMR (400 MHz, DMSO-d$_6$,) δ 8.08-8.02 (m, 1H), 7.81-7.78 (m, 1H), 4.58-4.43 (t, 2H), 3.13-2.84 (m, 4H), 1.79-1.64 (m, 4H). |

Preparation 92

2-(3-(5-(3,5-dichlorophenyl)-5-(trifluoromethyl)-4,5-dihydroisoxazol-3-yl)-4,5,6,7-tetrahydrobenzo[c]thiophene-1-carboxamido)acetic acid

Example 94

N-(2-(cyanomethylamino)-2-oxoethyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide

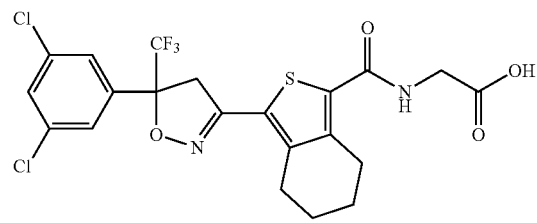 [SMILES: O=C(O)CNC(=O)c1sc(C2=NOC(c3cc(Cl)cc(Cl)c3)(C(F)(F)F)C2)c2c1CCCC2]

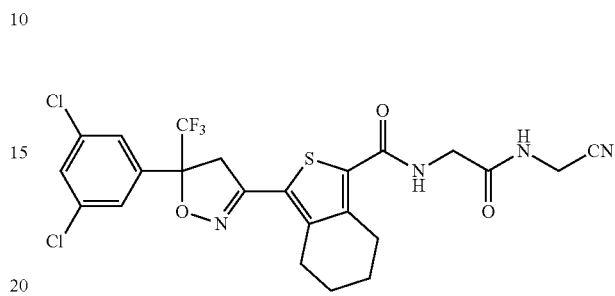

Stir a mixture of methyl 2-(3-(5-(3,5-dichlorophenyl)-5-(trifluoromethyl)-4,5-dihydroisoxazol-3-yl)-4,5,6,7-tetrahydrobenzo[c]thiophene-1-carboxamido)acetate (534 mg, 1.0 mmol) and LiOH—$H_2O$ (168 mg, 4.0 mmol) in MeOH (20 mL) and water (5 mL) at room temperature for overnight. After removal of organic solvent under vacuum, dilute the residue with ice water (10 mL). Acidify the aqueous mixture with conc. HCl to pH=1, and extract the resultant mixture with EtOAc (15 mL×3). The combined organic layers are washed brine, dried over anhydrous $Na_2SO_4$ and concentrated under vacuum. Purify the residue by silica gel chromatograph (PE:EtOAc 1:1) to afford 2-(3-(5-(3,5-dichlorophenyl)-5-(trifluoromethyl)-4,5-dihydroisoxazol-3-yl)-4,5,6,7-tetrahydrobenzo[c]thiophene-1-carboxamido)acetic acid as a pale yellow solid (427 mg, 82.0%). MS (m/z): 521 (M+1).

The following compound is prepared essentially by the method of Preparation 92.

Stir a mixture of 2-(3-(5-(3,5-dichlorophenyl)-5-(trifluoromethyl)-4,5-dihydroisoxazol-3-yl)-4,5,6,7-tetrahydrobenzo[c]thiophene-1-carboxamido)acetic acid (230 mg, 0.44 mmol), HATU (251 mg, 0.66 mmol) and $NEt_3$ (133 mg, 1.32 mmol) in DCM (5 mL) at room temperature for 15 min, followed by addition of 2-aminoacetonitrile hydrochloride (61 mg, 0.65 mmol). Stir the reaction mixture at room temperature for additional 1.5 hour. Dilute the reaction mixture with water (20 mL) and extract with DCM (20 mL×3). The combined organic layers are washed with brine, dried over anhydrous $Na_2SO_4$ and concentrated under vacuum. Purify the residue by preparative HPLC to afford N-(2-(cyanomethylamino)-2-oxoethyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide as a white solid (110 mg, 44.7%). MS (m/z): 559.1 (M+1). $^1$H NMR (DMSO-$d_6$, 400 MHz) δ 8.64 (t, J=5.6 Hz, 1H), 8.22 (t, J=5.6 Hz, 1H), 7.81-7.80 (m 1H), 7.68 (s, 2H), 4.35-4.22 (m, 2H), 4.16-4.15 (m, 2H), 3.88-3.86 (m, 2H), 2.94-2.86 (m, 4H), 1.70-1.69 (m, 4H).

The following compounds are prepared essentially by the method of Example 94.

| Prep. No. | Chemical name | Structure | Physical data |
|---|---|---|---|
| 93 | ({3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl}-amino)-acetic acid | 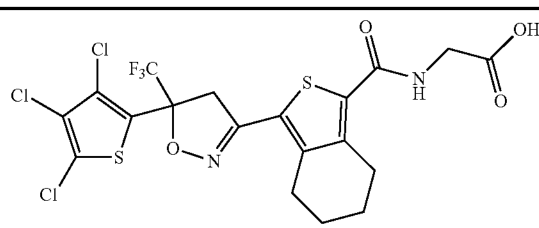 | MS (m/z): 561 (M + 1). |

| Ex. No. | Chemical name | Structure | Physical data |
|---|---|---|---|
| 95 | 3-(5-(3,5-dichlorophenyl)-5-(trifluoromethyl)-4,5-dihydroisoxazol-3-yl)-N-(2-oxo-2-(prop-2-ynylamino)ethyl)-4,5,6,7-tetrahydrobenzo[c]thiophene-1-carboxamide | 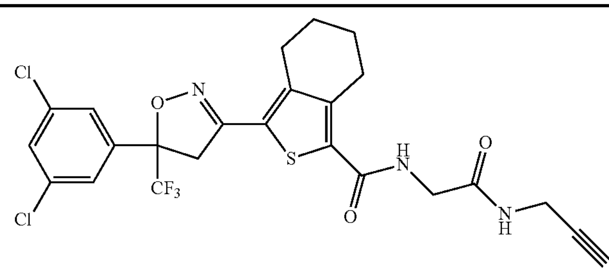 | MS (m/z): 558 (M + 1); $^1$H NMR (CDCl$_3$, 400 MHz) δ 7.49-7.42 (m, 3H), 6.85 (br, 1H), 6.72 (br, 1H), 4.17-4.03 (m, 5H), 3.68 (d, J = 17.2 Hz, 1H), 3.00-2.90 (m, 4H), 2.25 (s, 1H), 1.79 (br, 4H). |
| 96 | N-(2-(cyanomethylamino)-2-oxoethyl)-3-(5-(3,4,5-trichlorothiophen-2-yl)-5-(trifluoromethyl)-4,5-dihydroisoxazol-3-yl)-4,5,6,7-tetrahydrobenzo[c]thiophene-1-carboxamide | 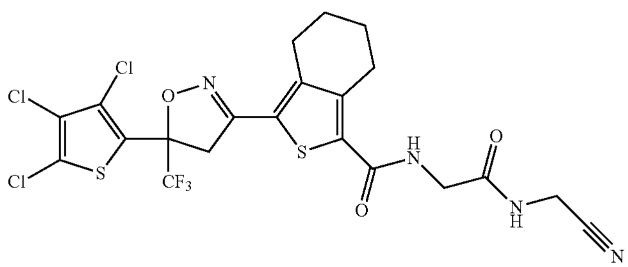 [SMILES: N#CCNC(=O)CNC(=O)c1sc(C2=NOC(c3sc(Cl)c(Cl)c3Cl)(C(F)(F)F)C2)c2c1CCCC2] | MS (m/z): 599 (M + 1); $^1$H NMR (CDCl$_3$, 400 MHz) δ 4.28-4.18 (m, 4H), 4.10-4.07 (m, 2H), 3.04-2.87 (m, 4H), 1.88-1.73 (m, 4H). |

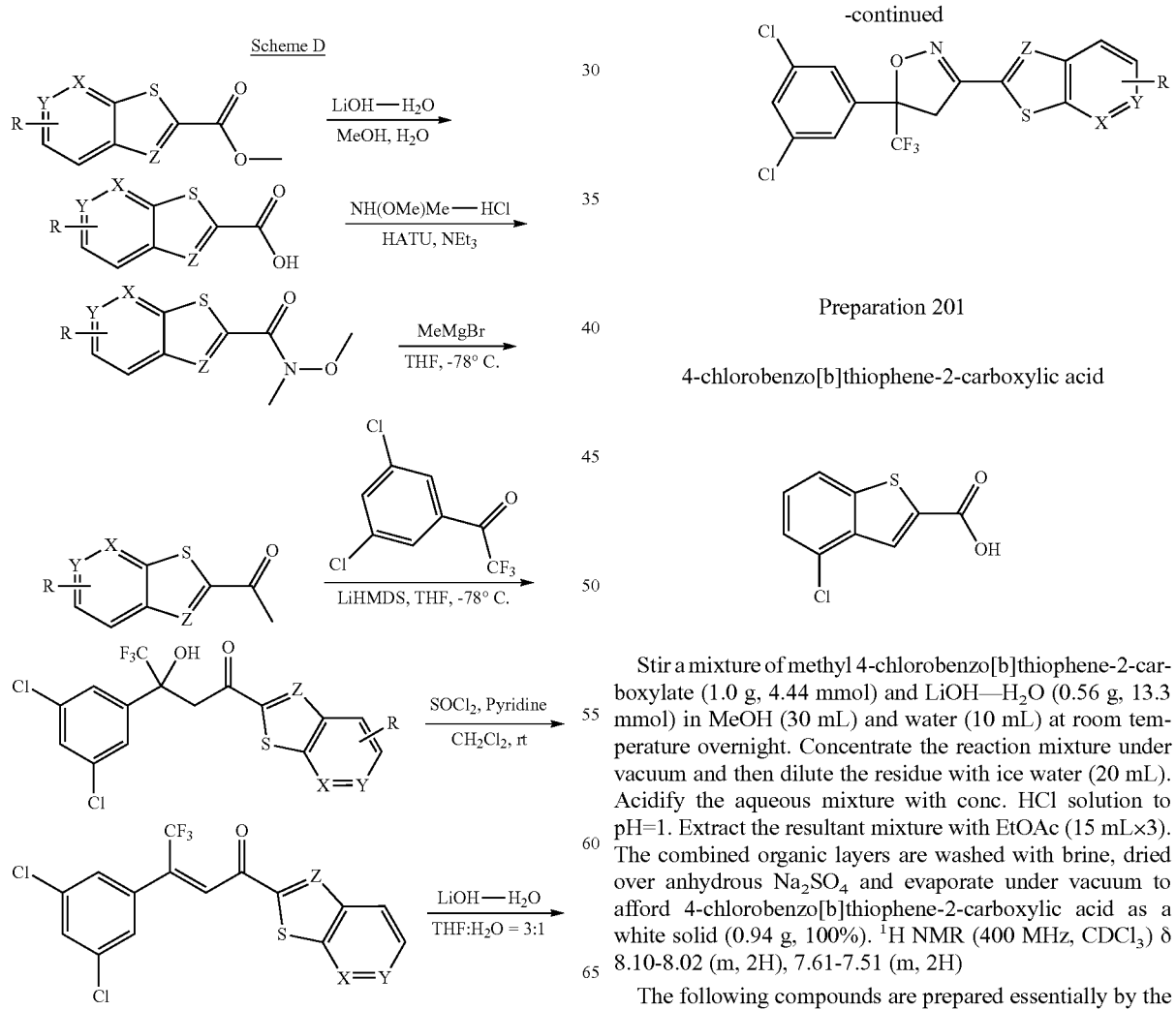

Preparation 201

4-chlorobenzo[b]thiophene-2-carboxylic acid

Stir a mixture of methyl 4-chlorobenzo[b]thiophene-2-carboxylate (1.0 g, 4.44 mmol) and LiOH—H$_2$O (0.56 g, 13.3 mmol) in MeOH (30 mL) and water (10 mL) at room temperature overnight. Concentrate the reaction mixture under vacuum and then dilute the residue with ice water (20 mL). Acidify the aqueous mixture with conc. HCl solution to pH=1. Extract the resultant mixture with EtOAc (15 mL×3). The combined organic layers are washed with brine, dried over anhydrous Na$_2$SO$_4$ and evaporate under vacuum to afford 4-chlorobenzo[b]thiophene-2-carboxylic acid as a white solid (0.94 g, 100%). $^1$H NMR (400 MHz, CDCl$_3$) δ 8.10-8.02 (m, 2H), 7.61-7.51 (m, 2H)

The following compounds are prepared essentially by the method of Preparation 201.

| Prep. No. | Chemical name | Structure | Physical data |
|---|---|---|---|
| 202 | Thieno[2,3-c]pyridine-2-carboxylic acid | 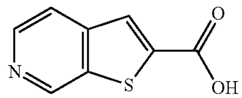 [SMILES: O=C(O)c1cc2ccncc2s1] | MS (m/z): 180 (M + 1) |
| 203 | 5-Bromo-thieno[2,3-b]pyridine-2-carboxylic acid | 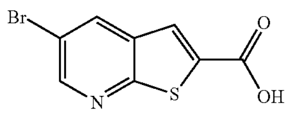 [SMILES: O=C(O)c1cc2cc(Br)cnc2s1] | MS (m/z): 260 (M + 1). |

Preparation 204

4-chloro-N-methoxy-N-methylbenzo[b]thiophene-2-carboxamide

Stir a mixture of 4-chlorobenzo[b]thiophene-2-carboxylic acid (0.94 g, 4.44 mmol), N,O-dimethylhydroxylamine hydrochloride (0.86 g, 8.87 mmol), DCC (1.1 g, 5.32 mmol) and DIEA (1.43 g, 1.9 mL, 11.08 mmol) in DCM (8 mL) at ambient temperature for 2 hours. Filter the reaction mixture and the filtrate is washed with brine, dried over anhydrous Na$_2$SO$_4$ and concentrated under vacuum. Purify the residue by column chromatography on silica gel eluting with PE:EtOAc (5:1 to 3:1) to afford 4-chloro-N-methoxy-N-methyl-benzo[b]thiophene-2-carboxamide as white solid (0.85 g, 75.2%). $^1$H NMR (400 MHz, CDCl$_3$) δ 8.10-8.02 (m, 2H), 7.61-7.51 (m, 2H), 3.84-3.79 (s, 3H), 3.37-3.35 (s, 3H).

The following compound is prepared essentially by the method of Preparation 204.

| Prep. No. | Chemical name | Structure | Physical data |
|---|---|---|---|
| 205 | N-methoxy-N-methylthieno[2,3-c]pyridine-2-carboxamide | 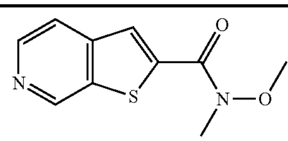 | MS (m/z): 223 (M + 1). |
| 206 | 5-bromo-N-methoxy-N-methylthieno[2,3-b]pyridine-2-carboxamide | 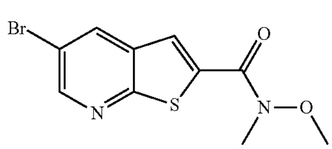 [SMILES: CON(C)C(=O)c1cc2cc(Br)cnc2s1] | MS (m/z): 301 (M + 1). |

Preparation 207

1-(4-chlorobenzo[b]thiophen-2-yl)ethanone

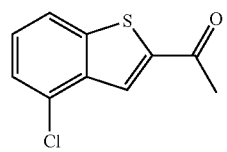

Add a solution of CH$_3$MgBr (3 M in THF, 1.7 ml, 4.99 mmol) to a suspension of 4-chloro-N-methoxy-N-methyl-benzo[b]thiophene-2-carboxamide (0.85 g, 3.33 mmol) in dry THF (10 mL) at 0° C. Then stir the mixture for overnight at ambient temperature. Quench the reaction with saturated NH$_4$Cl aqueous solution (15 mL) and extract the aqueous mixture with EtOAc (10 mL×3). The combined organic layers are washed with brine, dried over anhydrous Na$_2$SO$_4$ and concentrated under vacuum. Purify the residue by silica gel chromatograph (PE:EtOAc=6:1) to afford 1-(4-chlorobenzo[b]thiophen-2-yl)ethanone as white solid (0.6 g, 86.9%). $^1$H NMR (400 MHz, CDCl$_3$) δ 8.10-8.07 (s, 1H), 7.75 (d, J=5.2, 1H), 7.47-7.36 (m, 2H), 2.72-2.68 (s, 3H).

The following compounds are prepared essentially by the method of Preparation 207.

| Prep. No. | Chemical name | Structure | Physical data |
|---|---|---|---|
| 208 | 1-Thieno[2,3-c]pyridin-2-yl-ethanone | 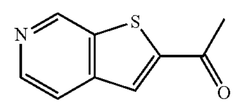 | MS (m/z): 178 (M + 1). |
| 209 | 1-(5-Bromo-thieno[2,3-b]pyridin-2-yl)-ethanone | 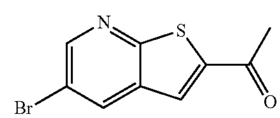 | MS (m/z): 258 (M + 1). |

-continued

| Prep. No. | Chemical name | Structure | Physical data |
|---|---|---|---|
| 210 | 1-Thieno[2,3-b]pyridin-2-yl-ethanone | 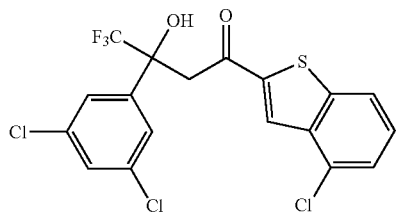 [SMILES: O=C(CC(O)(c1cc(Cl)cc(Cl)c1)C(F)(F)F)c1cc2c(Cl)cccc2s1] | MS (m/z): 178 (M + 1). |

Preparation 211

1-(4-chlorobenzo[b]thiophen-2-yl)-3-(3,5-dichlorophenyl)-4,4,4-trifluoro-3-hydroxybutan-1-one Add a solution of LiHMDS (1 M in THF, 4.3 ml, 4.31 mmol) to a mixture of 1-(4-chlorobenzo[b]thiophen-2-yl)ethanone (0.6 g, 2.87 mmol) in dry THF (10 mL) at −78° C. under N₂. After stirring 1.5 hour at −78° C., add 1-(3,5-dichlorophenyl)-2,2,2-trifluoroethanone (836 mg, 3.44 mmol) to the reaction mixture and stir the resultant mixture for additional 2 hours. Quench the reaction with saturated NH₄Cl solution and extract the aqueous mixture with EtOAc (10 mL×3). The combined organic layers are washed with brine, dried over anhydrous Na₂SO₄ and concentrated under vacuum afford crude 1-(4-chlorobenzo[b]thiophen-2-yl)-3-(3,5-dichlorophenyl)-4,4,4-trifluoro-3-hydroxybutan-1-one as brown solid (1.1 g, 84.6%). ¹H NMR (400 MHz, CDCl₃) δ 8.10-8.07 (s, 1H), 7.75 (d, J=5.2, 1H), 7.47-7.36 (m, 2H), 2.72-2.68 (s, 3H).

The following compounds are prepared essentially by the method of Preparation 211.

| Prep. No. | Chemical name | Structure | Physical data |
|---|---|---|---|
| 212 | 3-(3,5-Dichloro-phenyl)-4,4,4-trifluoro-3-hydroxy-1-thieno[2,3-c]pyridin-2-yl-butan-1-one | 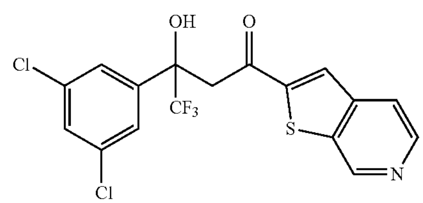 [SMILES: O=C(CC(O)(c1cc(Cl)cc(Cl)c1)C(F)(F)F)c1cc2ccncc2s1] | MS (m/z): 418 (M − 1) |
| 213 | 3-(3,5-Dichloro-phenyl)-4,4,4-trifluoro-3-hydroxy-1-(5-bromo-thieno[2,3-b]pyridin-2-yl)-butan-1-one | 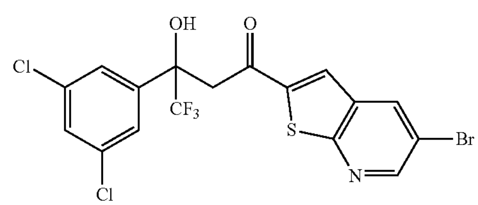 [SMILES: O=C(CC(O)(c1cc(Cl)cc(Cl)c1)C(F)(F)F)c1cc2cc(Br)cnc2s1] | MS (m/z): 498 (M − 1). |
| 214 | 3-(3,5-Dichloro-phenyl)-4,4,4-trifluoro-3-hydroxy-1-thieno[2,3-b]pyridin-2-yl-butan-1-one | 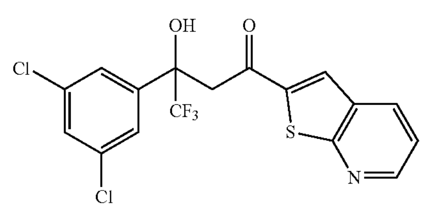 [SMILES: O=C(CC(O)(c1cc(Cl)cc(Cl)c1)C(F)(F)F)c1cc2cccnc2s1] | MS (m/z): 418 (M − 1). |
| 215 | 1-(benzo[d]thiazol-2-yl)-3-(3,5-dichlorophenyl)-4,4,4-trifluoro-3-hydroxybutan-1-one | 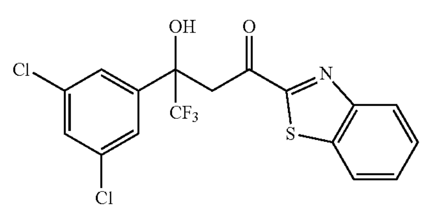 [SMILES: O=C(CC(O)(c1cc(Cl)cc(Cl)c1)C(F)(F)F)c1nc2ccccc2s1] | MS (m/z): 418 (M − 1). |

| Prep. No. | Chemical name | Structure | Physical data |
|---|---|---|---|
| 216 | 3-(3,5-dichlorophenyl)-4,4,4-trifluoro-3-hydroxy-1-(3-methylbenzo[b]thiophen-2-yl)butan-1-one | 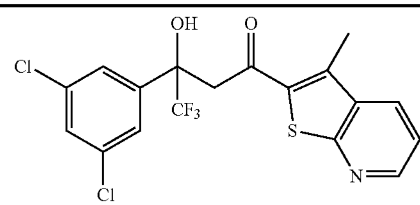 | MS (m/z): 431 (M − 1). |
| 217 | 3-(3,5-dichlorophenyl)-4,4,4-trifluoro-3-hydroxy-1-(5-methylbenzo[b]thiophen-2-yl)butan-1-one | 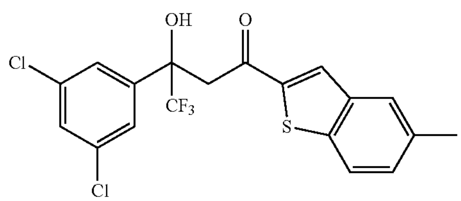 [SMILES: Cc1ccc2sc(C(=O)CC(O)(c3cc(Cl)cc(Cl)c3)C(F)(F)F)cc2c1] | MS (m/z): 431 (M − 1). |
| 218 | 1-(5-chlorobenzo[b]thiophen-2-yl)-3-(3,5-dichlorophenyl)-4,4,4-trifluoro-3-hydroxybutan-1-one | 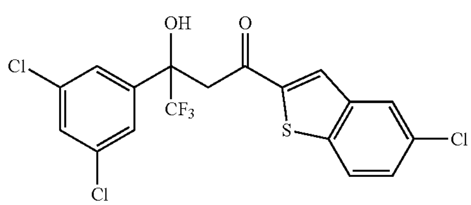 [SMILES: O=C(CC(O)(c1cc(Cl)cc(Cl)c1)C(F)(F)F)c1cc2cc(Cl)ccc2s1] | MS (m/z): 451 (M − 1). |
| 219 | 1-(benzo[b]thiophen-2-yl)-3-(3,5-dichlorophenyl)-4,4,4-trifluoro-3-hydroxybutan-1-one | 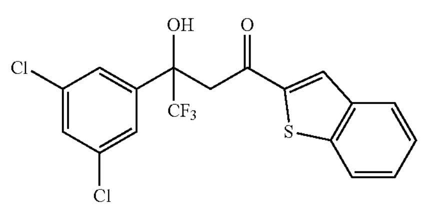 [SMILES: O=C(CC(O)(c1cc(Cl)cc(Cl)c1)C(F)(F)F)c1cc2ccccc2s1] | MS (m/z): 417 (M − 1). |

Preparation 220

1-(4-chlorobenzo[b]thiophen-2-yl)-3-(3,5-dichlorophenyl)-4,4,4-trifluorobut-2-en-1-one

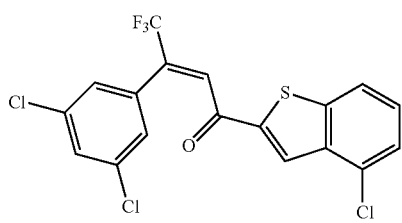 [SMILES: O=C(/C=C(\c1cc(Cl)cc(Cl)c1)C(F)(F)F)c1cc2c(Cl)cccc2s1]

Stir a mixture of 1-(4-chlorobenzo[b]thiophen-2-yl)-3-(3,5-dichlorophenyl)-4,4,4-trifluoro-3-hydroxybutan-1-one (1.1 g, crude, 2.43 mmol), $SOCl_2$ (1.16 g, 0.7 mL, 9.43 mmol) and pyridine (384 mg, 0.4 mL, 4.86 mmol) in anhydrous DCM (10 mL) at ambient temperature for overnight. Dilute the mixture with saturated $NH_4Cl$ solution and extract the aqueous mixture with DCM (10 mL×3). The combined organic layers are washed with brine, dried over anhydrous $Na_2SO_4$ and concentrated under vacuum to afford crude 1-(4-chlorobenzo[b]thiophen-2-yl)-3-(3,5-dichlorophenyl)-4,4,4-trifluorobut-2-en-1-one as brown solid (1.05 g, 100%). $^1$H NMR (400 MHz, $CDCl_3$) δ8.12-8.10 (s, 1H), 7.69-7.64 (m, 1H), 7.47-7.44 (m, 2H), 7.38-7.35 (m, 2H), 7.27-7.24 (m, 1H), 6.96-6.92 (s, 1H).

The following compounds are prepared essentially by the method of Preparation 220.

| Prep. No. | Chemical name | Structure | Physical data |
|---|---|---|---|
| 221 | 3-(3,5-Dichloro-phenyl)-4,4,4-trifluoro-1-thieno[2,3-c]pyridin-2-yl-but-2-en-1-one | 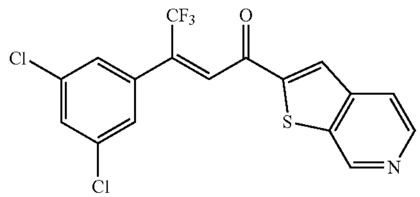 [SMILES: O=C(/C=C(/c1cc(Cl)cc(Cl)c1)C(F)(F)F)c1cc2ccncc2s1] | MS (m/z): 400 (M − 1). |
| 222 | 3-(3,5-Dichloro-phenyl)-4,4,4-trifluoro-1-(5-bromo-thieno[2,3-b]pyridin-2-yl)-but-2-en-1-one | 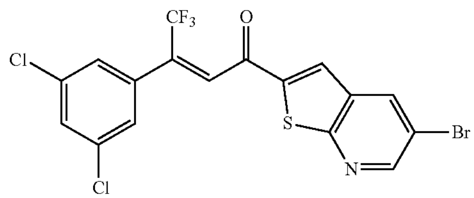 [SMILES: O=C(/C=C(/c1cc(Cl)cc(Cl)c1)C(F)(F)F)c1cc2cc(Br)cnc2s1] | MS (m/z): 480 (M − 1). |
| 223 | 3-(3,5-Dichloro-phenyl)-4,4,4-trifluoro-1-thieno[2,3-b]pyridin-2-yl-but-2-en-1-one | 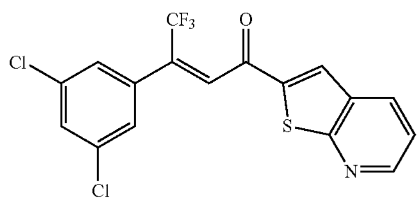 [SMILES: O=C(/C=C(/c1cc(Cl)cc(Cl)c1)C(F)(F)F)c1cc2cccnc2s1] | MS (m/z): 400 (M − 1). |
| 224 | 1-(benzo[b]thiophen-2-yl)-3-(3,5-dichloro-phenyl)-4,4,4-trifluoro-but-2-en-1-one | 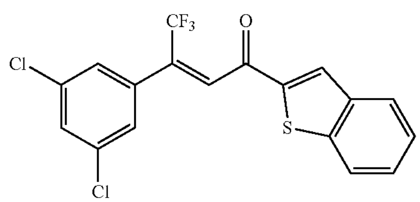 [SMILES: O=C(/C=C(/c1cc(Cl)cc(Cl)c1)C(F)(F)F)c1cc2ccccc2s1] | MS (m/z): 399 |
| 225 | 1-(benzo[d]thiazol-2-yl)-3-(3,5-dichlorophenyl)-4,4,4-trifluorobut-2-en-1-one | 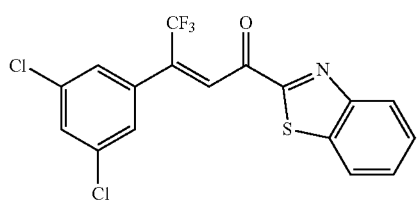 [SMILES: O=C(/C=C(/c1cc(Cl)cc(Cl)c1)C(F)(F)F)c1nc2ccccc2s1] | MS (m/z): 400 |
| 226 | 3-(3,5-dichlorophenyl)-4,4,4-trifluoro-1-(3-methylbenzo[d]thiophen-2-yl)but-2-en-1-one | 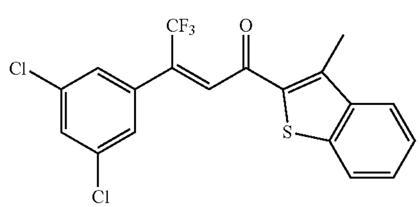 [SMILES: Cc1c(C(=O)/C=C(/c2cc(Cl)cc(Cl)c2)C(F)(F)F)sc2ccccc12] | MS (m/z): 413 |
| 227 | 3-(3,5-dichlorophenyl)-4,4,4-trifluoro-1-(5-methylbenzo[b]thiophen-2-yl)but-2-en-1-one | 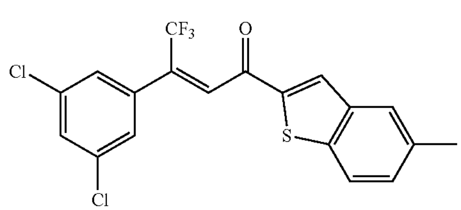 [SMILES: Cc1ccc2sc(C(=O)/C=C(/c3cc(Cl)cc(Cl)c3)C(F)(F)F)cc2c1] | MS (m/z): 413 |

-continued

| Prep. No. | Chemical name | Structure | Physical data |
|---|---|---|---|
| 228 | 1-(5-chlorobenzo[b]thiophen-2-yl)-3-(3,5-dichlorophenyl)-4,4,4-trifluorobut-2-en-1-one | 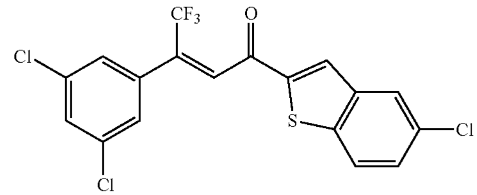 [SMILES: O=C(/C=C(/c1cc(Cl)cc(Cl)c1)C(F)(F)F)c1cc2cc(Cl)ccc2s1] | MS (m/z): 433 |

Example 229

3-(4-chlorobenzo[b]thiophen-2-yl)-5-(3,5-dichlorophenyl)-5-(trifluoromethyl)-4,5-dihydroisoxazole

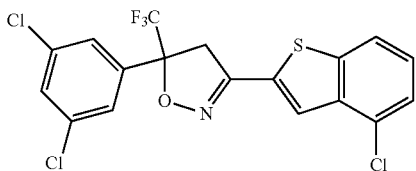 [SMILES: FC(F)(F)C1(c2cc(Cl)cc(Cl)c2)CC(c2cc3c(Cl)cccc3s2)=NO1]

Stir a mixture of 1-(4-chlorobenzo[b]thiophen-2-yl)-3-(3,5-dichlorophenyl)-4,4,4-trifluorobut-2-en-1-one (1.05 g, crude, 2.43 mmol), NaOH (389 mg, 9.72 mmol) and $NH_2OH\cdot HCl$ (335 mg, 4.8 mmol) in MeOH (8 mL) and water (8 mL) at ambient temperature for 4 hours. After removal of solvent under vacuum, dilute the residue with ice water (20 mL). Extract the aqueous mixture with EtOAc (15 mL×3). The combined organic layers are washed with brine, dried over anhydrous $Na_2SO_4$ and concentrated under vacuum. Purify the residue by preparative HPLC to afford 3-(4-chlorobenzo[b]thiophen-2-yl)-5-(3,5-dichlorophenyl)-5-(trifluoromethyl)-4,5-dihydroisoxazole as white solid (305 mg, 28.1%). MS (m/z): 450 (M+1). $^1$H NMR (400 MHz, $CDCl_3$) δδ 7.74 (d, J=8.0, 1H), 7.64-7.60 (s, 1H), 7.57-7.53 (m, 2H), 7.47-7.43 (m, 1H), 7.40-7.32.

The following compounds are prepared essentially by the method of Example 229.

| Ex. No. | Chemical name | Structure | Physical data |
|---|---|---|---|
| 230 | 2-[5-(3,5-Dichlorophenyl)-5-trifluoromethyl-4,5-dihydro-isoxazol-3-yl]-thieno[2,3-c]pyridine | 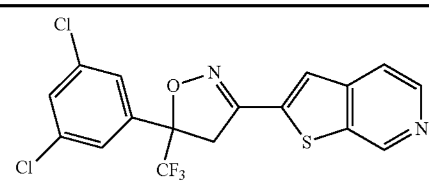 | MS (m/z): 417 (M + 1). $^1$H NMR (400 MHz, $CDCl_3$) δ 9.17 (s, 1H), 8.55-8.57 (d, J = 5.6, 1H), 7.68-7.69 (d, $J_1$ = 5.6, $J_2$ = 1.2, 1H), 7.51-7.52 (d, J = 1.2, 2H), 7.49 (S, 1H), 7.45-7.46 (t, J = 3.6, 1H), 4.17-4.21 (d, J = 16.8, 1H), 3.79-3.83 (d, J = 16.8, 1H). |
| 231 | 5-Bromo-2-[5-(3,5-dichloro-phenyl)-5-trifluoromethyl-4,5-dihydro-isoxazol-3-yl]-thieno[2,3-b]pyridine | 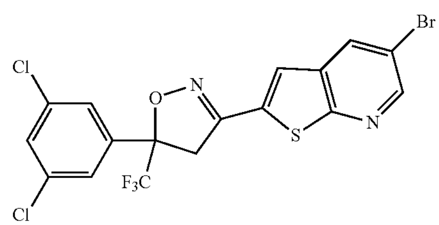 [SMILES: FC(F)(F)C1(c2cc(Cl)cc(Cl)c2)CC(c2cc3cc(Br)cnc3s2)=NO1] | MS (m/z): 497 (M + 1). 1H NMR (400 MHz, $CDCl_3$) δ 8.65-8.66 (d, J = 1.6, 1H ), 8.18-8.19 (d, J = 2.0, 1H), 7.51 (S, 2H), 7.45-7.46 (d, J = 1.6, 1H), 7.32 (S, 1H),4.13-4.17 (d, J = 16.8, 1H), 3.75-3.79 (d, J = 16.8, 1H). |
| 232 | 2-[5-(3,5-Dichlorophenyl)-5-trifluoromethyl-4,5-dihydro-isoxazol-3-yl]-thieno[2,3-b]pyridine | 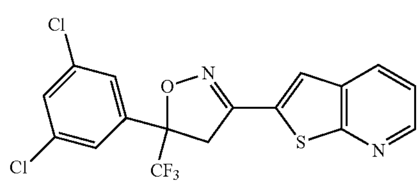 [SMILES: FC(F)(F)C1(c2cc(Cl)cc(Cl)c2)CC(c2cc3cccnc3s2)=NO1] | MS (m/z): 417 (M + 1). $^1$H NMR (400 MHz, $CDCl_3$) δ 8.62-8.64 (d, $J_1$ = 4.4, $J_2$ = 1.6, 1H), 8.05-8.07 (d, $J_1$ = 8.0, $J_2$ = 1.6, 1H), 7.51-7.52 (d, J = 1.2, 2H), 7.44-7.45 (t, J = 3.6, 1H), 7.41 (s, 1H), 7.33-7.36 (m, 1H), 4.15-4.19 (d, J = 16.8, 1H), 3.77-3.81 (d, J = 16.8, 1H). |
| 233 | 3-(benzo[b]thiophen-2-yl)-5-(3,5-dichlorophenyl)-5-(trifluoromethyl)-4,5-dihydroisoxazole | 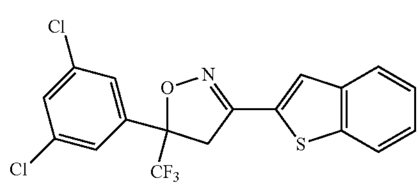 [SMILES: FC(F)(F)C1(c2cc(Cl)cc(Cl)c2)CC(c2cc3ccccc3s2)=NO1] | MS (m/z): 416 (M + 1). 1H NMR (400 MHz, $CDCl_3$) δ 7.84 (d, J = 8.0, 1H), 7.82 (d, J = 8.0, 1H), 7.55-7.50 (m, 2H), 7.48-7.34 (m, 4H), 4.20 (d, J = 16.8, 1H), 3.80 (d, J = 17.6, 1H). |

-continued

| Ex. No. | Chemical name | Structure | Physical data |
|---|---|---|---|
| 234 | 3-(benzo[d]thiazol-2-yl)-5-(3,5-dichlorophenyl)-5-(trifluoromethyl)-4,5-dihydroisoxazole | 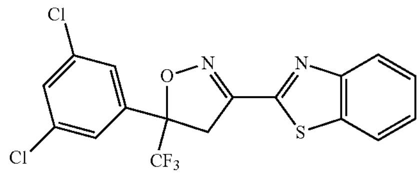 [SMILES: FC(F)(F)C1(c2cc(Cl)cc(Cl)c2)CC(c2nc3ccccc3s2)=NO1] | MS (m/z): 417 (M + 1). 1H NMR (400 MHz, CDCl$_3$) δ 8.07 (d, J = 7.2, 1H), 7.93 (d, J = 7.2, 1H), 7.58-7.47 (m, 5H), 4.37 (d, J = 18.0, 1H), 4.00 (d, J = 18.0, 1H) |
| 235 | 5-(3,5-dichlorophenyl)-3-(3-methylbenzo[b]thiophen-2-yl)-5-(trifluoromethyl)-4,5-dihydroisoxazole | 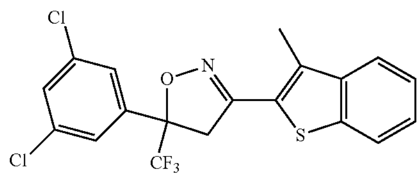 [SMILES: Cc1c(C2=NOC(c3cc(Cl)cc(Cl)c3)(C(F)(F)F)C2)sc2ccccc12] | MS (m/z): 430 (M + 1). 1H NMR (400 MHz, CDCl$_3$) δ 7.83-7.78 (m, 2H), 7.53 (s, 2H), 7.53-7.43 (m, 3H), 4.17 (d, J = 16.8, 1H), 3.79 (d, J = 16.8, 1H), 2.67 (s, 3H). |
| 236 | 5-(3,5-dichlorophenyl)-3-(5-methylbenzo[b]thiophen-2-yl)-5-(trifluoromethyl)-4,5-dihydroisoxazole | 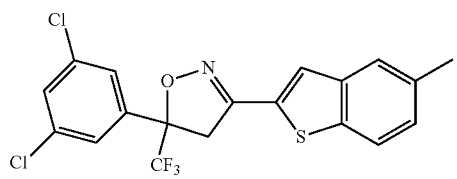 [SMILES: Cc1ccc2sc(C3=NOC(c4cc(Cl)cc(Cl)c4)(C(F)(F)F)C3)cc2c1] | MS (m/z): 430 (M + 1). 1H NMR (400 MHz, CDCl$_3$) δ 7.71 (d, J = 8.0, 1H), 7.57 (s, 1H), 7.53 (s, 2H), 7.43 (t, J = 3.2, 1H), 7.36 (d, J = 7.0, 1H), 7.24 (d, J = 7.0, 1H), 4.17 (d, J = 16.8, 1H), 3.78 (d, J = 16.8, 1H), 2.47 (s, 3H). |
| 237 | 3-(5-chlorobenzo[b]thiophen-2-yl)-5-(3,5-dichlorophenyl)-5-(trifluoromethyl)-4,5-dihydroisoxazole | 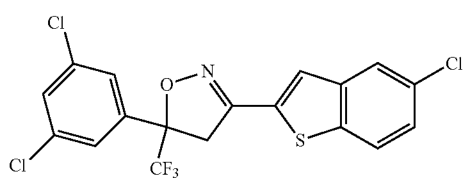 [SMILES: FC(F)(F)C1(c2cc(Cl)cc(Cl)c2)CC(c2cc3cc(Cl)ccc3s2)=NO1] | MS (m/z): 450 (M + 1). 1H NMR (400 MHz, CDCl$_3$) δ 7.76-7.75 (m, 2H), 7.51 (s, 2H), 7.45-7.44 (m, 1H), 7.40-7.38 (m, 2H), 4.18 (d, J = 16.8, 1H), 3.78 (d, J = 17.6, 1H). |

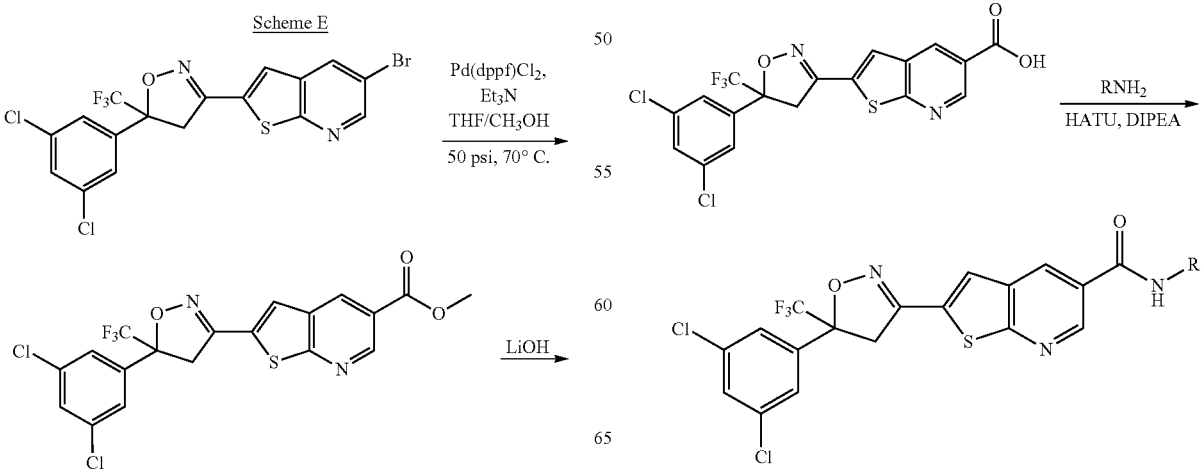

Scheme E

Preparation 238 methyl 2-(5-(3,5-dichlorophenyl)-5-(trifluoromethyl)-4,5-dihydroisoxazol-3-yl)thieno[2,3-b]pyridine-5-carboxylate

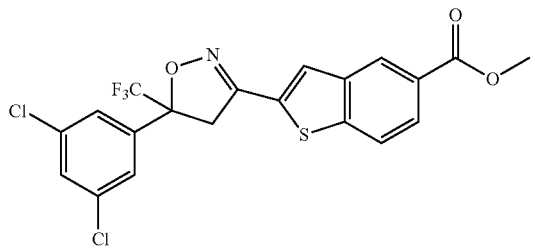 [SMILES: COC(=O)c1ccc2sc(C3=NOC(c4cc(Cl)cc(Cl)c4)(C(F)(F)F)C3)cc2c1]

Stir a mixture of 5-bromo-2-[5-(3,5-dichloro-phenyl)-5-trifluoromethyl-4,5-dihydro-isoxazol-3-yl]-thieno[2,3-b]pyridine (494 mg, 1 mmol), Pd(dppf)Cl$_2$ (100 mg) and triethyl amine (1 mL) in anhydrous THF (10 mL) and methanol (5 mL) under carbon monoxide (50 psi) at 70° C. for 10 h. After removal of solvent under vacuum, purify the residue with silica gel chromatography (eluting with 10% ethyl acetate in petroleum ether) to afford methyl 2-(5-(3,5-dichlorophenyl)-5-(trifluoromethyl)-4,5-dihydroisoxazol-3-yl)thieno[2,3-b]pyridine-5-carboxylate as a white solid (210 mg, 44.18%). MS (m/z): 475 (M+1).

Preparation 239

2-[5-(3,5-Dichloro-phenyl)-5-trifluoromethyl-4,5-dihydro-isoxazol-3-yl]-thieno[2,3-b]pyridine-5-carboxylic acid

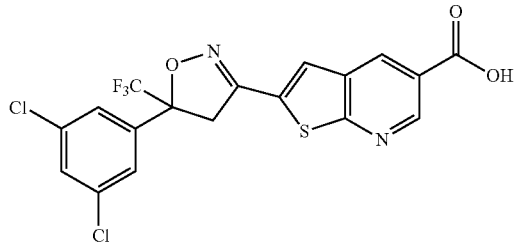 [SMILES: O=C(O)c1cnc2sc(C3=NOC(c4cc(Cl)cc(Cl)c4)(C(F)(F)F)C3)cc2c1]

Add a solution of LiOH—H$_2$O (76 mg, 2 mmol) in water (0.5 mL) to a solution of methyl 2-(5-(3,5-dichlorophenyl)-5-(trifluoromethyl)-4,5-dihydroisoxazol-3-yl)thieno[2,3-b]pyridine-5-carboxylate (237 mg, 0.5 mmol) in THF (3 mL). Stir the mixture at temperature for 12 hours. After addition of 10 mL of water, acidify the mixture with concentrated HCl to PH=6~7. Extract the resultant mixture with ethyl acetate (3×10 mL). The combined organic layers are washed brine, dried over anhydrous Na$_2$SO$_4$ and concentrated under vacuum to afford 2-[5-(3,5-Dichloro-phenyl)-5-trifluoromethyl-4,5-dihydro-isoxazol-3-yl]-thieno[2,3-b]pyridine-5-carboxylic acid as pale yellow solid (170 mg, 73.9%), which is used in next step without further purification. MS (m/z): 461 (M+1).

Example 240

2-(5-(3,5-dichlorophenyl)-5-(trifluoromethyl)-4,5-dihydroisoxazol-3-yl)-N-(2-oxo-2-(2,2,2-trifluoroethylamino)ethyl)thieno[2,3-b]pyridine-5-carboxamide

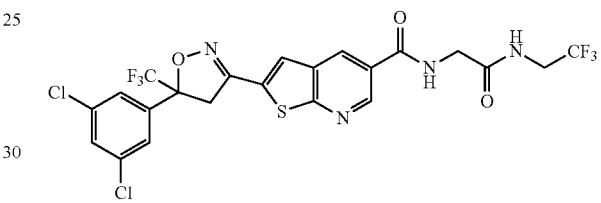

Stir a mixture of 2-Amino-N-(2,2,2-trifluoro-ethyl)-acetamide (156 mg, 1 mmol), 2-[5-(3,5-dichloro-phenyl)-5-trifluoromethyl-4,5-dihydro-isoxazol-3-yl]-thieno[2,3-b]pyridine-5-carboxylic acid (160 mg, 0.24 mmol), HATU (150 mg, 0.39 mmol) and DIPEA (0.2 mL) at room temperature for 10 hours. After removal of solvent, purify the mixture by preparative-HPLC to afford 2-(5-(3,5-dichlorophenyl)-5-(trifluoromethyl)-4,5-dihydroisoxazol-3-yl)-N-(2-oxo-2-(2,2,2-trifluoroethylamino)ethyl)thieno[2,3-b]pyridine-5-carboxamide as a white solid (50 mg, 34.78%). MS (m/z): 599 (M+1). $^1$H NMR (400 MHz, CDCl$_3$) δ 9.02 (s, 1H), 8.51 (s, 1H), 7.52 (s, 2H), 7.44-7.41 (m, 2H), 7.22 (s, 1H), 6.64 (s, 1H), 4.27 (d, J=5.2, 2H), 4.17 (d, J=16.8, 1H), 4.04-3.95 (m, 2H), 3.80 (d, J=16.08, 1H).

The following compound is prepared essentially by the method of Example 240.

| Ex. No. | Chemical name | Structure | Physical data |
|---|---|---|---|
| 241 | 2-(5-(3,5-dichlorophenyl)-5-(trifluoromethyl)-4,5-dihydroisoxazol-3-yl)-N-((R)-2-oxopyrrolidin-3-yl)thieno[2,3-b]pyridine-5-carboxamide | 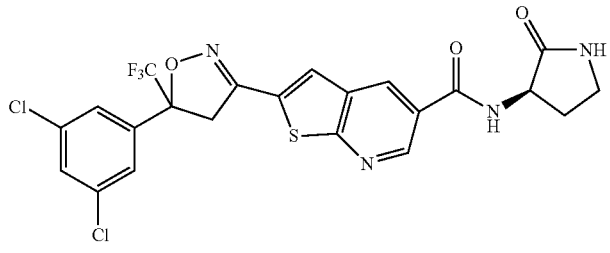 [SMILES: O=C(N[C@@H]1CCNC1=O)c1cnc2sc(C3=NOC(c4cc(Cl)cc(Cl)c4)(C(F)(F)F)C3)cc2c1] | MS (m/z): 543 (M + 1). $^1$H NMR (400 MHz, CDCl$_3$) δ 9.01 (s, 1H), 8.49 (s, 1H), 7.54 (s, 2H), 7.44-7.40 (m, 2H), 7.15 (S, 1H), 5.89 (s, 1H), 4.60 (s, 1H), 4.18 (d, J = 16.8, 1H), 3.80 (d, J = 16.8, 1H), 3.51-3.48 (m, 2H), 3.00-2.93 (m, 1H), 2.14-2.08 (m, 1H) |

Scheme F

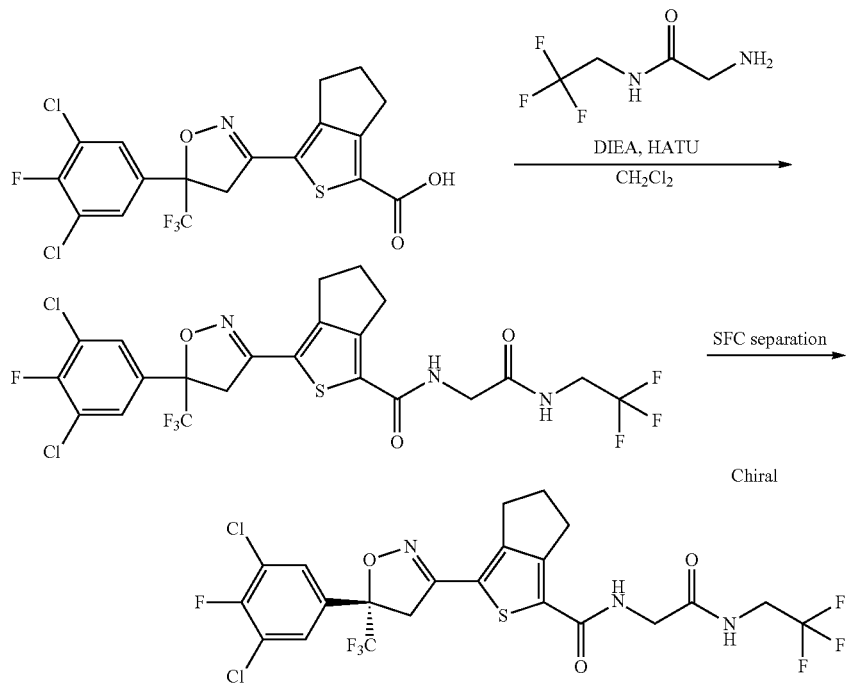

Example 242

3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide Example 243

(S)-3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide

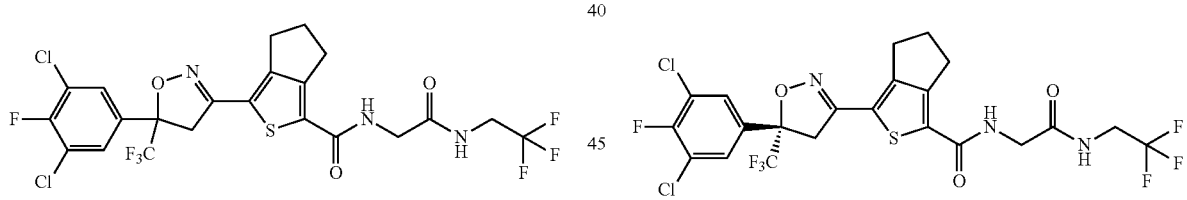

Stir a mixture of 3-(5-(3,5-dichloro-4-fluorophenyl)-5-(trifluoromethyl)-4,5-dihydroisoxazol-3-yl)-5,6-dihydro-4H-cyclopenta[c]thiophene-1-carboxylic acid (1.0 g, 2.14 mmol), N,N-diisopropylethylamine (827 mg, 6.41 mmol), 2-amino-N-(2,2,2-trifluoroethyl) acetamide hydrochloride (658 mg, 2.56 mmol) and HATU (1.2 g, 3.2 mmol) in $CH_2Cl_2$ (10 mL) at room temperature for 2 hours. The reaction mixture is diluted with $CH_2Cl_2$ (50 mL) and is washed with water (10 mL×3) and brine. Then the organic layer is dried over anhydrous $Na_2SO_4$ and is concentrated under vacuum. Purify the residue by preparative HPLC to afford 3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide as a white solid (1.1 g, 84.6%). MS (m/z): 606.0 (M+1).

1 g of 3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide is separated by SFC to give (S)-3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide (400 mg, 80% yield, 100% ee).

$^1$H NMR (400 MHz, $CDCl_3$) δ 7.56 (d, J=6.0, 2H), 6.92 (t, J=6.4, 1H), 6.76 (t, J=4.8, 1H), 4.21 (d, J=4.8, 2H), 3.98 (m, 3H), 3.61 (d, J=16.8, 1H), 2.97 (t, J=7.6, 2 H), 2.89 (t, J=7.6, 2H), 2.55 (m, 2H). MS (m/z): 606.0 (M+1).

SFC analysis condition: Column: Chiralcel AD-H 250×4.6 mm I.D., 5 um. Mobile phase: ethanol in $CO_2$ from 5% to 40% over 3 minutes. Flow rate: 2.35 mL/min. Wavelength: 220 nm. The S-isomer elutes at 1.4 minutes. SFC separation condition: Instrument: Thar SFC 80; Column: AD 250 mm*20 mm, 20 um; Mobile phase: A: Supercritical $CO_2$, B: MeOH (0.05% NH$_3$H$_2$O), A:B=45:55 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm
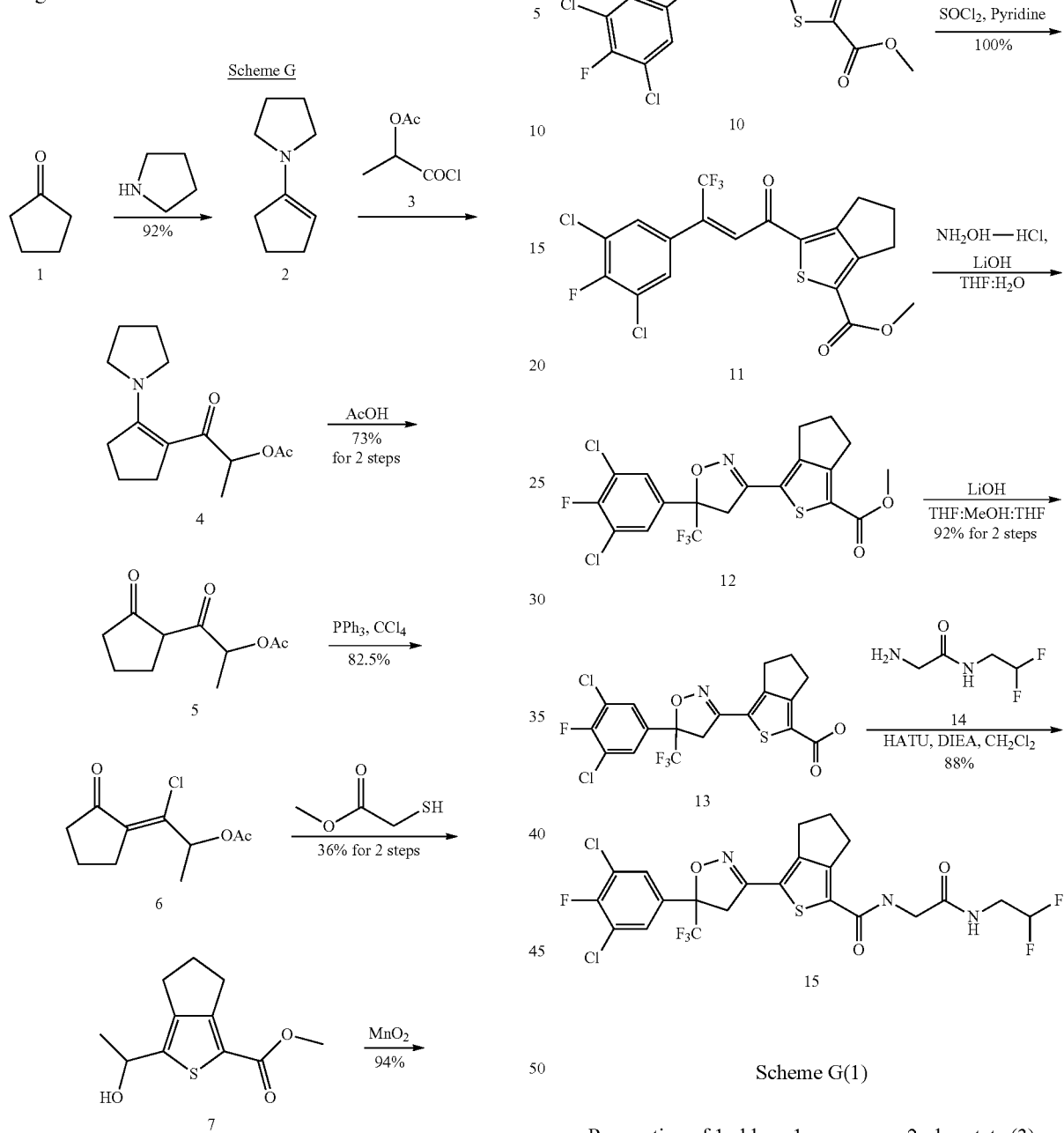
Scheme G(1)
Preparation of 1-chloro-1-oxopropan-2-yl acetate (3)
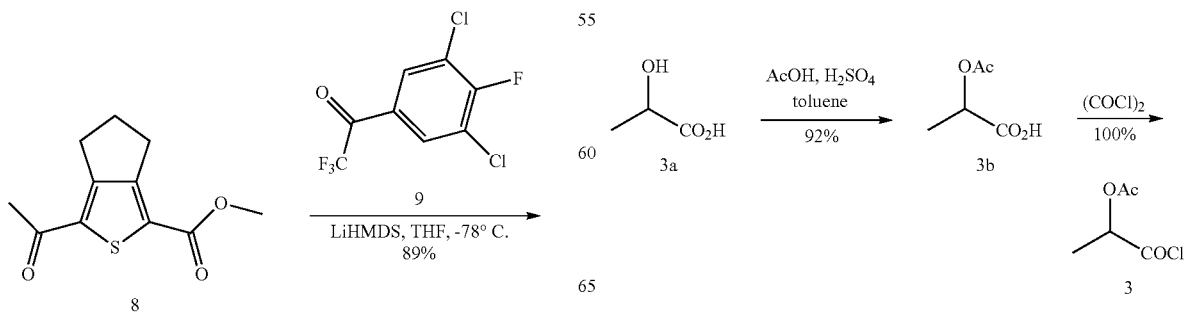

Scheme G(2)

Synthesis of 2-amino-N-(2,2-difluoro-ethyl) acetamide hydrochloride

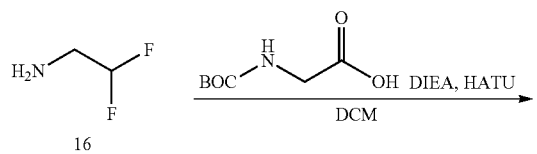

16

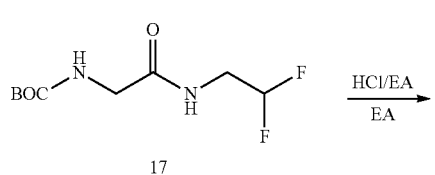

17

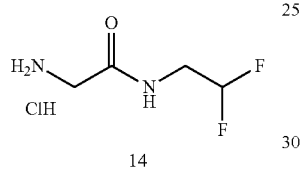

14

Scheme G(3)

Synthesis of 3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide

Example 244

3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide

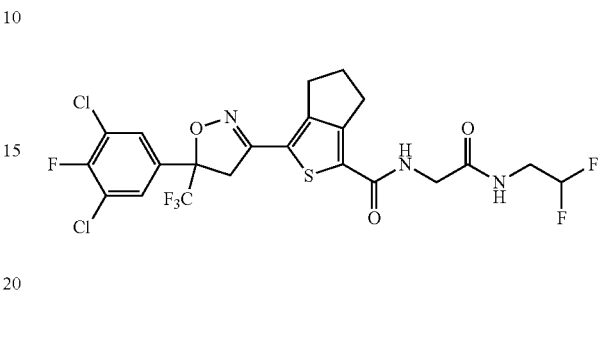

A) Synthesis of 2-acetoxy-propionic acid

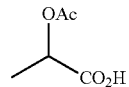

Reflux a mixture of 2-hydroxy-propionic acid (480 ml, 85% in water) and sulfuric acid (2 mL) in acetic acid (2500 mL) and toluene (300 mL) for overnight. After removal of solvent under vacuum, purify the residue by distillation to give 2-acetoxy-propionic acid (550 g, 92%) as colorless oil. $^1$H NMR (CDCl$_3$, 400 MHz): δ 9.27 (brs, 1H), 5.10 (m, 1H), 2.13 (s, 3H), 1.53 (d, J=7.2, 3H).

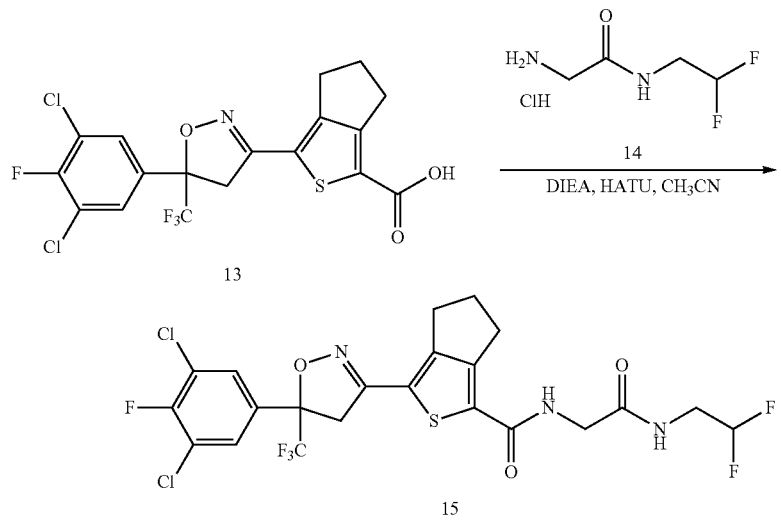

B) Synthesis of 1-chloro-1-oxopropan-2-yl acetate

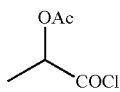

Stir a mixture of 2-acetoxy-propionic acid (550 g, 4.16 mol) in oxalyl chloride (500 mL) at room temperature for overnight. After removal of oxalyl chloride under vacuum, ~700 g crude product is obtained (quantitative yield crude), which is used directly in the next step. $^1$H NMR (CDCl$_3$, 400 MHz): δ 5.16 (m, 1H), 2.13 (s, 3H), 1.58 (d, J=7.2, 3H).

C) Synthesis of 1-cyclopentenylpyrrolidine

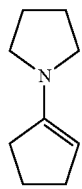

Reflux a mixture of cyclopentanone (600 g, 7.14 mol), pyrrolidine (550 g, 4.68 mol) and toluene-4-sulfonic acid (5.0 g) in toluene (3 L) for 4 hours. After removal of solvent under vacuum, purify the residue by distillation carefully to give 1-cyclopent-1-enyl-pyrrolidine as colorless oil (898 g, 6.55 mol, 91.8%). $^1$H NMR (CDCl$_3$, 400 MHz): δ 4.04 (m, 1H), 3.06 (m, 4H), 2.39 (m, 4H), 1.85 (m, 6H).

D) Synthesis of 1-oxo-1-(2-(pyrrolidin-1-yl)cyclopent-1-enyl)propan-2-yl acetate

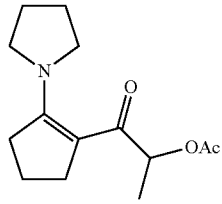 [SMILES: CC(=O)OC(C)C(=O)C1=C(N2CCCC2)CCC1]

Add dropwise a solution of 1-chloro-1-oxopropan-2-yl acetate (600 g, 3.98 mol) in toluene (1200 mL) to a solution of 1-cyclopent-1-enyl-pyrrolidine (546.7 g, 3.98 mol) and triethyl amine (483.9 g, 4.78 mol) in toluene (2400 mL). Reflux the mixture for overnight. Filter the mixture and concentrate the filtration to give crude 1-oxo-1-(2-(pyrrolidin-1-yl)cyclopent-1-enyl)propan-2-yl acetate (952 g), which is used in next step without further purification. $^1$H NMR (CDCl$_3$, 400 MHz): δ 5.27 (m, 1H), 3.56 (m, 2H), 3.16 (m, 2H), 2.83 (m, 1H), 2.58 (m, 3H), 2.10 (s, 3H), 1.93 (m, 2H), 1.82 (m, 4H), 1.36 (d, J=7.2, 3H).

E) Synthesis of 1-oxo-1-(2-oxocyclopentyl)propan-2-yl acetate

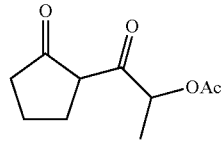

Stir a mixture of 1-oxo-1-(2-(pyrrolidin-1-yl)cyclopent-1-enyl)propan-2-yl acetate (952.0 g), acetic acid (1500 mL) and water (1500 mL) in tetrahydrofuran (3000 mL) at room temperature for 2 days. Dilute the mixture with water (1200 mL) and dichloromethane (1200 mL). The organic layer is washed with brine, dried over anhydrous Na$_2$SO$_4$ and concentrated under vacuum. Purify the residue by silica gel chromatograph (eluting with 3% to 10% ethyl acetate in petroleum ether) to give 1-oxo-1-(2-oxocyclopentyl)propan-2-yl acetate as oil (573.4 g, 2.89 mol, 72.6% for 2 steps).

F) Synthesis of 1-chloro-1-(2-oxocyclopentylidene)propan-2-yl acetate

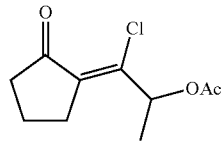

A mixture of 1-oxo-1-(2-oxocyclopentyl)propan-2-yl acetate (8.0 g, 0.04 mol) and tributylphosphane (13.9 g, 0.069 mol) in CCl$_4$ (100 mL) at 60° C. overnight. After removal of solvent, the residue is purified by silica gel column (eluting with 1% to 2.5% ethyl acetate in petroleum ether) to give a mixture of 1-chloro-1-(2-oxocyclopentylidene)propan-2-yl acetate and 1-(2-chlorocyclopent-1-enyl)-1-oxopropan-2-yl acetate (5.47 g, 6:1 based on HNMR) as yellow oil.

G) Synthesis of methyl 3-(1-hydroxyethyl)-5,6-dihydro-4H-cyclopenta[c]thiophene-1-carboxylate

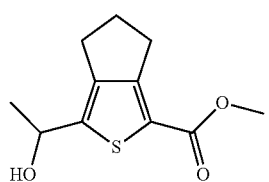

Add sodium hydride (60% in mineral oil, 2.12 g, 0.053 mol) to a solution of mercapto-acetic acid methyl ester (2.8 g, 0.026 mol) in tetrahydrofuran (100 mL) at −10° C.~0° C. and stirred the mixture at −10° C.~0° C. for 1 hour. Then add a mixture of 1-chloro-1-(2-oxocyclopentylidene)propan-2-yl acetate and 1-(2-chlorocyclopent-1-enyl)-1-oxopropan-2-yl acetate (5.47 g, 0.025 mol, 6:1) in tetrahydrofuran (15 mL) at 0° C. After stirring at 0° C. for overnight, dilute the reaction mixture with water and extract with ethyl acetate. The combined organic layers are washed with brine, dried over anhydrous Na$_2$SO$_4$ and concentrated. The residue and K$_2$CO$_3$ (6.9 g, 0.05 mol) in MeOH (20 mL) is heated at 50° C. overnight. The solvent is removed. The residue is purified by silica gel chromatograph (eluting with 2.5% to 10% ethyl acetate in petroleum ether) to give 3-(1-hydroxy-ethyl)-5,6-dihydro-4H-cyclopenta[c]thiophene-1-carboxylic acid methyl ester (3.2 g, 14.1 mmol, 35.6% for 2 steps) as yellow oil. $^1$H NMR (CDCl$_3$, 400 MHz): δ 5.03 (m, 1H), 3.83 (m, 3H), 2.88 (m, 2H), 2.66 (m, 2H), 2.38 (m, 2H), 2.12 (s, 1H), 1.54 (d, J=7.2, 3H).

H) Synthesis of methyl 3-acetyl-5,6-dihydro-4H-cyclopenta[c]thiophene-1-carboxylate

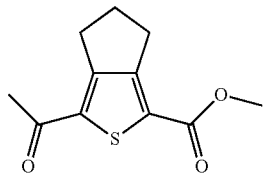

Reflux a mixture of 3-(1-Hydroxy-ethyl)-5,6-dihydro-4H-cyclopenta[c]thiophene-1-carboxylic acid methyl ester (3.2 g, 0.0141 mol) and manganese dioxide (10.8 g, 0.124 mol) in dichloromethane for 2 hours. Filter the hot reaction mixture solution and concentrate the filtration under vacuum. Purify the residue by silica gel chromatograph (eluting with 2% to 10% ethyl acetate in petroleum ether) to give 3-acetyl-5,6-dihydro-4H-cyclopenta[c]thiophene-1-carboxylic acid methyl ester as white solid (3.0 g, 13.39 mmol, 94.5%). $^1$H NMR (CDCl$_3$, 400 MHz): δ 3.88 (s, 3H), 2.96 (m, 4H), 2.50 (s, 3H), 2.45 (m, 2H).

I) Synthesis of 3-[3-(3,5-Dichloro-4-fluoro-phenyl)-4,4,4-trifluoro-3-hydroxy-butyryl]-5,6-dihydro-4H-cyclopenta[c]thiophene-1-carboxylic acid methyl ester

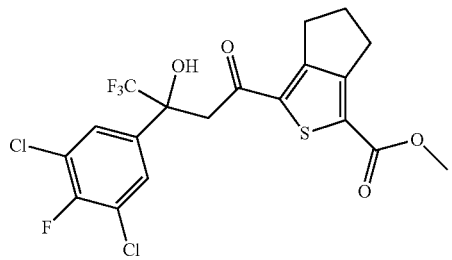 [SMILES: COC(=O)c1sc(C(=O)CC(O)(c2cc(Cl)c(F)c(Cl)c2)C(F)(F)F)c2c1CCC2]

Add a solution of LiHDMS (1M in THF, 75 mL, 75 mmol) to a suspension of 3-acetyl-5,6-dihydro-4H-cyclopenta[c]thiophene-1-carboxylic acid methyl ester (14.0 g, 62.5 mmol) in dry THF (200 mL) at −78° C. under N$_2$. After stirring at room temperature for 1.5 h, add 1-(3,5-dichloro-4-fluoro-phenyl)-2,2,2-trifluoro-ethanone (17.9 g, 68.7 mmol) in dry THF (100 mL) to the reaction mixture and stir the resultant mixture at the same temperature for additional 2 hours. Quench the reaction with saturated NH$_4$Cl aqueous solution. Extract the aqueous mixture with EtOAc (100 mL×3). The combined organic layers are washed with brine, dried over anhydrous Na$_2$SO$_4$ and concentrated under vacuum. Purify the residue by silica gel chromatograph (PE:EtOAc 15:1) to afford 3-[3-(3,5-Dichloro-4-fluoro-phenyl)-4,4,4-trifluoro-3-hydroxy-butyryl]-5,6-dihydro-4H-cyclopenta[c]thiophene-1-carboxylic acid methyl ester as an orange solid (27 g, 89.3%). MS (m/z): 486 (M+1).

J) Synthesis of 3-[3-(3,5-Dichloro-4-fluorophenyl)-4,4,4-trifluorobut-2-enoyl]-5,6-dihydro-4H-cyclopenta[c]thiophene-1-carboxylic acid methyl ester

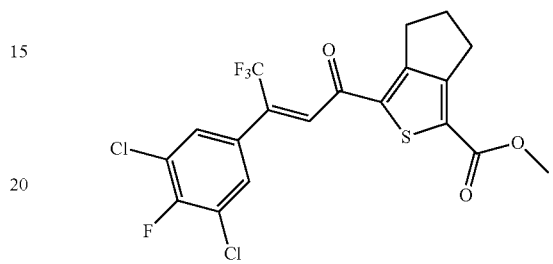

Stir a mixture of 3-[3-(3,5-Dichloro-4-fluoro-phenyl)-4,4,4-trifluoro-3-hydroxyl-butyryl]-5,6-dihydro-4H-cyclopenta[c]thiophene-1-carboxylic acid methyl ester (26 g, 53.7 mmol), SOCl$_2$ (12.7 g, 7.8 mL, 0.107 mmol) and pyridine (42.3 g, 0.537 mmol) in anhydrous DCM (300 mL) at room temperature for 3 hours. Concentrate the mixture under vacuum. Purify the residue by silica gel chromatograph (PE:EtOAc 12:1) to afford 3-[3-(3,5-Dichloro-4-fluoro-phenyl)-4,4,4-trifluoro-but-2-enoyl]-5,6-dihydro-4H-cyclopenta[c]thiophene-1-carboxylic acid methyl ester as a pale yellow solid (25 g, 100%). (m/z): 467 (M+1).

K) Synthesis of 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid methyl ester

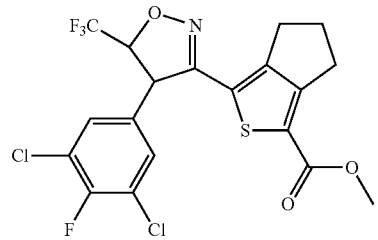 [SMILES: COC(=O)c1sc(C2=NOC(C(F)(F)F)C2c2cc(Cl)c(F)c(Cl)c2)c2c1CCC2]

Stir a mixture of 3-[3-(3,5-Dichloro-4-fluoro-phenyl)-4,4,4-trifluoro-but-2-enoyl]-5,6-dihydro-4H-cyclopenta[c]thiophene-1-carboxylic acid methyl ester (25 g, 53.6 mmol), NaOH (8.6 g, 0.214 mol) and NH$_2$OH—HCl (7.4 g, 0.107 mmol) in water (100 mL) and THF (200 mL) at room temperature for overnight. After removal of the solvent under vacuum, the solution is diluted with water and extracted with EtOAc (200 mL×3). The combined organic layer is washed with brine, dried over anhydrous Na2SO4 and concentrated by vacuum to afford 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid methyl ester as a white solid (26 g), which is used directly in the next step without purification. MS (m/z): 483 (M+1).

L) Synthesis of 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid

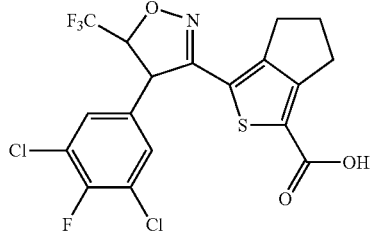 [SMILES: O=C(O)c1sc(C2=NOC(C(F)(F)F)C2c2cc(Cl)c(F)c(Cl)c2)c2c1CCC2]

Stir a mixture of 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid methyl ester (26 g, 54.1 mmol) and LiOH—H$_2$O (4.54 g, 0.108 mmol) in water (200 mL) and THF (400 mL) at 50° C. for 0.5 hour. After removal of organic solvent under vacuum, dilute the residue with ice water (100 mL). Acidify the aqueous mixture with conc. HCl to pH=1, and extract the resultant mixture with EtOAc (200 mL×3). Purify the residue by silica gel chromatograph (EtOAc:MeOH 6:1) to afford 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid as a white solid (23 g, 91.7% for 2 steps). MS (m/z): 468 (M+1).

M) Synthesis of [(2,2-difluoro-ethylcarbamoyl)-methyl]-carbamic acid tert-butyl ester

N)

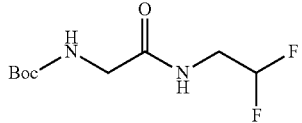 [SMILES: CC(C)(C)OC(=O)NCC(=O)NCC(F)F]

To a solution of compound tert-butoxycarbonylamino acetic acid (19.6 g, 0.1 mol) in dichloromethane (200 mL) is added N,N-diisopropylethylamine (13.2 g, 0.1 mol), 2,2-difluoroethylamine (10 g, 0.1 mol) and HATU (23 g, 0.17 mol), after the addition the mixture is stirred at room temperature for 1 hour. After being detected by TLC and LCMS, the reaction mixture is diluted with dichloromethane, then the solution is washed with water and brine, dried over anhydrous Na$_2$SO$_4$, filtered, concentrated and the residue is dried in vacuum to give 30 g crude product, which is used directly in next step.

O) Synthesis of 2-amino-N-(2,2-difluoro-ethyl) acetamide hydrochloride

P)

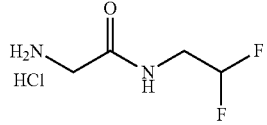

To a solution of compound [(2,2-difluoro-ethylcarbamoyl)-methyl]-carbamic acid tert-butyl ester (30 g crude product, 0.13 mol) in acetic acid ethyl ester (100 mL) is added 4 M HCl (100 mL, 4 mol/L in acetic acid ethyl ester) dropwise under ice-water bath. After the addition the reaction mixture is warmed to room temperature and stirred for overnight. The precipitate is collected and dried in vacuum to give desired product (20 g, 93% for two steps) as a white solid. $^1$H NMR (DMSO-d$_6$, 400 MHz): δ 8.91 (t, J=6.0, 1H), 8.25 (brs, 3H), 6.21-5.91 (m, 1H), 3.64-3.53 (m, 4H).

O) Synthesis of 3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide

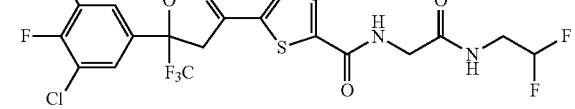

To a solution of compound 3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid (3 g, 6.4 mmol) in acetonitrile (30 mL) is added N,N-diisopropylethylamine (2.5 g, 19 mmol), 2-amino-N-(2,2-difluoroethyl)-acetamide hydrochloride (1.34 g, 7.7 mmol) and HATU (3.7 g, 9.6 mmol), after the addition the mixture is stirred at room temperature for 1 hour. After being detected by TLC and LCMS, the reaction mixture is concentrated and the residue is purified by column chromatography to afford desired product (3 g, 88%). MS (m/z): 588.1 (M+1).

Scheme H

SFC Separation of Example 244 to Provide S Form

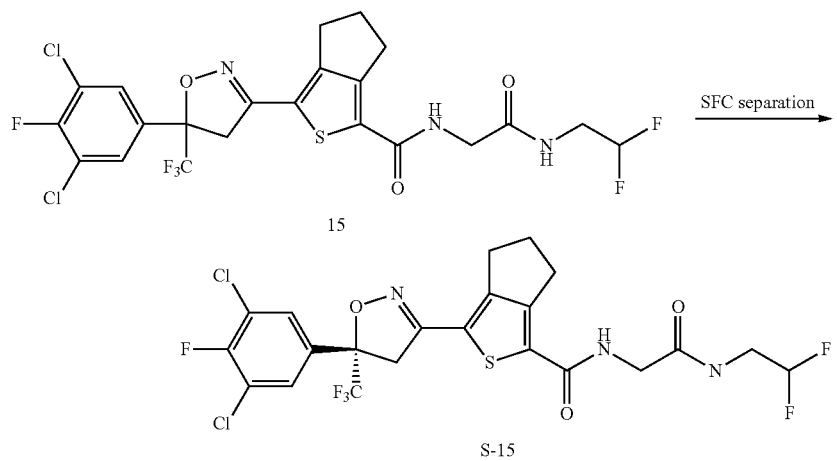

Example 245

(S)-3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide

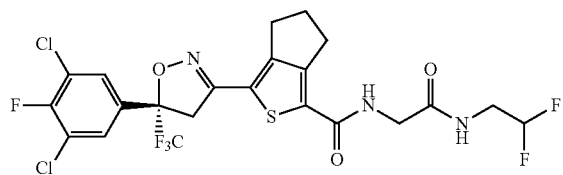 [SMILES: O=C(CNC(=O)c1sc(C2=NO[C@@](c3cc(Cl)c(F)c(Cl)c3)(C(F)(F)F)C2)c2c1CCC2)NCC(F)F]

3 g of 3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide is separated by SFC separation to give desired product (1.4 g, 93%).

1H NMR (CDCl$_3$, 400 MHz): δ 7.56 (d, J=6.0, 2H), 6.64 (brs, 1H), 6.40 (brs, 1H), 6.03-5.73 (m, 1H), 4.15 (d, J=5.2, 2H), 4.01 (d, J=17.2, 1H), 3.74-3.65 (m, 1H), 3.62 (d, J=17.2, 1H), 2.97 (t, J=7.6, 2H), 2.89 (t, J=7.6, 2H), 2.56 (m, 2H).

SFC conditions are as follows:
Instrument: Thar 350
Column: AD 250 mm*50 mm, 10 um
Mobile phase: A: Supercritical CO2, B: EtOH, A:B=60:40 at 240 ml/min
Column Temp: 38° C.
Nozzle Pressure: 100 Bar
Nozzle Temp: 60° C.
Evaporator Temp: 20° C.
Trimmer Temp: 25° C.
Wavelength: 220 nm

Scheme I

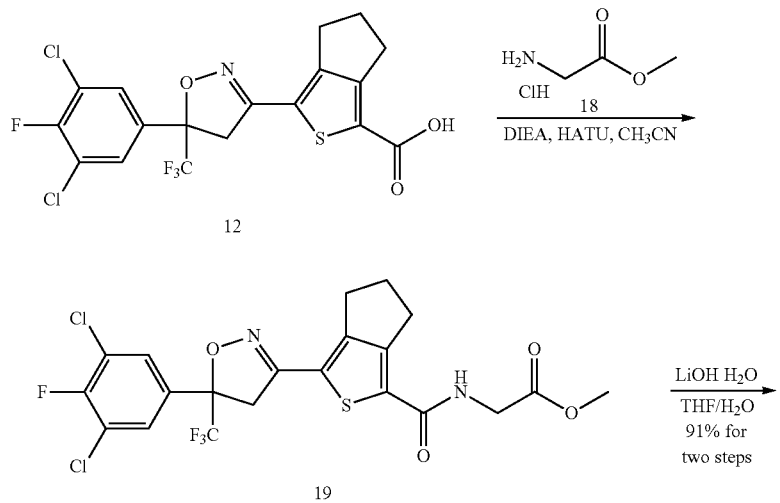

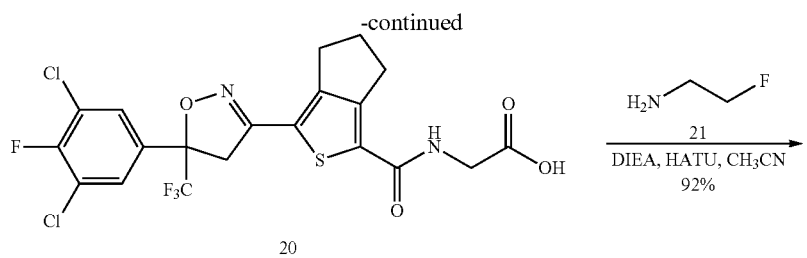

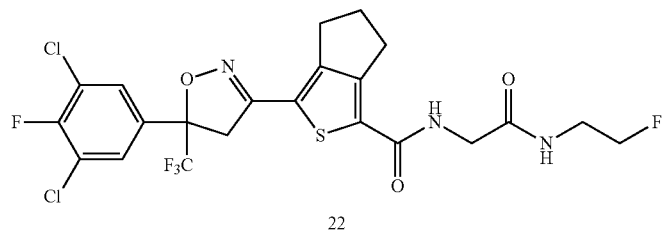

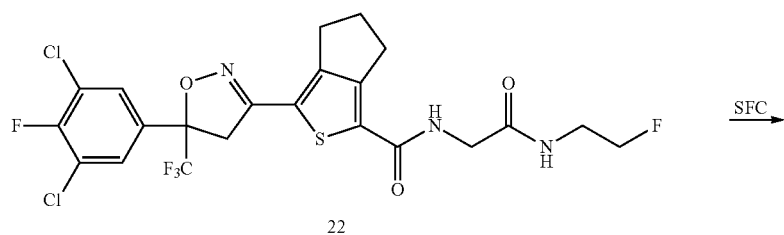

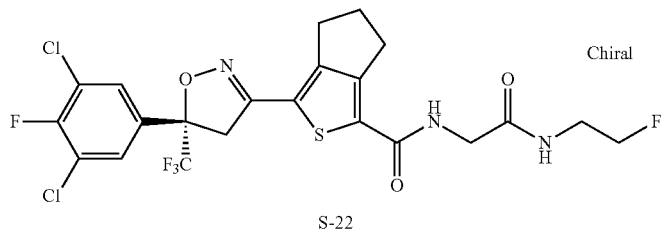

Example 246

3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoroethylcarbamoyl)-methyl]-amide

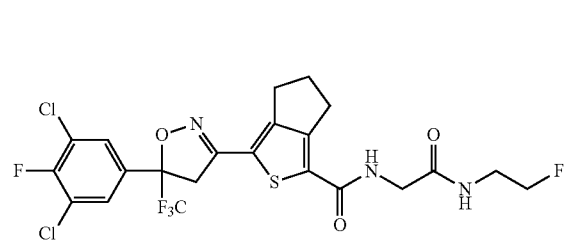 [SMILES: O=C(CNC(=O)c1sc(C2=NOC(c3cc(Cl)c(F)c(Cl)c3)(C(F)(F)F)C2)c2c1CCC2)NCCF]

A) Synthesis of ({3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carbonyl}-amino)-acetic acid methyl ester

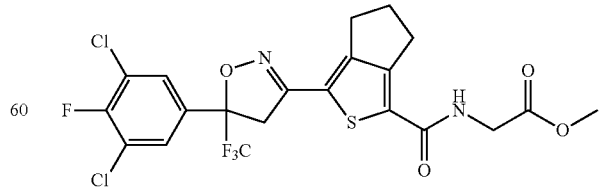

To a solution of compound 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid (10.0 g, 21.4 mmol) in dichloromethane (100 mL) is added triethylamine (6.49 g, 64.2 mmol), glycine methyl ester hydrochloride (3.2 g, 25.7 mmol) and HATU (12.2 g, 32.1 mmol), after the addition the mixture is stirred at room temperature for 1 hour. After being detected by TLC and LCMS, the reaction mixture is diluted with dichloromethane, then the solution is washed with water and brine, dried over anhydrous $Na_2SO_4$, filtered, concentrated and the residue is dried in vacuum to give 11 g crude product, which is used directly in next step.

B) Synthesis of ({3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carbonyl}-amino)-acetic acid

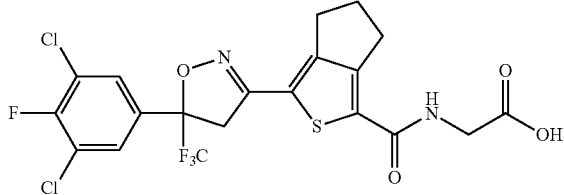 [SMILES: O=C(O)CNC(=O)c1sc(C2=NOC(c3cc(Cl)c(F)c(Cl)c3)(C(F)(F)F)C2)c2c1CCC2]

Stir a mixture of ({3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carbonyl}-amino)-acetic acid methyl ester (11 g, 18.6 mmol) and LiOH—$H_2O$ (1.56 g, 37.2 mmol) in THF (100 mL) and water (50 mL) at room temperature for overnight. After being checked with TLC, the solvent is removed under vacuum, dilute the residue with water (50 mL). Acidify the aqueous mixture with 2M HCl to pH=3, and extract the resultant mixture with EtOAc (100 mL×3), the combined organic layer is washed with brine, dried over anhydrous $Na_2SO_4$ and concentrated under vacuum, the residue is purified by silica gel chromatograph (PE:EtOAc 1:1) to afford ({3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carbonyl}-amino)-acetic acid as a white solid (10.2 g, 90.7% for two steps). MS (m/z): 525 (M+1).

C) Synthesis of 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide

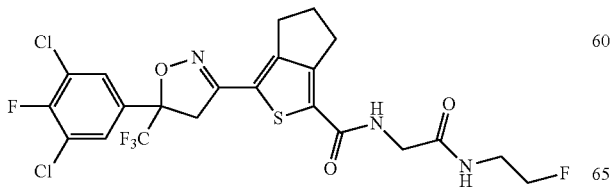

To a solution of compound ({3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carbonyl}-amino)-acetic acid (100 mg, 0.19 mmol) in acetonitrile (5 mL) is added N,N-diisopropylethylamine (49.3 mg, 0.38 mmol), 2-fluoro-ethylamine (14.4 mg, 0.23 mmol) and HATU (108.8 mg, 0.29 mmol), after finished the mixture is stirred at room temperature for 1 hour. After being detected by TLC and LCMS, the reaction mixture is concentrated and the residue is purified by column chromatography to afford desired product (100 mg, 92%). MS (m/z): 570.1 (M+1).

Example 247

(S)-3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide

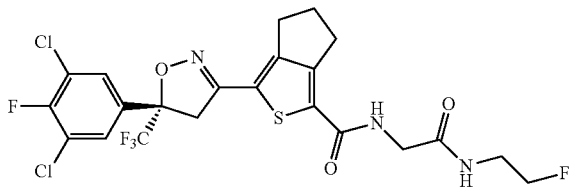 [SMILES: O=C(CNC(=O)c1sc(C2=NO[C@@](c3cc(Cl)c(F)c(Cl)c3)(C(F)(F)F)C2)c2c1CCC2)NCCF]

100 mg of 3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide is separated by SFC separation to give desired product (40 mg, 80%).

$^1$H NMR (CDCl$_3$, 400 MHz): δ 7.49 (d, J=6.0, 2H), 6.64 (brs, 1H), 6.34 (brs, 1H), 4.52 (t, J=4.8, 1H), 4.40 (t, J=4.8, 1H), 4.06 (d, J=4.4, 2H), 3.94 (d, J=17.2, 1 H), 3.63-3.52 (m, 3H), 2.90 (t, J=7.6, 2H), 2.81 (t, J=7.6, 2H), 2.47 (m, 2H).

SFC conditions are as follows:
Instrument: Thar SFC 80
Column: AD 250 mm*20 mm, 20 um
Mobile phase: A: Supercritical CO2, B: EtOH (0.05% DEA), A:B=45:55 at 80 ml/min
Column Temp: 38° C.
Nozzle Pressure: 100 Bar
Nozzle Temp: 60° C.
Evaporator Temp: 20° C.
Trimmer Temp: 25° C.
Wavelength: 220 nm Scheme J

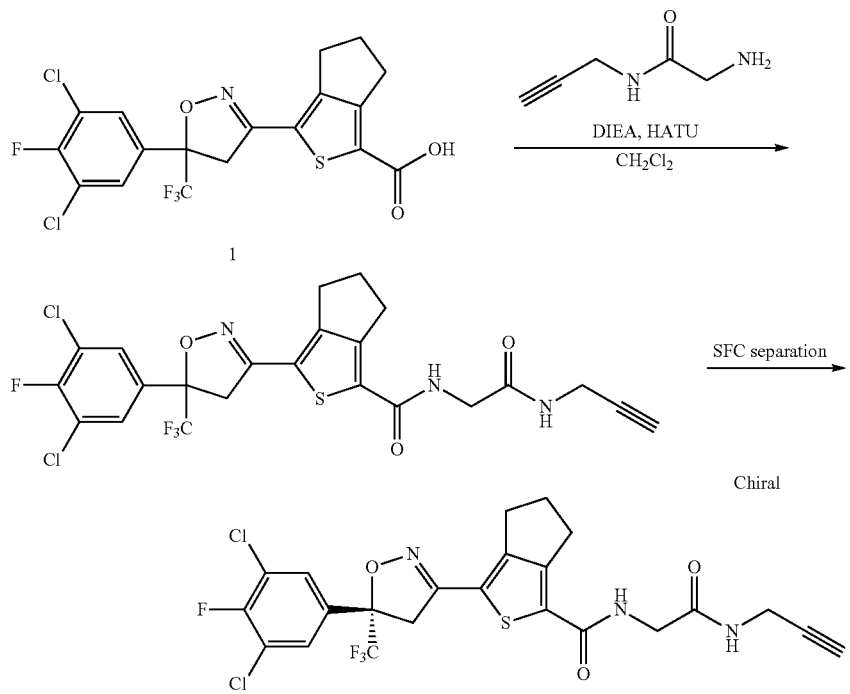

Example 248

3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide Example 249

(S)-3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide

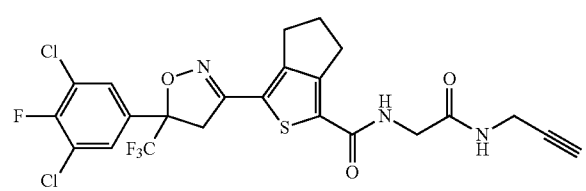 [SMILES: C#CCNC(=O)CNC(=O)c1sc(C2=NOC(c3cc(Cl)c(F)c(Cl)c3)(C(F)(F)F)C2)c2c1CCC2]

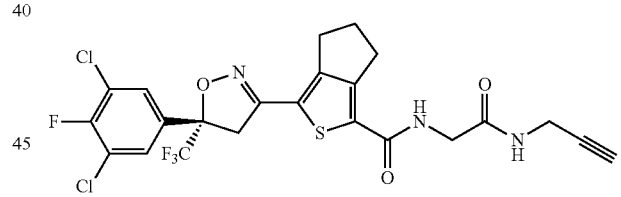

Stir a mixture of 3-(5-(3,5-dichloro-4-fluorophenyl)-5-(trifluoromethyl)-4,5-dihydroisoxazol-3-yl)-5,6-dihydro-4H-cyclopenta[c]thiophene-1-carboxylic acid (0.8 g, 1.7 mmol), N,N-diisopropylethylamine (663 mg, 5.1 mmol), 2-amino-N-(prop-2-yn-1-yl) acetamide hydrochloride (305 mg, 2.0 mmol) and HATU (974 g, 2.6 mmol) in CH$_2$Cl$_2$ (10 mL) at room temperature for 2 hours. The reaction mixture is diluted with CH$_2$Cl$_2$ (40 mL) and is washed with water (10 mL×3) and brine. Then the organic layer is dried over anhydrous Na$_2$SO$_4$ and concentrated under vacuum. Purify the residue by preparative HPLC to afford 3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide as a white solid (850 mg, 88.4%). MS (m/z): 584.1 (M+Na).

850 mg of 3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide is separated by SFC to give (S)-3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide (400 mg, 94% yield, 99.7% ee).

$^1$H NMR (400 MHz, CDCl$_3$) δ 7.58 (d, J=6.0, 2H), 6.76 (t, J=4.8, 1H), 6.46 (t, J=4.8, 1H), 4.14 (m, 4H), 4.03 (d, J=17.2, 1H), 3.64 (d, J=17.2, 1H), 2.99 (t, J=7.6, 2 H), 2.90 (t, J=7.6, 2H), 2.56 (m, 2H), 2.29 (t, J=2.8, 1H). MS (m/z): 584.1 (M+Na).

SFC analysis condition: Column: Chiralcel AS-H 150×4.6 mm I.D., 5 um. Mobile phase: EtOH in CO$_2$ from 5% to 40% over 8 minutes. Flow rate: 3 mL/min. Wavelength: 220 nm. The S-isomer elutes at 4.00 minutes.

Instrument: Thar SFC 200; Column: AS 250 mm*50 mm, 10 um; Mobile phase: A: Supercritical CO$_2$, B: EtOH, A:B=45:55 at 200 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

In Vitro Helminth Assay

Compounds may be evaluated against one or more life stages of helminth to measure anthelmintic activity. Compounds may be evaluated at a single concentration followed by serial dilution in order to determine minimal effective concentration. Typically, worms are exposed to compounds in a liquid solution for a predetermined period of time. Activity is measured through one or more variables, which may include an effect on worm motility (e.g., moving versus non-moving) or viability (e.g., live versus dead).

In Vivo Activity Against Nematodes

Compounds may be evaluated against one or more life stages of helminth infestation in an animal to measure in vivo anthelmintic activity. Compounds may be evaluated a single dose, administered on a milligram per kilogram body weight basis, followed by dose titration in order to determine minimal effective point dose. In a rodent anthelmintic model, for example, adult Mongolian gerbils (*Meriones unguiculates*) infected with one or more species of Strongylid nematode (e.g., *Haemonchus contortus* and/or *Trichostrongylus colubriformis*) are dosed with compounds, administered via oral gavage. Gerbils are necropsied and gastrointestinal tract worm burden is measured and compared to untreated, infected control gerbils to determine the degree of anthelmintic activity. Similar testing may be conducted in higher species (e.g., dogs, cats, sheep, cattle) whereby nematode burden in treated animals is compared to burden in untreated, infected animals to measure the potency and duration of anthelmintic activity.

In Vitro Larval Immersion Microassay (LIM)

The larval immersion microassay may be conducted as described in White, et al., J. Med. Entomol. 41: 1034-1042 (2004). Briefly, experimental test articles are formulated in dimethylsulfoxide (DMSO) to prepare a stock solution at a concentration of 10 mM. Using 96-well microtiter plates, an aliquot of the 10 mM sample is subsequently diluted in a water-based solution containing 1% ethanol and 0.2% Triton X-100, to obtain the desired concentration (typically 0.3 mM or lower) of experimental test article in a volume of 0.1 ml (minimum n=3 replicates per compound or concentration). Approximately 30-50 Lone star tick larvae (*Amblyomma americanum*) are submerged into each well containing experimental test articles. After a 30 minute immersion period, larvae are removed with a wide-bore pipette tip in 0.05 ml of fluid, dispensed into a commercial paper tissue biopsy bag which is sealed at the top with a plastic dialysis clip, inverted and allowed to air dry for 60 minutes. Bags containing larvae are then incubated at approximately 27 degrees Celsius and >90% relative humidity. After 24 hours, bags are opened, live and dead larvae are counted and percent larval mortality is calculated as follows: % Efficacy=(# dead larvae)/(# total larvae)×100.

The following of the Examples exhibited efficacy, and at the level of ≥80% efficacy when tested in this assay at 300 micromolar: 32, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 74, 75, 76, 77, 78, 79, 80, 81, 82, 83, 84, 85, 86, 87b, 94, 95, 96, 230, 231, 232, 233, 236, 237, 240, 241, 243, 244, 245, 246, 247, and 249.

In Vivo Rodent Acaricide Test (RAT)

Evaluation of experimental test articles may conducted using a modified version of the assay as described in Gutierrez et al., J. Med. Entomol. 43(3): 526-532 (2006). The assay may be modified by using a different tick species (the reference describes *Amblyomma americanum* ticks) such as *Dermacentor variabilis* ticks. Further, the reference describes using topical administration, but oral administration may be used. Briefly, experimental test articles are formulated in a solution of polyethylene glycol-300, propylene glycol and water to the desired concentration, typically 1-25 mg/ml, depending on solubility and desired point dose. Tick containment units (comprised of a baby nipple, ventilated screw cap top and reinforcing rubber washer) are attached to the dorsum of adult Sprague-Dawley rats. After attachment of containment units, approximately 10 unfed nymphal stage American dog ticks (*Dermacentor variabilis*) are placed inside of each containment unit. Approximately 24 hours after infestation, test article formulations are administered to rats via oral gavage. Negative control rats receive polyethylene glycol-300, propylene glycol and water alone. Depending on compound availability, a minimum of three (3) and a maximum of five (5) rats are utilized per treatment group. Forty-eight (48) hours post-treatment, containment units are removed and live and dead ticks were counted. Live tick counts are transformed using the natural logarithm transformation plus one (Ln count+1); addition of one to each count serve to adjust for counts that were zero. Geometric mean (GM) group tick counts are obtained via back-transformation of group mean transformed counts and subtracting one. The non-treated control group is used for comparison to the groups receiving experimental test articles for the calculation of percent efficacy (% reduction in live tick counts). The efficacy of treatments is calculated by comparing the geometric mean (GM) number of live ticks observed on treated rats with the GM number of live ticks counted on the negative control rats, using the following formula:

$$\% \text{ Efficacy} = \frac{(GM \text{ \# live ticks control} - GM \text{ \# live ticks treated})}{GM \text{ \# live ticks control}} \times 100$$

The following Examples exhibited ≥50% efficacy when tested in this assay at a dose of not more than 25 mpk: 32, 36, 38, 39, 41, 42, 43, 45, 46, 47, 49, 50, 51, 52, 53, 54, 55, 56, 57, 58, 59, 61, 87b, 95, 96, 234, 235, 240, 241, 243, 244, 245, 246, 247, and 249.

Activity in the above assays demonstrates the compounds of the invention are useful for controlling ecto- or endoparasite infestations.

The following are embodiments of the invention and are non-limiting.

1. A compound, or a salt thereof, of formula I

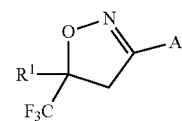

wherein A is

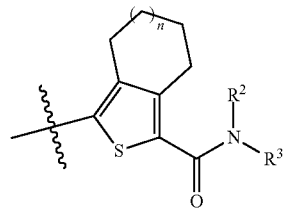

or

-continued

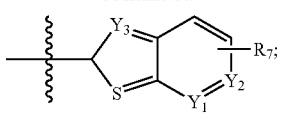

n is 0 or 1;

$R^1$ is thienyl or phenyl, said thienyl or phenyl substituted with 2 or 3 of the same or different halo atoms;

$R^2$ is at each occurrence independently hydrogen, $C_1$-$C_5$ alkyl, $C_3$-$C_6$ cycloalkyl, or $C_1$-$C_5$ haloalkyl;

$R^3$ is

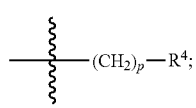

p is at each occurrence independently 0 or 1;

$R^4$ is $C_1$-$C_5$ alkyl, $C_1$-$C_5$ haloalkyl, $C_1$-$C_5$ cyanoalkyl, $C_1$-$C_5$ alkylthio, $C_3$-$C_6$ cycloalkyl optionally substituted with hydroxy, halo, or $C_1$-$C_5$ alkyl: $C_3$-$C_5$ cycloheteroalkyl optionally substituted with $C_1$-$C_5$ alkyl, $C_3$-$C_6$ cycloalkyl, or $C_1$-$C_5$ haloalkyl: phenyl, thienyl, pyridinyl, or

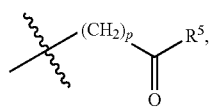

wherein one of the carbons in said cycloalkyls, independently, or cycloheteroalkyl may form a carbonyl group, and wherein said phenyl, thienyl, or pyridinyl is optionally substituted with halo or a carbamoyl group;

$R^5$ is hydroxy, —O—($C_1$-$C_5$ alkyl), or

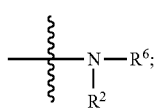

$R^6$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl;

or $R^2$ and $R^3$ combine to form, with the nitrogen to which they are attached,

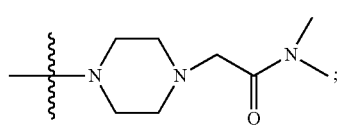 [SMILES: *N1CCN(CC(=O)N(C)C)CC1 ; ";"]

$Y_1$, $Y_2$, and $Y_3$ are carbon or nitrogen with at most only one of $Y_1$, $Y_2$, and $Y_3$ being nitrogen, and when $Y_1$, $Y_2$, or $Y_3$ is a carbon, each may be substituted by $C_1$-$C_5$ alkyl;

$R^7$ is hydrogen, halo, $C_1$-$C_5$ alkyl, or

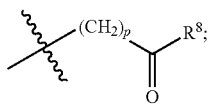

$R^8$ is hydroxy, —O—($C_1$-$C_5$ alkyl), or

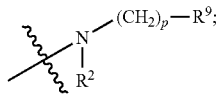

$R^9$ is $C_1$-$C_5$ alkyl,

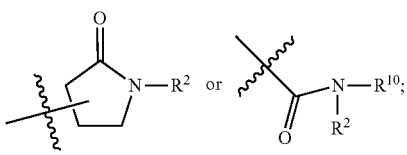

and $R^{10}$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl.

2. A compound of clause 1 wherein A is

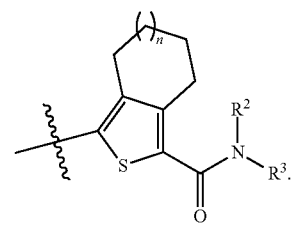

3. A compound according to any of clauses 1-2 wherein $R^2$ is hydrogen and n is 1.

4. A compound of according to any of clauses 1-3 wherein $R^3$ is

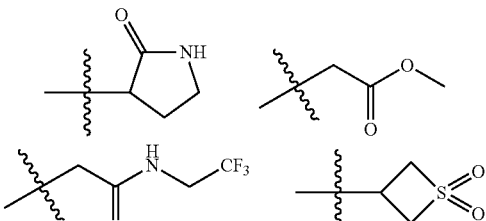

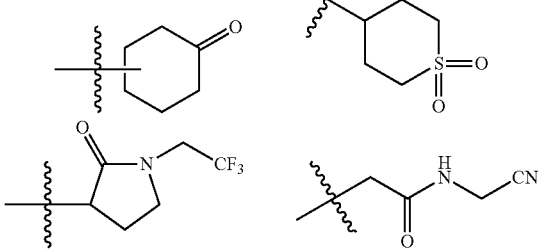

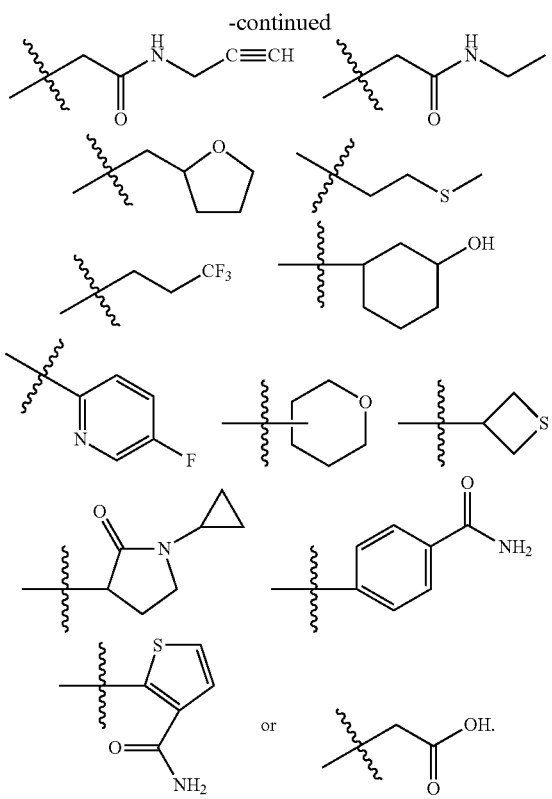

5. A compound according to any of clauses 1 to 4, or salt thereof, being
3-(5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;
N,N-Dimethyl-2-(4-{3-[5-(3,4,5-trichloro-thiophen-2-yl)-5-trifluoromethyl-4,5-dihydro-isoxazol-3-yl]-4,5,6,7-tetrahydro-benzo[c]thiophene-1-carbonyl}-piperazin-1-yl)-acetamide;
({3-[5-(3,5-Dichloro-phenyl)-5-trifluoromethyl-4,5-dihydro-isoxazol-3-yl]-4,5,6,7-tetrahydro-benzo[c]thiophene-1-carbonyl}-amino)-acetic acid methyl ester;
({3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl}-amino)-acetic acid methyl ester;
3-(5-(3,5-dichlorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide;
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid (1,1-dioxo-thietan-3-yl)-amide;
3-(5-(3,5-dichlorophenyl)-5-(trifluoromethyl)-4,5-dihydroisoxazol-3-yl)-N-(3-oxocyclohexyl)-4,5,6,7-tetrahydrobenzo[c]thiophene-1-carboxamide;
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-1λ6-thiopyran-4-yl)-amide;
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid [2-oxo-1-(2,2,2-trifluoro-ethyl)-pyrrolidin-3-yl]-amide;
3-(5-(3,5-dichlorophenyl)-5-(trifluoromethyl)-4,5-dihydroisoxazol-3-yl)-N—((R)-2-oxopyrrolidin-3-yl)-5,6-dihydro-4H-cyclopenta[c]thiophene-1-carboxamide;
N-(2-(cyanomethylamino)-2-oxoethyl)-3-(5-(3,5-dichlorophenyl)-5-(trifluoromethyl)-4,5-dihydroisoxazol-3-yl)-5,6-dihydro-4H-cyclopenta[c]thiophene-1-carboxamide;
3-(5-(3,5-dichlorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide;
N-(2-oxo-2-(2,2,2-trifluoroethylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;
N—((R)-2-oxopyrrolidin-3-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;
N-(2-(cyanomethylamino)-2-oxoethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;
N-(2-oxo-2-(prop-2-ynylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;
3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-4,5,6,7-tetrahydrobenzo[c]thiophene-1-carboxamide;
3-(5-(3,5-dichloro-4-fluorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;
N-(2-(cyanomethylamino)-2-oxoethyl)-3-(5-(3,5-dichloro-4-fluorophenyl)-5-(trifluoromethyl)-4,5-dihydroisoxazol-3-yl)-4,5,6,7-tetrahydrobenzo[c]thiophene-1-carboxamide;
3-(5-(3,5-dichloro-4-fluorophenyl)-5-(trifluoromethyl)-4,5-dihydroisoxazol-3-yl)-N-(2-oxo-2-(prop-2-ynylamino)ethyl)-4,5,6,7-tetrahydrobenzo[c]thiophene-1-carb oxamide;
N-(2-oxo-2-(2,2,2-trifluoroethylamino)ethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;
N—((R)-2-oxopyrrolidin-3-yl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;
N-(2-(cyanomethylamino)-2-oxoethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;
N-(2-oxo-2-(prop-2-ynylamino)ethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;
N-(2-oxo-1-(2,2,2-trifluoroethyl)pyrrolidin-3-yl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;
3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide;
3-(5-(3,5-dichloro-4-fluorophenyl)-5-(trifluoromethyl)-4,5-dihydroisoxazol-3-yl)-N—((R)-2-oxopyrrolidin-3-yl)-5,6-dihydro-4H-cyclopenta[c]thiophene-1-carboxamide;
N-(2-(cyanomethylamino)-2-oxoethyl)-3-(5-(3,5-dichloro-4-fluorophenyl)-5-(trifluoromethyl)-4,5-dihydroisoxazol-3-yl)-5,6-dihydro-4H-cyclopenta[c]thiophene-1-carboxamide;
3-(5-(3,5-dichloro-4-fluorophenyl)-5-(trifluoromethyl)-4,5-dihydroisoxazol-3-yl)-N-(2-oxo-1-(2,2,2-trifluoroethyl)pyrrolidin-3-yl)-5,6-dihydro-4H-cyclopenta[c]thiophene-1-carboxamide;

3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide;

3-(5-(3,5-dichlorophenyl)-5-(trifluoromethyl)-4,5-dihydroisoxazol-3-yl)-N-(2-oxo-2-(2,2,2-trifluoroethylamino)ethyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(2-(ethylamino)-2-oxoethyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-((tetrahydrofuran-2-yl)methyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(2-(methylthio)ethyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(3,3,3-trifluoropropyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(3-hydroxycyclohexyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(5-fluoropyridin-2-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(tetrahydro-2H-pyran-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(thietan-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(tetrahydro-2H-pyran-4-yl)-4,5,6,7-tetrahydrobenzo[c]thiophene-1-carboxamide;

N-(1-cyclopropyl-2-oxopyrrolidin-3-yl)-3-(5-(3,5-dichlorophenyl)-5-(trifluoromethyl)-4,5-dihydroisoxazol-3-yl)-4,5,6,7-tetrahydrobenzo[c]thiophene-1-carboxamide;

N-(2-oxo-2-(prop-2-ynylamino)ethyl)-3-(5-(3,4,5-trichlorothiophen-2-yl)-5-(trifluoromethyl)-4,5-dihydroisoxazol-3-yl)-4,5,6,7-tetrahydrobenzo[c]thiophene-1-carboxamide;

3-[5-(3,4,5-Trichloro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-thiopyran-4-yl)-amide;

N-(2-oxo-1-(2,2,2-trifluoroethyl)pyrrolidin-3-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N-(tetrahydro-2H-pyran-4-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N-(1-cyclopropyl-2-oxopyrrolidin-3-yl)-3-(5-(3,4,5-trichlorophenyl)-5-(tri fluoromethyl)-4,5-dihydroisoxazol-3-yl)-4,5,6,7-tetrahydrobenzo[c]thiophene-1-carboxamide;

3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid (1,1-dioxo-thietan-3-yl)-amide;

3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-thiopyran-4-yl)-amide;

3-(5-(3,5-dichloro-4-fluorophenyl)-5-(trifluoromethyl)-4,5-dihydroisoxazol-3-yl)-N-(4-oxocyclohexyl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N-(2-oxo-1-(2,2,2-trifluoroethyl)pyrrolidin-3-yl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N-(tetrahydro-2H-pyran-4-yl)-4,5,6,7-tetrahydrobenzo[c]thiophene-1-carboxamide;

N-(1-cyclopropyl-2-oxopyrrolidin-3-yl)-3-(5-(3,5-dichloro-4-fluorophenyl)-5-(trifluoromethyl)-4,5-dihydroisoxazol-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(4-oxocyclohexyl)-5,6-dihydro-4H-cyclopenta[c]thiophene-1-carboxamide;

3-(5-(3,5-dichlorophenyl)-5-(trifluoromethyl)-4,5-dihydroisoxazol-3-yl)-N-(2-oxo-1-(2,2,2-trifluoroethyl)pyrrolidin-3-yl)-5,6-dihydro-4H-cyclopenta[c]thiophene-1-carboxamide;

3-((R)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;

3-((S)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;

N-(4-carbamoylphenyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide;

3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid (3-carbamoyl-thiophen-2-yl)-amide;

2-(3-(5-(3,5-dichlorophenyl)-5-(trifluoromethyl)-4,5-dihydroisoxazol-3-yl)-4,5,6,7-tetrahydrobenzo[c]thiophene-1-carboxamido)acetic acid;

({3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl}-amino)-acetic acid;

N-(2-(cyanomethylamino)-2-oxoethyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(2-oxo-2-(prop-2-ynylamino)ethyl)-4,5,6,7-tetrahydrobenzo[c]thiophene-1-carboxamide; or N-(2-(cyanomethylamino)-2-oxoethyl)-3-(5-(3,4,5-trichlorothiophen-2-yl)-5-(trifluoromethyl)-4,5-dihydroisoxazol-3-yl)-4,5,6,7-tetrahydrobenzo[c]thiophene-1-carboxamide.

6. A compound of clause 1 wherein A is

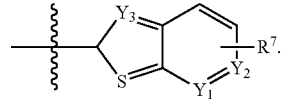

7. A compound of clause 1 or 6 wherein $Y_1$ is nitrogen.

8. A compound according to any of clauses 1, 6, or 7, wherein $R^7$ is

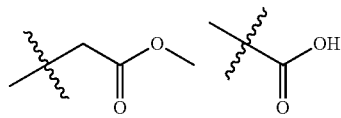

-continued

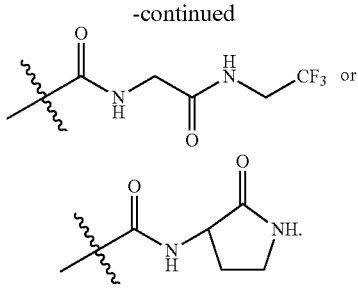

9. A compound according to any of clauses 6-8, or salt thereof, being
3-(4-chlorobenzo[b]thiophen-2-yl)-5-(3,5-dichlorophenyl)-5-(trifluoromethyl)-4,5-dihydroisoxazole;
2-[5-(3,5-Dichloro-phenyl)-5-trifluoromethyl-4,5-dihydro-isoxazol-3-yl]-thieno[2,3-c]pyridine;
5-Bromo-2-[5-(3,5-dichloro-phenyl)-5-trifluoromethyl-4,5-dihydro-isoxazol-3-yl]-thieno[2,3-b]pyridine;
2-[5-(3,5-Dichloro-phenyl)-5-trifluoromethyl-4,5-dihydro-isoxazol-3-yl]-thieno[2,3-b]pyridine;
3-(benzo[b]thiophen-2-yl)-5-(3,5-dichlorophenyl)-5-(trifluoromethyl)-4,5-dihydroisoxazole;
3-(benzo[d]thiazol-2-yl)-5-(3,5-dichlorophenyl)-5-(trifluoromethyl)-4,5-dihydroisoxazole;
5-(3,5-dichlorophenyl)-3-(3-methylbenzo[b]thiophen-2-yl)-5-(trifluoromethyl)-4,5-dihydroisoxazole;
5-(3,5-dichlorophenyl)-3-(5-methylbenzo[b]thiophen-2-yl)-5-(trifluoromethyl)-4,5-dihydroisoxazole;
3-(5-chlorobenzo[b]thiophen-2-yl)-5-(3,5-dichlorophenyl)-5-(trifluoromethyl)-4,5-dihydroisoxazole;
methyl 2-(5-(3,5-dichlorophenyl)-5-(trifluoromethyl)-4,5-dihydroisoxazol-3-yl)thieno[2,3-b]pyri dine-5-carboxylate;
2-[5-(3,5-Dichloro-phenyl)-5-trifluoromethyl-4,5-dihydro-isoxazol-3-yl]-thieno[2,3-b]pyridine-5-carboxylic acid;
2-(5-(3,5-dichlorophenyl)-5-(trifluoromethyl)-4,5-dihydroisoxazol-3-yl)-N-(2-oxo-2-(2,2,2-trifluoroethylamino)ethyl)thieno[2,3-b]pyridine-5-carboxamide; or
2-(5-(3,5-dichlorophenyl)-5-(trifluoromethyl)-4,5-dihydroisoxazol-3-yl)-N—((R)-2-oxopyrrolidin-3-yl)thieno[2,3-b]pyridine-5-carboxamide.

10. A compound, or salt thereof, being
(S)-3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide;
3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide;
(S)-3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amid);
3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide;
(S)-3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide;
3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide; or
(S)-3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide.

11. A formulation comprising a compound or salt of any of clauses 1-10 and one or more acceptable carriers.

12. The formulation of clause 11 wherein it further comprises at least one additional active ingredient.

13. The formulation of clause 11 or clause 12 wherein it is a human pharmaceutical formulation.

14. The formulation of clause 11 or clause 12 wherein it is a veterinary pharmaceutical formulation.

15. A method of controlling a parasite infestation in or on an animal in need thereof comprising administering an effective amount of a compound or salt of any of clauses 1-10 to said animal.

16. The method of clause 15 wherein at least one other active ingredient is administered to said animal.

17. The method of clause 15 or clause 16 wherein said animal is a human.

18. The method of clause 15 or clause 16 wherein said animal is a companion animal.

19. The method of clause 17 or clause 18 wherein said companion animal is a dog or cat.

20. The method according to any of clauses 15-19 wherein said parasite is a tick.

21. The method of clause 15 wherein said animal is a livestock animal.

22. A method for preventing or treating diseases transmitted through parasites comprising administering an effective amount of a compound of any of clauses 1-10 to an animal in need thereof.

23. The method of clause 22 wherein at least one other active ingredient is administered to said animal.

24. The method of clause 22 or clause 23 wherein said animal is a human.

25. The method of clause 22 wherein said animal is a companion animal.

26. The method of clause 25 wherein said companion animal is a dog or cat.

27. The method according to any of clauses 22-26 wherein said parasite is a tick.

28. The method of clause 22 or clause 23 wherein said animal is a livestock animal.

29. A method for controlling parasites, characterized in that a compound of any of clauses 1-10 is allowed to act on the pests or their habitat, or both.

30. The method of clause 29 wherein the compound is placed on a plant or an animal.

31. Use of compounds or salts thereof of any of clauses 1-10 for controlling parasites.

32. A compound or salt according to any of clauses 1-10 for use in therapy.

33. A compound or salt according to any of clauses 1-10 for use in controlling an ectoparasite infestation.

34. A compound, or salt thereof, of Formula II

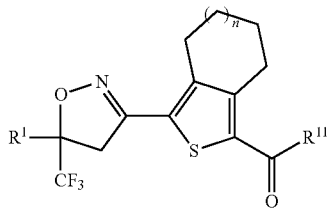

wherein n is 0 or 1;
$R^1$ is thienyl or phenyl, said thienyl or phenyl substituted with 2 or 3 of the same or different halo atoms; and
$R^{11}$ is hydroxy, —O—($C_1$-$C_4$ alkyl), or a halo atom.

35. The compound of 34 wherein $R^1$ is phenyl substituted with 2 or 3 of the same or different halo atoms.

36. The compound according to clauses 34 or 35 wherein $R^{11}$ is hydroxy.

37. The compound according to any of clauses 34-36 wherein it is
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid methyl ester;
3-[5-(3,5-Dichloro-phenyl)-5-trifluoromethyl-4,5-dihydro-isoxazol-3-yl]-5,6-dihydro-4H-cyclopenta[c]thiophene-1-carboxylic acid methyl ester;
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid methyl ester
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid methyl ester;
3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid methyl ester;
3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid methyl ester;
3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid methyl ester;
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid;
3-[5-(3,5-Dichloro-phenyl)-5-trifluoromethyl-4,5-dihydro-isoxazol-3-yl]-5,6-dihydro-4H-cyclopenta[c]thiophene-1-carboxylic acid;
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid;
3-[5-(3,4,5-Trichloro-phenyl)-5-trifluoromethyl-4,5-dihydro-isoxazol-3-yl]-4,5,6,7-tetrahydro-benzo[c]thiophene-1-carboxylic acid;
3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid;
3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid;
3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid;
3-(5-(3,5-dichlorophenyl)-5-(trifluoromethyl)-4,5-dihydroisoxazol-3-yl)-4,5,6,7-tetrahydrobenzo[c]thiophene-1-carbonyl chloride; or
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl chloride.

38. A compound according to clause 34 wherein it is 3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid.

39. A compound according to clause 34 wherein it is 3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid.

40. A compound according to clause 34 wherein it is 3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid.

41. A compound according to clause 34 wherein it is 3-[5-(3,4,5-Trichloro-phenyl)-5-trifluoromethyl-4,5-dihydro-isoxazol-3-yl]-4,5,6,7-tetrahydro-benzo[c]thiophene-1-carboxylic acid.

42. A process for preparing a compound according to clauses 1-5 or 10, comprising synthetically modifying a compound according to any of clauses 34-41.

43. The process of clause 42 wherein a compound according to any of clauses 34-41 is reacted with a compound of the formula

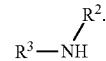

We claim:
1. A compound, or a salt thereof, of formula I

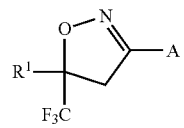

wherein A is

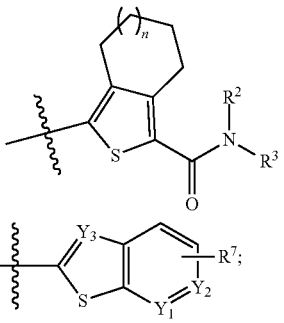

n is 0 or 1;
$R^1$ is thienyl or phenyl, said thienyl or phenyl substituted with 2 or 3 of the same or different halo atoms;
$R^2$ is at each occurrence independently hydrogen, $C_1$-$C_5$ alkyl, $C_3$-$C_6$ cycloalkyl, or $C_1$-$C_5$ haloalkyl;

$R^3$ is

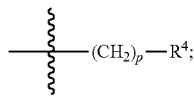

p is at each occurrence independently 0 or 1;

$R^4$ is $C_1$-$C_5$ alkyl, $C_1$-$C_5$ haloalkyl, $C_1$-$C_5$ cyanoalkyl, $C_1$-$C_5$ alkylthio, $C_3$-$C_6$ cycloalkyl optionally substituted with hydroxy, halo, or $C_1$-$C_5$ alkyl: $C_3$-$C_5$ cycloheteroalkyl optionally substituted with $C_1$-$C_5$ alkyl, $C_3$-$C_6$ cycloalkyl, or $C_1$-$C_5$ haloalkyl: phenyl, thienyl, pyridinyl, or

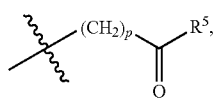

wherein one of the carbons in said cycloalkyls, independently, or cycloheteroalkyl may form a carbonyl group, and wherein said phenyl, thienyl, or pyridinyl is optionally substituted with halo or a carbamoyl group;

$R^5$ is hydroxy, —O—($C_1$-$C_5$ alkyl), or

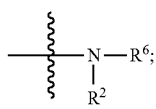

$R^6$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl;

or $R^2$ and $R^3$ combine to form, with the nitrogen to which they are attached,

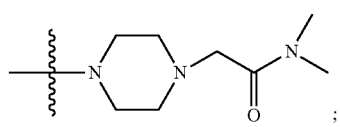 [SMILES: *N1CCN(CC(=O)N(C)C)CC1 ; ";"]

$Y_1, Y_2,$ and $Y_3$ are carbon or nitrogen with at most only one of $Y_1, Y_2,$ and $Y_3$ being nitrogen, and when $Y_1, Y_2,$ or $Y_3$ is a carbon, each may be substituted by $C_1$-$C_5$ alkyl;

$R^7$ is hydrogen, halo, $C_1$-$C_5$ alkyl, or

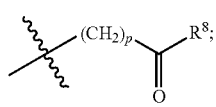

$R^8$ is hydroxy, —O—($C_1$-$C_5$ alkyl), or

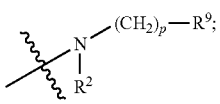

$R^9$ is $C_1$-$C_5$ alkyl,

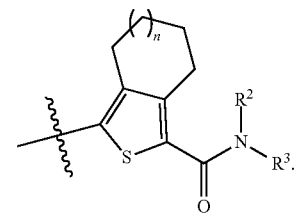

and $R^{10}$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl.

2. The compound of claim 1, or a salt thereof, wherein A is

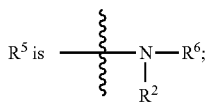

3. The compound of claim 1, or a salt thereof, wherein $R^2$ is hydrogen and n is 1.

4. The compound of claim 2, or a salt thereof, wherein $R^1$ is phenyl substituted 3 times with the same or different of chloro and fluoro; n is 0; $R^2$ is hydrogen, $R^3$ is —$CH_2$—$R^4$; $R^4$ is —C(O)—$R^5$;

$R^5$ is 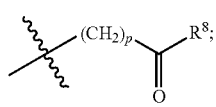

and $R^6$ is $C_1$-$C_5$ haloalkyl.

5. The compound of claim 4, or a salt thereof, wherein $R^1$ is

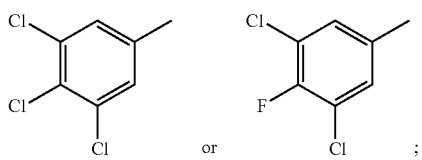

and $R^6$ is difluoroethyl.

6. The compound of claim 1, or a salt thereof, wherein $R^3$ is

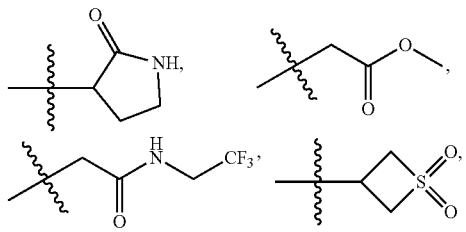

-continued

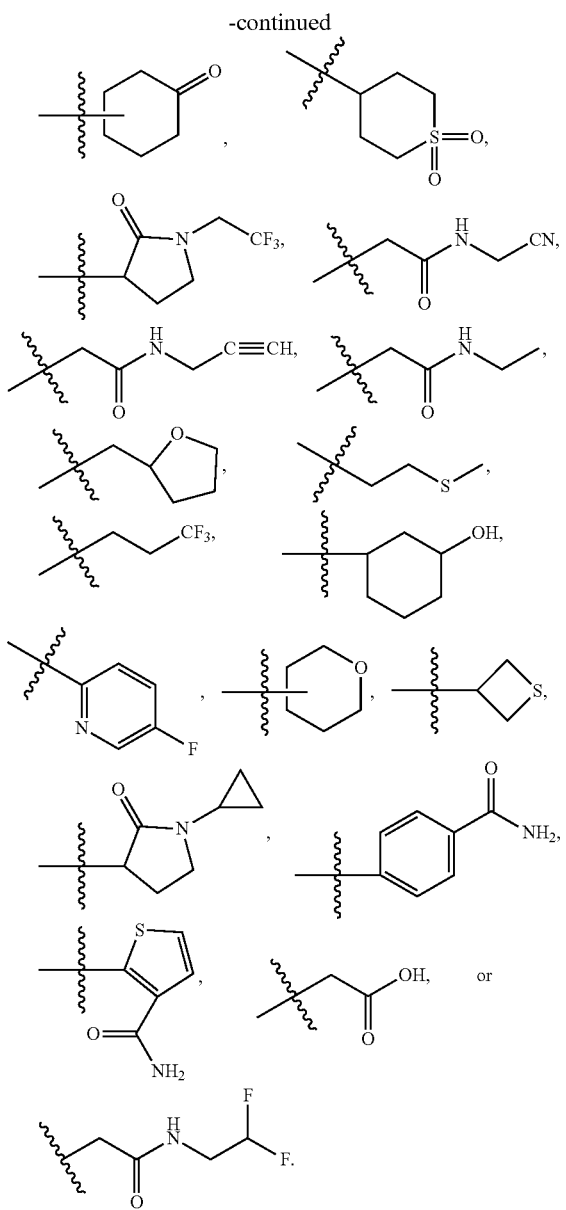

7. The compound of claim 1, or salt thereof, being 3-(5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;

N,N-Dimethyl-2-(4-{3-[5-(3,4,5-trichloro-thiophen-2-yl)-5-trifluoromethyl-4,5-dihydro-isoxazol-3-yl]-4,5,6,7-tetrahydro-benzo[c]thiophene-1-carbonyl}-piperazin-1-yl)-acetamide;

({3-[5-(3,5-Dichloro-phenyl)-5-trifluoromethyl-4,5-dihydro-isoxazol-3-yl]-4,5,6,7-tetrahydro-benzo[c]thiophene-1-carbonyl}-amino)-acetic acid methyl ester;

({3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl}-amino)-acetic acid methyl ester;

3-(5-(3,5-dichlorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide;

3-[5-(3,5-Dichloro-phenyl)-5-trifluoromethyl-4,5-dihydro-isoxazol-3-yl]-4,5,6,7-tetrahydro-benzo[c]thiophene-1-carboxylic acid (1,1-dioxo-thietan-3-yl)-amide;

3-(5-(3,5-dichlorophenyl)-5-(trifluoromethyl)-4,5-dihydroisoxazol-3-yl)-N-(3-oxocyclohexyl)-4,5,6,7-tetrahydrobenzo[c]thiophene-1-carboxamide;

3-[5-(3,5-Dichloro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-1l6-thiopyran-4-yl)-amide;

3-[5-(3,5-Dichloro-phenyl)-5-trifluoromethyl-4,5-dihydro-isoxazol-3-yl]-4,5,6,7-tetrahydro-benzo[c]thiophene-1-carboxylic acid [2-oxo-1-(2,2,2-trifluoro-ethyl)-pyrrolidin-3-yl]-amide;

3-(5-(3,5-dichlorophenyl)-5-(trifluoromethyl)-4,5-dihydroisoxazol-3-yl)-N—((R)-2-oxopyrrolidin-3-yl)-5,6-dihydro-4H-cyclopenta[c]thiophene-1-carboxamide;

N-(2-(cyanomethylamino)-2-oxoethyl)-3-(5-(3,5-dichlorophenyl)-5-(trifluoromethyl)-4,5-dihydroisoxazol-3-yl)-5,6-dihydro-4H-cyclopenta[c]thiophene-1-carboxamide;

3-(5-(3,5-dichlorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide;

N-(2-oxo-2-(2,2,2-trifluoroethylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N—((R)-2-oxopyrrolidin-3-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N-(2-(cyanomethylamino)-2-oxoethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N-(2-oxo-2-(prop-2-ynylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;

N-(2-(cyanomethylamino)-2-oxoethyl)-3-(5-(3,5-dichloro-4-fluorophenyl)-5-(trifluoromethyl)-4,5-dihydroisoxazol-3-yl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N-(2-oxo-2-(prop-2-ynylamino)ethyl)-4,5,6,7-tetrahydrobenzo[c]thiophene-1-carboxamide;

N-(2-oxo-2-(2,2,2-trifluoroethylamino)ethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;

N—((R)-2-oxopyrrolidin-3-yl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;

N-(2-(cyanomethylamino)-2-oxoethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;

N-(2-oxo-2-(prop-2-ynylamino)ethyl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;

N-(2-oxo-1-(2,2,2-trifluoroethyl)pyrrolidin-3-yl)-3-(5-(3,4,5-trichlorophenyl)-5-(trifluoromethyl)-4,5-dihydroisoxazol-3-yl)-5,6-dihydro-4H-cyclopenta[c]thiophene-1-carboxamide;

3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide;

3-(5-(3,5-dichloro-4-fluorophenyl)-5-(trifluoromethyl)-4,5-dihydroisoxazol-3-yl)-N—((R)-2-oxopyrrolidin-3-yl)-5,6-dihydro-4H-cyclopenta[c]thiophene-1-carboxamide;

N-(2-(cyanomethylamino)-2-oxoethyl)-3-(5-(3,5-dichloro-4-fluorophenyl)-5-(trifluoromethyl)-4,5-dihydroisoxazol-3-yl)-5,6-dihydro-4H-cyclopenta[c]thiophene-1-carboxamide;

3-(5-(3,5-dichloro-4-fluorophenyl)-5-(trifluoromethyl)-4,5-dihydroisoxazol-3-yl)-N-(2-oxo-1-(2,2,2-trifluoroethyl)pyrrolidin-3-yl)-5,6-dihydro-4H-cyclopenta[c]thiophene-1-carboxamide;

3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide;

3-(5-(3,5-dichlorophenyl)-5-(trifluoromethyl)-4,5-dihydroisoxazol-3-yl)-N-(2-oxo-2-(2,2,2-trifluoroethylamino)ethyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(2-(ethylamino)-2-oxoethyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-((tetrahydrofuran-2-yl)methyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(2-(methylthio)ethyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(3,3,3-trifluoropropyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(3-hydroxycyclohexyl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(5-fluoropyridin-2-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(tetrahydro-2H-pyran-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(thietan-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(tetrahydro-2H-pyran-4-yl)-4,5,6,7-tetrahydrobenzo[c]thiophene-1-carboxamide;

N-(1-cyclopropyl-2-oxopyrrolidin-3-yl)-3-(5-(3,5-dichlorophenyl)-5-(trifluoromethyl)-4,5-dihydroisoxazol-3-yl)-4,5,6,7-tetrahydrobenzo[c]thiophene-1-carboxamide;

N-(2-oxo-2-(prop-2-ynylamino)ethyl)-3-(5-(3,4,5-trichlorothiophen-2-yl)-5-(trifluoromethyl)-4,5-dihydroisoxazol-3-yl)-4,5,6,7-tetrahydrobenzo[c]thiophene-1-carboxamide;

3-[5-(3,4,5-Trichloro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-thiopyran-4-yl)-amide;

N-(2-oxo-1-(2,2,2-trifluoroethyl)pyrrolidin-3-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N-(tetrahydro-2H-pyran-4-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

N-(1-cyclopropyl-2-oxopyrrolidin-3-yl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide;

3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid (1,1-dioxo-thietan-3-yl)-amide;

3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid (1,1-dioxo-hexahydro-thiopyran-4-yl)-amide;

3-(5-(3,5-dichloro-4-fluorophenyl)-5-(trifluoromethyl)-4,5-dihydroisoxazol-3-yl)-N-(4-oxocyclohexyl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N-(2-oxo-1-(2,2,2-trifluoroethyl)pyrrolidin-3-yl)-4,5,6,7-tetrahydrobenzo[c]thiophene-1-carboxamide;

3-(5-(3,5-dichloro-4-fluorophenyl)-5-(trifluoromethyl)-4,5-dihydroisoxazol-3-yl)-N-(tetrahydro-2H-pyran-4-yl)-4,5,6,7-tetrahydrobenzo[c]thiophene-1-carboxamide;

N-(1-cyclopropyl-2-oxopyrrolidin-3-yl)-3-(5-(3,5-dichloro-4-fluorophenyl)-5-(trifluoromethyl)-4,5-dihydroisoxazol-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(4-oxocyclohexyl)-5,6-dihydro-4H-cyclopenta[c]thiophene-1-carboxamide;

3-(5-(3,5-dichlorophenyl)-5-(trifluoromethyl)-4,5-dihydroisoxazol-3-yl)-N-(2-oxo-1-(2,2,2-trifluoroethyl)pyrrolidin-3-yl)-5,6-dihydro-4H-cyclopenta[c]thiophene-1-carboxamide;

3-((R)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;

3-((S)-5-(3,5-dichlorophenyl)-5-(trifluoromethyl)-4,5-dihydroisoxazol-3-yl)-N—((R)-2-oxopyrrolidin-3-yl)-4,5,6,7-tetrahydrobenzo[c]thiophene-1-carboxamide;

N-(4-carbamoylphenyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide;

3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylicacid (3-carbamoyl-thiophen-2-yl)-amide;

2-(3-(5-(3,5-dichlorophenyl)-5-(trifluoromethyl)-4,5-dihydroisoxazol-3-yl)-4,5,6,7-tetrahydrobenzo[c]thiophene-1-carboxamido)acetic acid;

({3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl}-amino)-acetic acid;

N-(2-(cyanomethylamino)-2-oxoethyl)-3-(5-(3,5-dichlorophenyl)-5-(trifluoromethyl)-4,5-dihydroisoxazol-3-yl)-4,5,6,7-tetrahydrobenzo[c]thiophene-1-carboxamide;

3-(5-(3,5-dichlorophenyl)-5-(trifluoromethyl)-4,5-dihydroisoxazol-3-yl)-N-(2-oxo-2-(prop-2-ynylamino)ethyl)-4,5,6,7-tetrahydrobenzo[c]thiophene-1-carboxamide; or N-(2-(cyanomethylamino)-2-oxoethyl)-3-(5-(3,4,5-trichlorothiophen-2-yl)-5-(trifluoromethyl)-4,5-dihydroisoxazol-3-yl)-4,5,6,7-tetrahydrobenzo[c]thiophene-1-carboxamide.

8. The compound of claim 1 or a salt thereof, wherein A is

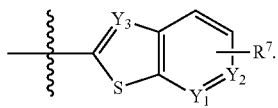

9. The compound of claim 8, or a salt thereof, wherein $Y_1$ is nitrogen.

10. The compound of claim 8, or a salt thereof, wherein $R^7$ is

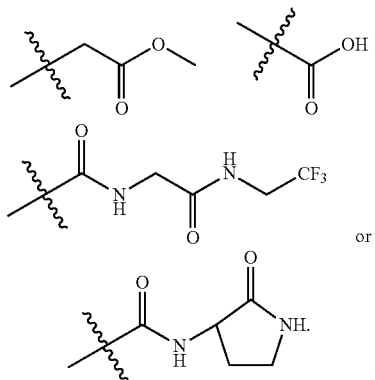

11. The compound of claim 8, or salt thereof, being 3-(4-chlorobenzo[b]thiophen-2-yl)-5-(3,5-dichlorophenyl)-5-(trifluoromethyl)-4,5-dihydroisoxazole;

2-[5-(3,5-Dichloro-phenyl)-5-trifluoromethyl-4,5-dihydro-isoxazol-3-yl]-thieno[2,3-c]pyridine;

5-Bromo-2-[5-(3,5-dichloro-phenyl)-5-trifluoromethyl-4,5-dihydro-isoxazol-3-yl]-thieno[2,3-b]pyridine;

2-[5-(3,5-Dichloro-phenyl)-5-trifluoromethyl-4,5-dihydro-isoxazol-3-yl]-thieno[2,3-b]pyridine;

3-(benzo[b]thiophen-2-yl)-5-(3,5-dichlorophenyl)-5-(trifluoromethyl)-4,5-dihydroisoxazole;

3-(benzo[d]thiazol-2-yl)-5-(3,5-dichlorophenyl)-5-(trifluoromethyl)-4,5-dihydroisoxazole;

5-(3,5-dichlorophenyl)-3-(3-methylbenzo[b]thiophen-2-yl)-5-(trifluoromethyl)-4,5-dihydroisoxazole;

5-(3,5-dichlorophenyl)-3-(5-methylbenzo[b]thiophen-2-yl)-5-(trifluoromethyl)-4,5-dihydroisoxazole;

3-(5-chlorobenzo[b]thiophen-2-yl)-5-(3,5-dichlorophenyl)-5-(trifluoromethyl)-4,5-dihydroisoxazole;

methyl 2-(5-(3,5-dichlorophenyl)-5-(trifluoromethyl)-4,5-dihydroisoxazol-3-yl)thieno[2,3-b]pyridine-5-carboxylate;

2-[5-(3,5-Dichloro-phenyl)-5-trifluoromethyl-4,5-dihydro-isoxazol-3-yl]-thieno[2,3-b]pyridine-5-carboxylic acid;

2-(5-(3,5-dichlorophenyl)-5-(trifluoromethyl)-4,5-dihydroisoxazol-3-yl)-N-(2-oxo-2-(2,2,2-trifluoroethylamino)ethyl)thieno[2,3-b]pyridine-5-carboxamide; or 2-(5-(3,5-dichlorophenyl)-5-(trifluoromethyl)-4,5-dihydroisoxazol-3-yl)-N—((R)-2-oxopyrrolidin-3-yl)thieno[2,3-b]pyridine-5-carboxamide.

12. The compound of claim 1, or salt thereof, being (S)-3-(5-(3,5-dichloro-4-fluorophenyl)-5-(trifluoromethyl)-4,5-dihydroisoxazol-3-yl)-N-(2-oxo-2-(2,2,2-trifluoroethylamino)ethyl)-5,6-dihydro-4H-cyclopenta[c]thiophene-1-carboxamide;

3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide;

(S)-3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide;

3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide;

(S)-3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid [(2-fluoro-ethylcarbamoyl)-methyl]-amide;

3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide; or (S)-3-(5-(3,5-dichloro-4-fluorophenyl)-5-(trifluoromethyl)-4,5-dihydroisoxazol-3-yl)-N-(2-oxo-2-(prop-2-ynylamino)ethyl)-5,6-dihydro-4H-cyclopenta[c]thiophene-1-carboxamide.

13. The compound of claim 12, or a salt thereof, wherein it is (S)-3-[5-(3,5-dichloro-4-fluoro-phenyl)-5-trifluoromethyl-4,5-dihydro-isoxazol-3-yl]-5,6-dihydro-4H-cyclopenta[c]thiophene-1-carboxylic acid [(2,2-difluoro-ethylcarbamoyl)-methyl]-amide.

14. A formulation comprising a compound of claim 1, or a salt thereof, and one or more acceptable carriers.

15. The formulation of claim 14 wherein it further comprises at least one additional active ingredient.

16. The formulation of claim 14 wherein it is a human pharmaceutical formulation.

17. The formulation of claim 14 wherein it is a veterinary pharmaceutical formulation.

18. A method of controlling a parasite infestation in or on an animal in need thereof comprising administering an effective amount of a compound of claim 1, or a salt thereof, to said animal.

19. The method of claim 18 wherein at least one other active ingredient is administered to said animal.

20. The method of claim 18 wherein said animal is a human.

21. The method of claim 18 wherein said animal is a companion animal.

22. The method of claim 21 wherein said companion animal is a dog or cat.

23. The method of claim 18 wherein said parasite is a tick.

24. The method of claim 18 wherein said animal is a livestock animal.

25. A method for preventing or treating diseases transmitted through parasites comprising administering an effective amount of a compound of claim 1, or a salt thereof, to an animal in need thereof.

26. The method of claim 25 wherein at least one other active ingredient is administered to said animal.

27. The method of claim 25 wherein said animal is a human.

28. The method of claim 15 wherein said animal is a companion animal.

29. The method of claim 28 wherein said companion animal is a dog or cat.

30. The method of claim 25 wherein said parasite is a tick.

31. The method of claim 25 wherein said animal is a livestock animal.

32. A method for controlling parasites, characterized in that a compound of claim 1, or a salt thereof, is allowed to act on the pests or their habitat, or both.

33. The method of claim 32 wherein the compound is placed on a plant or an animal.

34. A compound, or salt thereof, of Formula II

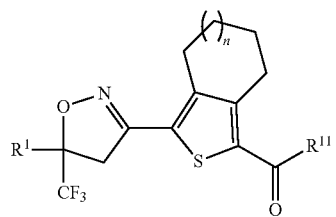

wherein n is 0 or 1;
$R^1$ is thienyl or phenyl, said thienyl or phenyl substituted with 2 or 3 of the same or different halo atoms; and
$R^{11}$ is hydroxy, —O—($C_1$-$C_4$ alkyl), or a halo atom.

35. The compound of claim 34, or a salt thereof, wherein $R^1$ is phenyl substituted with 2 or 3 of the same or different halo atoms.

36. The compound of claim 34, or a salt thereof, wherein $R^{11}$ is hydroxy.

37. The compound of claim 34, or a salt thereof, wherein it is
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid methyl ester;
3-[5-(3,5-Dichloro-phenyl)-5-trifluoromethyl-4,5-dihydro-isoxazol-3-yl]-5,6-dihydro-4H-cyclopenta[c]thiophene-1-carboxylic acid methyl ester;
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid methyl ester
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid methyl ester;
3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid methyl ester;
3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid methyl ester;
3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid methyl ester;
3-[5-(3,5-Dichloro-phenyl)-5-trifluoromethyl-4,5-dihydro-isoxazol-3-yl]-4,5,6,7-tetrahydro-benzo[c]thiophene-1-carboxylic acid;
3-[5-(3,5-Dichloro-phenyl)-5-trifluoromethyl-4,5-dihydro-isoxazol-3-yl]-5,6-dihydro-4H-cyclopenta[c]thiophene-1-carboxylic acid;
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carboxylic acid;
3-[5-(3,4,5-Trichloro-phenyl)-5-trifluoromethyl-4,5-dihydro-isoxazol-3-yl]-4,5,6,7-tetrahydro-benzo[c]thiophene-1-carboxylic acid;
3-[5-(3,5-Dichloro-4-fluoro-phenyl)-5-trifluoromethyl-4,5-dihydro-isoxazol-3-yl]-4,5,6,7-tetrahydro-benzo[c]thiophene-1-carboxylic acid;
3-[5-(3,5-Dichloro-4-fluoro-phenyl)-5-trifluoromethyl-4,5-dihydro-isoxazol-3-yl]-5,6-dihydro-4H-cyclopenta[c]thiophene-1-carboxylic acid;
3-[5-(3,4,5-Trichloro-phenyl)-5-trifluoromethyl-4,5-dihydro-isoxazol-3-yl]-5,6-dihydro-4H-cyclopenta[c]thiophene-1-carboxylic acid;
3-(5-(3,5-dichlorophenyl)-5-(trifluoromethyl)-4,5-dihydroisoxazol-3-yl)-4,5,6,7-tetrahydrobenzo[c]thiophene-1-carbonyl chloride; or
3-[5-(3,4,5-Trichloro-thiophen-2-yl)-5-trifluoromethyl-4,5-dihydro-isoxazol-3-yl]-4,5,6,7-tetrahydro-benzo[c]thiophene-1-carbonyl chloride.

38. A process for preparing

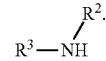

a compound, or salt thereof, of formula I

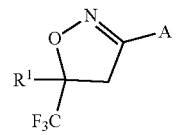

wherein A is

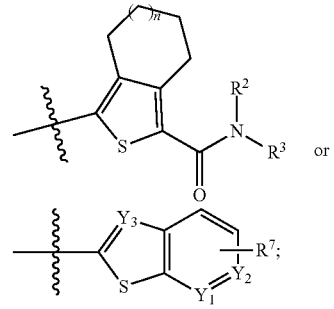

n is 0 or 1;
$R^1$ is thienyl or phenyl, said thienyl or phenyl substituted with 2 or 3 of the same or different halo atoms;
$R^2$ is at each occurrence independently hydrogen, $C_1$-$C_5$ alkyl, $C_3$-$C_6$ cycloalkyl, or $C_1$-$C_5$ haloalkyl;

$R^3$ is 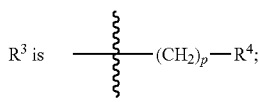

p is at each occurrence independently 0 or 1;

$R^4$ is $C_1$-$C_5$ alkyl, $C_1$-$C_5$ haloalkyl, $C_1$-$C_5$ cyanoalkyl, $C_1$-$C_5$ alkylthio, $C_3$-$C_6$ cycloalkyl optionally substituted with hydroxy, halo, or $C_1$-$C_5$ alkyl; $C_3$-$C_5$ cycloheteroalkyl optionally substituted with $C_1$-$C_5$ alkyl, $C_3$-$C_6$ cycloalkyl, or $C_1$-$C_5$ haloalkyl; phenyl, thienyl, pyridinyl, or

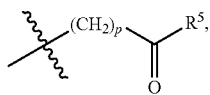

wherein one of the carbons in said cycloalkyls, independently, or cycloheteroalkyl may form a carbonyl group, and wherein said phenyl, thienyl, or pyridinyl is optionally substituted with alo or a carbamoyl group;

$R^5$ is hydroxy, —O—($C_1$-$C_5$ alkyl), or

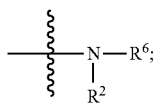

$R^6$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl;

or $R^2$ and $R^3$ combine to form, with the nitrogen to which they are attached,

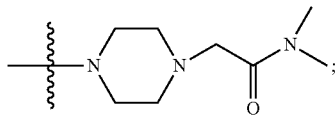 [SMILES: *N1CCN(CC(=O)N(C)C)CC1]

$Y_1, Y_2,$ and $Y_3$ are carbon or nitrogen with at most only one of $Y_1, Y_2,$ and $Y_3$ being nitrogen, and when $Y_1, Y_2,$ or $Y_3$ is a carbon, each may be substituted by $C_1$-$C_5$ alkyl;

$R^7$ is hydrogen, halo, $C_1$-$C_5$ alkyl, or

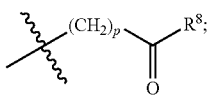

$R^8$ is hydroxy, —O—($C_1$-$C_5$ alkyl), or

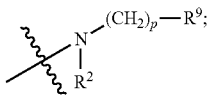

$R^9$ is $C_1$-$C_5$ alkyl,

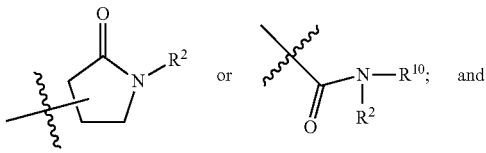

$R^{10}$ is hydrogen, $C_1$-$C_5$ alkyl, $C_1$-$C_5$ haloalkyl, $C_1$-$C_5$ cyanoalkyl, $C_1$-$C_5$ alkylthio, or $C_2$-$C_5$ alkynyl, comprising synthetically modifying a compound, or salt thereof, of formula II

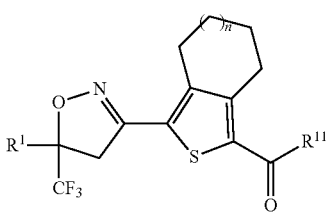

wherein n is 0 or 1;

$R^1$ is thienyl or phenyl, said thienyl or phenyl substituted with 2 or 3 of the same or different halo atoms; and $R^{11}$ is hydroxy, —O—($C_1$-$C_4$ alkyl), or a halo atom, with a compound of the formula

\* \* \* \* \*

UNITED STATES PATENT AND TRADEMARK OFFICE
CERTIFICATE OF CORRECTION

PATENT NO.         : 8,648,081 B2
APPLICATION NO.    : 13/883025
DATED              : February 11, 2014
INVENTOR(S)        : Zengyun An et al.

It is certified that error appears in the above-identified patent and that said Letters Patent is hereby corrected as shown below:

In the Claims:

At Column 101, Line 26, In claim 38, please delete "alo" and insert -- halo --, therefor.

Signed and Sealed this
Twenty-fourth Day of June, 2014

Michelle K. Lee
*Deputy Director of the United States Patent and Trademark Office*